(12) United States Patent
Mazar et al.

(10) Patent No.: US 6,696,416 B1
(45) Date of Patent: Feb. 24, 2004

(54) ANTI-INVASIVE AND ANTI-ANGIOGENIC COMPOSITIONS

(75) Inventors: Andrew P. Mazar, Escondido, CA (US); Terence R. Jones, San Diego, CA (US)

(73) Assignee: Angstrom Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/437,136

(22) Filed: Nov. 10, 1999

Related U.S. Application Data

(63) Continuation-in-part of application No. 08/900,327, filed on Jul. 25, 1997, now Pat. No. 5,994,309.

(51) Int. Cl.$^7$ .............................................. A61K 38/00
(52) U.S. Cl. ............................... 514/16; 514/2; 514/12; 530/324
(58) Field of Search ............................... 514/16, 2, 12; 530/324

(56) References Cited

FOREIGN PATENT DOCUMENTS

| WO | 90/12872 | 11/1990 |
| WO | 94/28014 | 12/1994 |
| WO | 97/05257 | 2/1997 |
| WO | 97/25422 | 7/1997 |

OTHER PUBLICATIONS

Joy Virology Feb. 1990 p 680–685, Porynstead et al.*
Smith E.A.: "Peptides, chemistry and biology, Proceedings 12$^{th}$ APS, 1991 Cambridge" 1992, ESCOM, LEIDEN XP002083073 Lie e.a.: The inhibition of fibrin stimulated τ–PA–induced plasminogen activation by the A chain fragment 149–157 or urokinase; see pp. 810–811, esp. table 1.
Wiley, R.A., et al., "Peptidomimetic Derived from Natural Products," *Medicinal Research Reviews* (1993) 13(3):328–384.
Claeson, G., "Synthetic peptides and peptidomimetics as substrates and inhibitors or thrombin and other proteases in blood coagulation system," *Blood Coagulation and Fibrinolysis* (1994) 5:411–436.
Hruby, V.J., "Conformational and Topographical Considerations in the Design of Biologically Active Peptides", *Biopolymers* (1993) 33:1073–1082.
Kempf, D.J., "Design of Symmetry–Based, Peptidomimetic Inhibitors of Human Immunodeficiency Virus Protease," *Methods In Enzymology* (1994) 241:334–354.
Parish, C.R., et al., "A Basement–Membrane Permeability Assay which Correlates with the Metastatic Potential of Tumour Cells," *Int. J. Cancer* (1992) 52:378–383.
Hoosein, N.M., et al., "Involvement of Urokinase and its Receptor In the Invasiveness of Human Prostatic Carcinoma Cell Lines," *Cancer Communications* (1991) 3(8):255–264.
Chambers, S.K., et al., "Macrophage Colony–stimulating Factor Mediates Invasion of Ovarian Cancer Cells through Urokinase," *Cancer Research* (1995) 55:1578–1585.
Rabbani, S.A., et al., "Prevention of Prostate–Cancer Metastasis in vivo by a Novel Synthetic Inhibitor or Urokinase–type Plasminogen," *Int. J. Cancer* (1995) 63:840–845.
Min, H.Y., et al., "Urokinase Receptor Antagonists Inhibit Angiogenesis and Primary Tumor Growth in Synergeric Mice," *Cancer Research* (1996) 56:2428–2433.
Schnaper, H.W., et al., "Plasminogen Activators Augment Endothelial Cell Organization In Vivo by Two Distinct Pathways," *Journal of Cellular Physiology* (1995) 165:107–118.
Odedra, R., et al., "Low Molecular Weight Angiogenesis Factors," *Pharmac. Ther.* (1991) 49:111–124.

* cited by examiner

*Primary Examiner*—Geetha P. Bansal
(74) *Attorney, Agent, or Firm*—Shmuel Livnat; Venable, Baetjer, Howard & Civiletti, LLP

(57) ABSTRACT

A peptide compound having the sequence Lys-Pro-Ser-Ser-Pro-Pro-Glu-Glu [SEQ ID NO:2] or a substitution variant, addition variant or other chemical derivative thereof inhibits cell invasion, endothelial tube formation or angiogenesis in vitro. A number of substitution variants and addition variants of this peptide, preferably capped at the N- and C-termini, as well as peptidomimetic derivatives, are useful for treating diseases and conditions mediated by undesired and uncontrolled cell invasion and/or angiogenesis. Pharmaceutical compositions comprising the above peptides and derivatives are administered to subjects in need of such treatment in a dosage sufficient to inhibit invasion and/or angiogenesis . The disclosed compositions and methods are particularly useful for suppressing the growth and metastasis of tumors.

8 Claims, 24 Drawing Sheets

ANTI-INVASIVE AND ANTI-ANGIOGENIC COMPOSITIONS

CROSS-REFERENCE TO RELATED APPLICATIONS

This application is a continuation-in-part of U.S. patent application Ser. No. 08/900,327, filed Jul. 25, 1997 now U.S. Pat. No. 5,994,309, from which priority is claimed pursuant to 35 U.S.C. § 120, and which disclosure is hereby incorporated by reference in its entirety.

BACKGROUND OF THE INVENTION

1. Field of the Invention

The invention in the fields of biochemistry, organic chemistry and medicine relates to peptide compounds and methods of their use to treat diseases and conditions associated with movement, migration and adhesion of cells including diseases that involve angiogenesis such as tumor invasion and metastasis.

2. Description of the Background Art

Several disease processes have been demonstrated to require the invasion or migration of cells as part of their pathology. These include tumor invasion, tumor metastasis, pathological angiogenesis, inflammation, and endometriosis (Liotta et al., 1991; Fox et al., 1996; Osborn, 1990; Mareel et al., 1990; Aznavoorian et al., 1993; Lennarz and Strittmatter, 1991; Fernandez-Shaw et al., 1995).

In the case of tumor angiogenesis, quiescent endothelial cells can become motile in response to a variety of angiogenic growth factors as well as to changes in the basement membrane induced by tumor cells and various accessory cells found within a tumor (Blood and Zetter, 1990; Liotta et al., 1991; Odedra and Weiss, 1991). Neovascularization of a tumor enables the metastatic spread of aggressive tumor cells by (1) providing a route of escape for the metastatic cells as well as (2) nurturing the tumor by providing a growth-conducive environment (Cornelius et al., 1995; Blood and Zetter, 1990; Weaver et al., 1997; Weinstat-Saslow and Steeg, 1994; Leek et al., 1994).

The process of tumor metastasis may be viewed as bi-directional, comprising the following steps (1) endothelial cells migrate into a tumor in response to a chemotactic gradient produced by the tumor cells or by accessory cells (stromal cells, leukocytes); and (2) aggressive tumor cells concomitantly invade toward the developing neovasculature.

The process of invasion may further fuel angiogenesis by the proteolytic release of growth/angiogenic factors bound to extracellular matrix (ECM), including basic fibroblast growth factor (bFGF), vascular endothelial growth factor (VEGF), and hepatocyte growth factor (HGF) as well as other factors including interleukin -8 (IL-8) and granulocyte-macrophage colony stimulating factor (GM-CSF). Also generated are proteolytic fragments of the ECM which are themselves chemotactic for both tumor cells and endothelial cells (Fox et al., 1996; Leek et al., 1994; Vlodavsky et al., 1990; Sweeney et aL, 1991; Taipale and Keski-Oja, 1997).

It has been suggested that only 1–2% of the total cells in a tumor are capable of metastasis. As this statement is based on a static view of the tumor phenotype, it is probably inaccurate. In reality, metastasis appears to depend on disseminated tumor cells becoming exposed to an environment which supports their spread and survival (Weaver et al., 1997). In the majority of patients presenting with a clinically detectable primary tumor, metastasis has already occurred (Welch, 1997). Metastatic disease occurs when the disseminated foci of tumor cells seed a tissue which supports their growth and propagation, and this secondary spread of tumor cells is responsible for the morbidity and mortality associated with the majority of cancers. Clinical management of metastatic disease is often unsuccessful with conventional cytotoxic therapies. Metastasis differs substantially from the growth of the primary tumor in that it involves the simultaneous outgrowth of many foci which are phenotypically similar from the standpoint of their aggressiveness This outgrowth is dependent on the ability of cells that have metastasized to invade locally and to recruit neovessels.

By preventing interaction of adhesion molecules, the important process of cell migration/invasion and angiogenesis can be diminished or halted, with a number of important consequences for those diseases and conditions which are caused in part by undesirable cell migration, invasion and angiogenesis. In addition to vascular phenomena, such cell migration/invasion is important in tumor metastasis, which can be suppressed by the compositions and methods disclosed herein. Administration of effective amounts of these compositions will also disrupt the molecular interactions required for angiogenesis.

The art recognizes the need for novel treatments of subjects with cancer, in particular patients with metastatic cancer who have the poorest prognosis. Such treatment should be as devoid as possible of undesired side effects such as those associated with conventional chemotherapy and some of the experimental biotherapies. The present invention is directed to this objective. Inhibition of tumor cell invasion and endothelial cell migration (an important component of the angiogenic process) provide a novel approach to treating subjects with metastatic cancer. By inhibiting the local spread of tumor cells and angiogenesis at metastatic sites, metastatic foci should be induced to regress due to deprivation of their blood supply thus encouraging the subsequent expression of the cells' endogenous apoptotic program.

Furthermore, the inhibition of invasion of tissue by leukocytes and the concomitant angiogenesis would be useful for treating inflammation and other disease processes wherein cellular invasiveness is part of the pathogenic process. Inflammation and tumor invasion and metastasis and angiogenesis are known to involve similar mechanisms and extracellular factors (Liotta et al., 1991; Fox et al., 1996; Osborn, 1990; Mareel et al., 1990; Aznavoorian et al., 1993; Lennarz and Strittmatter, 1993).

Blasi et al. (U.S. Pat. No. 5,416,006) discloses plasminogen activators and their chemical modification, in particular phosphorylated uPA and tPA as thrombolytic agents. These workers examined phosphorylated uPA by generating tryptic phosphopeptides therefrom and noted the existence of KPSSPPEELK [SEQ ID NO:1] (corresponding to positions 136–145 of uPA). This decapeptide was not tested for any function, nor ascribed any properties of functional relevance. More importantly, as disclosed herein, this peptide (unphosphorylated), capped or uncapped, is inactive in an in vitro assay of cell invasion.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present invention provides methods and compositions for treating diseases and processes mediated by undesired and uncontrolled cell invasion and/or angiogenesis by administering to an animal a composition comprising an oligopeptide, chemical derivative or peptidomimetic in a dosage sufficient to inhibit the invasion and/or angiogenesis. The present invention is particularly useful for treating or for suppressing the growth of tumors. Administration of the composition to a human or subject with prevascularized metastasized tumors will prevent the growth or expansion of those tumors.

Thus, the present invention is directed to a peptide compound having the sequence Lys-Pro-Ser-Ser-Pro-Pro-Glu-Glu (also abbreviated in single letter amino acid code as KPSSPPEE) [SEQ ID NO:2] or a substitution variant, addition variant or other chemical derivative thereof. The preferred peptide, variant or derivative is "capped" at the amino and carboxyl termini, wherein (a) acetyl (abbreviated as "Ac") is boun*d to the N at the amino-terminus and (b) an amino group (abbreviated as "Am") is bound to the C-terminal carboxyl group. In general, this capped peptide will be written "Ac-KPSSPPEE-Am" throughout this document using the single letter amino acid code and indicating the blocking groups as Ac and Am. This compound is also designated "Å6" and will therefore be referred to by this name as well.

The peptide, variant or derivative of this invention has one or more of the following activities:

(a) at least about 20% of the biological activity of Ac-KPSSPPEE-Am in one or more of the following in vitro bioassays: (i) invasion in a Matrigel® assay; (ii) endothelial tube formation on Matrigel®, or (iii) endothelial tube formation on a fibrin matrix in the presence of basic fibroblast growth factor and vascular endothelial growth factor; or (b) binding activity such that it competes with labeled Ac-KPSSPPEE-Am for binding to a cell or molecule which has a binding site for Ac-KPSSPPEE-Am.

In a preferred embodiment, the peptide or peptide variant is capped at both ends with an N-terminal acetyl group and a C terminal amide group.

A preferred substitution or addition variant of the peptide, or a chemical derivative of the variant, has an amino acid sequence selected from the group consisting of:

(a) SEQ ID NO:2 wherein the Glu at position 7 or 8 or both is replaced by one or any two of the substituent amino acids Gln, Asp or Asn;

(b) SEQ ID NO:2 wherein Ser at position 3 or 4 or both is replaced by one or any two of the substituent amino acids Thr, Ala, Gly, hSer (homoserine) or ValβOH (β-hydroxyvaline);

(c) SEQ ID NO:2 wherein the Lys at position 1 is replaced by His, Arg, Gln, Orn (omithine), Cit (citrulline) or Hci (homocitrulline);

(d) SEQ ID NO:2 wherein the Pro at position 2, 5 or 6 is replaced by Hyp (hydroxyproline);

(e) an addition variant of SEQ ID NO:2, wherein Leu, Ile, Val, Nva (norvaline), Nle (norleucine), Met, Ala, or Gly is added to the C-terminal Glu or to any C-terminal substituent for Glu at position 8 as disclosed above.

(f) an addition variant of SEQ ID NO:2, wherein any of the following peptides are added to the C-terminal Glu or to the C terminal substituent for Glu at position 8: Leu-(Gly)$_n$; Ile-(Gly)$_n$; Val-(Gly)$_n$; Nva-(Gly)$_n$; or Nle-(Gly)$_n$, wherein n=1–10.

(g) an addition variant of SEQ ID NO:2 wherein one or more of the following residues or peptides is added to the N-terminal Lys, or to any N-terminal substituent of Lys at position 1 as disclosed: Gly, Lys-(Gly)$_n$; Tyr-(Gly)$_n$; or Gly-(Gly)$_n$, wherein n=1–10; and (h) a combination of one or more of (a)–(g).

In a preferred embodiment, the chemical derivative above is a peptidomimetic agent.

Also provided is a multimer of the peptide or variant above, which, when the peptide is not a variant, has the formula: (KPSSPPEE-X$_m$)$_n$-KPSSPPEE wherein X is selected from the group consisting of $C_1$–$C_{20}$ alkyl, $C_1$–$C_{20}$ alkenyl, $C_1$–$C_{20}$ alkynyl, $C_1$–$C_{20}$ polyether containing up to 9 oxygen atoms and Gly$_m$, and wherein m=0 or 1, n=1–100 and z=1–10.

The invention is further directed to a pharmaceutical composition useful for inhibiting invasion of tumor cells or angiogenesis, comprising (a) any of the above peptides, variants or chemical derivatives including a peptidomimetic or a multimeric peptide and (b) a pharmaceutically acceptable carrier or excipient.

Also included is a method for inhibiting the invasiveness of tumor cells comprising contacting the cells with an effective amount of a peptide, variant or derivative as above.

In another embodiment, a method is provided for inhibiting tumor invasion or metastasis in a subject comprising administering to the subject any of the above pharmaceutical compositions.

Also provided is a method for inhibiting cell migration, invasion, migration induced cell proliferation or angiogenesis in a subject having a disease or condition associated with undesired cell migration, invasion, migration-induced proliferation, or angiogenesis comprising administering to the subject an effective amount of a pharmaceutical composition as described above.

In any of the foregoing methods, the disease or condition being treated may be primary tumor growth, tumor invasion or metastasis, atherosclerosis, post-balloon angioplasty vascular restenosis, neointima formation following vascular trauma, vascular graft restenosis, fibrosis associated with a chronic inflammatory condition, lung fibrosis, chemotherapy-induced fibrosis, wound healing with scarring and fibrosis, psoriasis, deep venous thrombosis, or another disease or condition in which angiogenesis is pathogenic. The treatment methods are most preferred for tumor growth, invasion or metastasis.

BRIEF DESCRIPTION OF THE DRAWINGS

FIG. 4: the Å6 (50 μg/mL) concentration was kept constant and the concentration of cisplatin ("CDDP") was varied; FIG. 5: CDDP was kept constant at a sub-optimal dose(1 μg/mL) and Å6 was varied.

FIG. 12: The volume of the primary challenge tumor was determined using caliper measurements. Inhibition of tumor growth by Å6 was most effective when the tumors were small. FIG. 13: Macroscopic metastasis was also inhibited by Å6 treatment. Control animals received vehicle (PBS) only.

DESCRIPTION OF THE PREFERRED EMBODIMENTS

Figure 1:
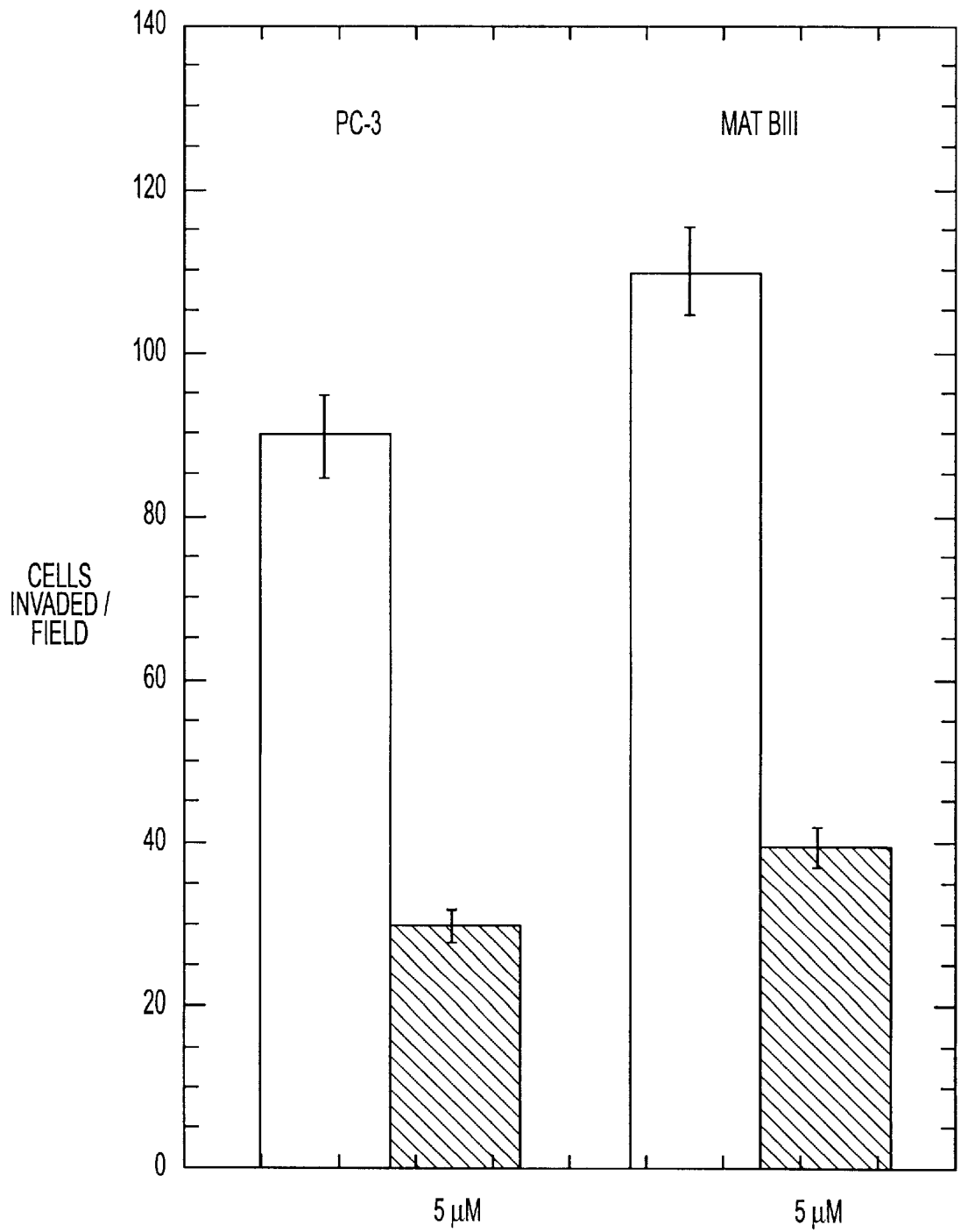
FIG. 1 is a graph showing the inhibitory effect of Ac-Lys-Pro-Ser-Ser-Pro-Pro-Glu-Glu-Am (5 μM) on the in vitro invasion of both human (PC-3) and rat (Mat BIII) tumor cell lines in a Matrigel® system as described in the Examples. The left bar of each pair is the control group and the right bar represents cells responding in the presence of the peptide.

The present inventors have discovered a novel peptide and related compounds which act as inhibitors of angiogenesis and invasiveness and have devised various methods for using this peptide for diagnosis, therapy and receptor identification. The peptide is a potent and specific inhibitor of (a) cell invasion, (b) angiogenesis at tumor sites including sites of metastasis, and (c) inflammatory responses.

In addition, the peptide and its derivatives are designed to be highly soluble in aqueous buffer and body fluids but not in lipids. This property limits non-specific partitioning into membranes. Non-specific partitioning of compounds into and across membranes is a frequent cause of toxicity. The compounds of this invention have minimal toxicity because, owing to their possessing Coulombic charge, they are not expected to partition into cells. The target(s) of the compositions are extracellular, and method(s) of this invention are predicated on the compositions acting first in the extracellular space. Therefore, it is desirable to maintain the compounds in the extracellular space.

Additional pharmacological advantage is obtained due to the high solubility limit of the compounds, allowing their delivery in high concentrations in the absence of co-solvents or extraordinary excipients.

Compounds of the invention have been shown by the present inventors (see Example II) to block the invasion of both human and rat tumor cells in vitro in the Matrigel® system.

In addition, they block endothelial cell tube formation in response to bFGF and VEGF in either a fibrin matrix or when the endothelial cells are plated on Matrigel®.

The compounds of the invention also inhibit experimental metastasis in a xenograft model in nu/nu mice using the human prostatic carcinoma cell line, PC-3, transfected with the green fluorescent protein (GFP) as a reporter. Finally, the compounds also inhibit tumor progression, spontaneous metastasis and angiogenesis in a syngeneic rat model of breast cancer.

The Peptide Compositions

The original inhibitory capped peptide discovered by the present inventors has 8 amino acid residues with a molecular weight of 911 Da. This preferred peptide is characterized by the sequence:

CH$_3$CO-Lys-Pro-Ser-Ser-Pro-Pro-Glu-Glu-NH$_2$ [SEQ ID NO:2]

The amino and carboxyl termini are preferably blocked or "capped" with acetyl (CH$_3$CO—, bound to the amino-terminal N; also abbreviated as "Ac") and amino (—NH$_2$ bound to the C-terminal carboxyl group; also abbreviated as "Am"), respectively. This peptide will also be referred to below in single letter code indicating the blocking groups as Ac and Am groups: Ac-KPSSPPEE-Am.

The N-terminal capping function is preferably in a linkage to the terminal amino group and may be selected from the group consisting of:

formyl;

alkanoyl, having from 1 to 10 carbon atoms, such as acetyl, propionyl, butyryl;

alkenoyl, having from 1 to 10 carbon atoms, such as hex-3-enoyl;

alkynoyl, having from 1 to 10 carbon atoms, such as hex-5-ynoyl;

aroyl, such as benzoyl or 1-naphthoyl;

heteroaroyl, such as 3-pyrroyl or 4-quinoloyl;

alkylsulfonyl, such as methanesulfonyl;

arylsulfonyl, such as benzenesulfonyl or sulfanilyl;

heteroarylsulfonyl, such as pyridine-4-sulfonyl;

substituted alkanoyl, having from 1 to 10 carbon atoms, such as 4-aminobutyryl;

substituted alkenoyl, having from 1 to 10 carbon atoms, such as 6-hydroxy-hex-3-enoyl;

substituted alkynoyl, having from 1 to 10 carbon atoms, such as 3-hydroxy-hex-5-ynoyl;

substituted aroyl, such as 4-chlorobenzoyl or 8-hydroxy-naphth-2-oyl;

substituted heteroaroyl, such as 2,4-dioxo-1,2,3,4-tetrahydro-3-methyl-quinazolin-6-oyl;

substituted alkylsulfonyl, such as 2-aminoethanesulfonyl;

substituted arylsulfonyl, such as 5-dimethylamino-1-naphthalenesulfonyl;

substituted heteroarylsulfonyl, such as 1-methoxy-6-isoquinolinesulfonyl;

carbamoyl or thiocarbamoyl;

substituted carbamoyl (R'—NH—CO) or substituted thiocarbamoyl (R'—NH—CS) wherein R' is alkyl, alkenyl, alkynyl, aryl, heteroaryl, substituted alkyl, substituted alkenyl, substituted alkynyl, substituted aryl, or substituted heteroaryl;

substituted carbamoyl (R'—NH—CO) and substituted thiocarbamoyl (R'—NH—CS) wherein R' is alkanoyl, alkenoyl, alkynoyl, aroyl, heteroaroyl, substituted alkanoyl, substituted alkenoyl, substituted alkynoyl, substituted aroyl, or substituted heteroaroyl, all as above defined;

Lys-(Gly)$_n$, where n=1 4; or Tyr-(Gly)$_n$ where n=1 4.

The C-terminal capping function can either be in an amide bond with the terminal carboxyl or in an ester bond with the terminal carboxyl. Capping functions that provide for an amide bond are designated as NR$^1$R$^2$ wherein R$^1$ and R$^2$ may be independently drawn from the following group:

hydrogen;

alkyl, preferably having from 1 to 10 carbon atoms, such as methyl, ethyl, isopropyl;

alkenyl, preferably having from 1 to 10 carbon atoms, such as prop-2-enyl;

alkynyl, preferably having from 1 to 10 carbon atoms, such as prop-2-ynyl;

substituted alkyl having from 1 to 10 carbon atoms, such as hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl;

substituted alkenyl having from 1 to 10 carbon atoms, such as hydroxyalkenyl, alkoxyalkenyl, mercaptoalkenyl, alkylthioalkenyl, halogenoalkenyl, cyanoalkenyl, aminoalkenyl, alkylaminoalkenyl, dialkylaminoalkenyl, alkanoylalkenyl, carboxyalkenyl, carbamoylalkenyl;

substituted alkynyl having from 1 to 10 carbon atoms, such as hydroxyalkynyl, alkoxyalkynyl, mercaptoalkynyl, alkylthioalkynyl, halogenoalkynyl, cyanoalkynyl, aminoalkynyl, alkylaminoalkynyl, dialkylaminoalkynyl, alkanoylalkynyl, carboxyalkynyl, carbamoylalkynyl;

aroylalkyl having up to 10 carbon atoms, such as phenacyl or 2-benzoylethyl;

aryl, such as phenyl or 1-naphthyl;

heteroaryl, such as 4-quinolyl;

alkanoyl having from 1 to 10 carbon atoms, such as acetyl or butyryl;

aroyl, such as benzoyl;

heteroaroyl, such as 3-quinoloyl;

OR' or NR'R" where R' and R" are independently hydrogen, alkyl, aryl, heteroaryl, acyl, aroyl, sulfonyl, sulfinyl, or $SO_2$—R''' or SO—R''' where R''' is substituted or unsubstituted alkyl, aryl, heteroaryl, alkenyl, or alkynyl.

Capping functions that provide for an ester bond are designated as OR, wherein R may be: alkoxy; aryloxy; heteroaryloxy; aralkyloxy; heteroaralkyloxy; substituted alkoxy; substituted aryloxy; substituted heteroaryloxy; substituted aralkyloxy; or substituted heteroaralkyloxy.

Either the N-terminal or the C-terminal capping function, or both, may be of such structure that the capped molecule functions as a prodrug (a pharmacologically inactive derivative of the parent drug molecule) that undergoes spontaneous or enzymatic transformation within the body in order to release the active drug and that has improved delivery properties over the parent drug molecule (Bundgaard, 1985).

Judicious choice of capping groups allows the addition of other activities on the peptide. For example, the presence of a sulfhydryl group linked to the N- or C-terminal cap will permit conjugation of the derivatized peptide to other molecules.

Capping of the peptide is intended primarily to increase plasma half life, as has been demonstrated for many peptides (e.g., Powell et al., *Ann Repts Med. Chem.* 28:285–294, 1993). Any capping group which serves this function is intended. However, the uncapped form is still useful as a template for peptidomimetic design (see below) and may have acceptable activity in vitro.

Production of Peptides and Derivatives

General Chemical Synthetic Procedures

The peptides of the invention may be prepared using recombinant DNA technology. However, given their length, they are preferably prepared using solid-phase synthesis, such as that generally described by Merrifield, *J Amer. Chem. Soc.*, 85:2149–54 (1963), although other equivalent chemical syntheses known in the art are also useful. Solid-phase peptide synthesis may be initiated from the C-terminus of the peptide by coupling a protected α-amino acid to a suitable resin. Such a starting material can be prepared by attaching an α-amino-protected amino acid by an ester linkage to a chloromethylated resin or to a hydroxymethyl resin, or by an amide bond to a BHA resin or MBHA resin.

The preparation of the hydroxymethyl resin is described by Bodansky et al., 1966. Chloromethylated resins are commercially available from BioRad Laboratories, Richmond, Calif. and from Lab. Systems, Inc. The preparation of such a resin is described by Stewart et al., 1969. BHA and MBHA resin supports are commercially available and are generally used only when the desired polypeptide being synthesized has an unsubstituted amide at the C-terminus.

The amino acids can be coupled to the growing peptide chain using techniques well known in the art for the formation of peptide bonds. For example, one method involves converting the amino acid to a derivative that will render the carboxyl group of the amino acid more susceptible to reaction with the free N-terminal amino group of the growing peptide chain. Specifically, the C-terminal of the protected amino acid can be converted to a mixed anhydride by the reaction of the C-terminal with ethyl chloroforrnate, phenyl chloroformate, sec-butyl chloroformate, isobutyl chloroformate, or pivaloyl chloride or the like acid chlorides. Alternatively, the C-terrninal of the amino acid can be converted to an active ester, such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole. Another coupling method involves the use of a suitable coupling agent, such as N,N'-dicyclohexylcarbodiimide or N,N'-diisopropylcarbodiimide. Other appropriate coupling agents, apparent to those skilled in the art, are disclosed in Gross et al. 1979, which is hereby incorporated by reference.

The α-amino group of each amino acid employed in the peptide synthesis must be protected during the coupling reaction to prevent side reactions involving their active α-amino function. Certain amino acids contain reactive side-chain functional groups (e.g., sulfhydryl, amino, carboxyl, and hydroxyl) and such functional groups must also be protected with suitable protecting groups to prevent a chemical reaction from occurring at either (1) the α-amino group site or (2) a reactive side chain site during both the initial and subsequent coupling steps.

In the selection of a particular protecting group to be used in synthesizing the peptides, the following general rules are typically followed. Specifically, an α-amino protecting group (1) should render the α-amino function inert under the conditions employed in the coupling reaction, (2) should be readily removable after the coupling reaction under conditions that will not remove side-chain protecting groups and will not alter the structure of the peptide fragment, and (3) should substantially reduce the possibility of racemization upon activation, immediately prior to coupling.

On the other hand, a side-chain protecting group (1) should render the side chain functional group inert under the conditions employed in the coupling reaction, (2) should be stable under the conditions employed in removing the α-amino protecting group, and (3) should be readily removable from the desired fully-assembled peptide under reaction conditions that will not alter the structure of the peptide chain.

It will be apparent to those skilled in the art that the protecting groups known to be useful for peptide synthesis vary in reactivity with the agents employed for their removal. For example, certain protecting groups, such as triphenylmethyl and 2-(p-biphenyl)isopropyloxycarbonyl, are very labile and can be cleaved under mild acid conditions. Other protecting groups, such as t-butyloxycarbonyl (BOC), t-amyloxycarbonyl, adamantyl-oxycarbonyl, and p-methoxybenzyloxycarbonyl, are less labile and require moderately strong acids for their removal, such as trifluoroacetic, hydrochloric, or boron trifluoride in acetic acid. Still other protecting groups, such as benzyloxycarbonyl (CBZ or Z), halobenzyloxycarbonyl, p-nitrobenzyloxycarbonyl cycloalkyloxycarbonyl, and isopropyloxycarbonyl, are even less labile and require even stronger acids, such as hydrogen fluoride, hydrogen bromide, or boron trifluoroacetate in trifluoroacetic acid, for their removal. Suitable protecting groups, known in the art are described in Gross et al. 1981.

Among the classes of amino acid protecting groups useful for protecting the α-amino group or for protecting a side chain group are included the following.

(1) For an α-amino group, three typical classes of protecting groups are:

(a) aromatic urethane-type protecting groups, such as fluorenylmethyloxycarbonyl (FMOC), CBZ, and substituted CBZ, such as, p-chlorobenzyloxycarbonyl, p-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like;

(b) aliphatic urethane-type protecting groups, such as BOC, t-amyloxycarbonyl, isopropyloxycarbonyl, 2-(p-biphenyl)isopropyloxycarbonyl, allyloxycarbonyl and the like; and (c) cycloalkyl urethane-type protecting groups, such as cyclopentyloxycarbonyl, adamantyloxycarbonyl, and cyclohexyloxycarbonyl.

The preferred α-amino protecting groups are BOC and FMOC.

(2) For the side chain amino group present in Lys, protection may be by any of the groups mentioned above in (1) such as BOC, 2-chlorobenzyloxycarbonyl and the like.

(3) For the guanidino group of Arg, protection may be provided by nitro, tosyl, CBZ, adamantyloxycarbonyl, 2,2,5,7,8-pentamethylchroman-6-sulfonyl, 2,3,6-trimethyl-4-methoxyphenylsulfonyl, or BOC groups.

(4) For the hydroxyl group of Ser or Thr, protection may be, for example, by t-butyl; benzyl (BZL); or substituted BZL, such as p-methoxybenzyl, p-nitrobenzyl, p-chlorobenzyl, o-chlorobenzyl, and 2,6-dichlorobenzyl.

(5) For the carboxyl group of Asp or Glu, protection may be, for example, by esterification using such groups as BZL, t-butyl, cyclohexyl, cyclopentyl, and the like.

(6) For the imidazole nitrogen of His, the benzyloxymethyl (BOM) or tosyl moiety is suitably employed as a protecting group.

(7) For the phenolic hydroxyl group of Tyr, a protecting group such as tetrahydropyranyl, tert-butyl, trityl, BZL, chlorobenzyl, 4-bromobenzyl, and 2,6-dichlorobenzyl are suitably employed. The preferred protecting group is bromobenzyloxycarbonyl.

(8) For the side chain amino group of Asn or Gln, xanthyl (Xan) is preferably employed.

(9) For Met, the amino acid is preferably left unprotected.

(10) For the thio group of Cys, p-methoxybenzyl is typically employed.

The first C-terminal amino acid of the growing peptide chain, e.g., Glu, is typically protected at the α-amino position by an appropriately selected protecting group such as BOC. The BOC-Glu-(γ-cyclohexyl)-OH can be first coupled to a benzylhydrylamine resin using isopropylcarbodiimide at about 25° C. for two hours with stirring or to a chloromethylated resin according to the procedure set forth in Horiki et al., 1978. Following the coupling of the BOC-protected amino acid to the resin support, the α-amino protecting group is usually removed, typically by using trifluoroacetic acid (TFA) in methylene chloride or TFA alone. The α-amino group de-protection reaction can occur over a wide range of temperatures, but is usually carried out at a temperature between about 0° C. and room temperature.

Other standard α-amino group de-protecting reagents, such as HCl in dioxane, and conditions for the removal of specific α-amino protecting groups are within the skill of those working in the art, such as those described in Lübke et al., 1975, which is hereby incorporated by reference. Following the removal of the α-amino protecting group, the unprotected α-amino group, generally still side-chain protected, can be coupled in a stepwise manner in the intended sequence.

An alternative to the stepwise approach is the fragment condensation method in which pre-formed peptides of short length, each representing part of the desired sequence, are coupled to a growing chain of amino acids bound to a solid phase support. For this stepwise approach, a particularly suitable coupling reagent is N,N'-dicyclohexylcarbodiimide or diisopropylcarbodiimide. Also, for the fragment approach, the selection of the coupling reagent, as well as the choice of the fragmentation pattern needed to couple fragments of the desired nature and size are important for success and are known to those skilled in the art.

Each protected amino acid or amino acid sequence is usually introduced into the solid-phase reactor in amounts in excess of stoichiometric quantities, and the coupling is suitably carried out in an organic solvent, such as dimethylformamide (DMF), $CH_2Cl_2$ or mixtures thereof. If incomplete coupling occurs, the coupling procedure is customarily repeated before removal of the N-amino protecting group in preparation for coupling to the next amino acid. Following the removal of the α-amino protecting group, the remaining α-amino and side-chain-protected amino acids can be coupled in a stepwise manner in the intended sequence. The success of the coupling reaction at each stage of the synthesis may be monitored. A preferred method of monitoring the synthesis is by the ninhydrin reaction, as described by Kaiser et al., 1970. The coupling reactions can also be performed automatically using well-known commercial methods and devices, for example, a Beckman 990 Peptide Synthesizer.

Upon completion of the desired peptide sequence, the protected peptide must be cleaved from the resin support, and all protecting groups must be removed. The cleavage reaction and removal of the protecting groups is suitably accomplished concomitantly or consecutively with de-protection reactions. When the bond anchoring the peptide to the resin is an ester bond, it can be cleaved by any reagent that is capable of breaking an ester linkage and of penetrating the resin matrix. One especially useful method is by treatment with liquid anhydrous hydrogen fluoride. This reagent will usually not only cleave the peptide from the resin, but will also remove all acid-labile protecting groups and, thus, will directly provide the fully de-protected peptide. When additional protecting groups that are not acid-labile are present, additional de-protection steps must be carried out. These steps can be performed either before or after the hydrogen fluoride treatment described above, according to specific needs and circumstances.

When a chloromethylated resin is used, the hydrogen fluoride cleavage/de-protection treatment generally results in the formation of the free peptide acids. When a benzhydrylamine resin is used, the hydrogen fluoride treatment generally results in the free peptide amides. Reaction with hydrogen fluoride in the presence of anisole and dimethylsulfide at 0° C. for one hour will typically remove the side-chain protecting groups and, concomitantly, release the peptide from the resin.

When it is desired to cleave the peptide without removing protecting groups, the protected peptide-resin can be subjected to methanolysis, thus yielding a protected peptide in which the C-terminal carboxyl group is methylated. This methyl ester can be subsequently hydrolyzed under mild alkaline conditions to give the free C-terminal carboxyl group. The protecting groups on the peptide chain can then be removed by treatment with a strong acid, such as liquid hydrogen fluoride. A particularly useful technique for methanolysis is that of Moore et al., 1977, in which the protected peptide-resin is treated with methanol and potassium cyanide in the presence of a crown ether.

Other methods for cleaving a protected peptide from the resin when a chloromethylated resin is employed include (1)

ammoniolysis and (2) hydrazinolysis. If desired, the resulting C-terminal amide or hydrazide can be hydrolyzed to the free C-terminal carboxyl moiety, and the protecting groups can be removed conventionally. The protecting group present on the N-terminal α-amino group may be removed either before, or after, the protected peptide is cleaved from the support. Purification of the peptides of the invention is typically achieved using chromatographic techniques, such as preparative HPLC (including reverse phase HPLC), gel permeation, ion exchange, partition chromatography, affinity chromatography (including monoclonal antibody columns), and the like, or other conventional techniques such as countercurrent distribution or the like.

Amino Acid Substitution and Addition Variants

Also included in this invention are peptides in which at least one amino acid residue and preferably, only one, has been removed and a different residue inserted in its place. For a detailed description of protein chemistry and structure, see Schulz, G. E. et al., *Principles of Protein Structure*, Springer-Verlag, New York, 1979, and Creighton, T. E., *Proteins: Structure and Molecular Principles*, W. H. Freeman & Co., San Francisco, 1984, which are hereby incorporated by reference. The types of substitutions which may be made in the peptide molecule of the present invention are conservative substitutions and are defined herein as exchanges within one of the following groups:

1. Small aliphatic, nonpolar or slightly polar residues: e.g., Ala, Ser, Thr, Gly;
2. Polar, negatively charged residues and their amides: e.g., Asp, Asn, Glu, Gln;
3. Polar, positively charged residues: e.g., His, Arg, Lys;

Pro, because of its unusual geometry, tightly constrains the chain. Substantial changes in functional properties are made by selecting substitutions that are less conservative, such as between, rather than within, the above groups (or two other amino acid groups not shown above), which will differ more significantly in their effect on maintaining (a) the structure of the peptide backbone in the area of the substitution (b) the charge or hydrophobicity of the molecule at the target site, or (c) the bulk of the side chain. Most substitutions according to the present invention are those which do not produce radical changes in the characteristics of the peptide molecule. Even when it is difficult to predict the exact effect of a substitution in advance of doing so, one skilled in the art will appreciate that the effect can be evaluated by routine screening assays, preferably the biological assays described below. Modifications of peptide properties including redox or thermal stability, hydrophobicity, susceptibility to proteolytic degradation or the tendency to aggregate with carriers or into multimers are assayed by methods well known to the ordinarily skilled artisan.

One group of preferred substitution variants of KPSSPPEE have the Glu at position 7 or 8 (or both) of SEQ ID NO:2 replaced by one or any two of Gln, Asp or Asn.

Other derivatives may further include substitution of the Ser at position 3 or 4 (or both) of SEQ ID NO:2 with one or any two of the following: Thr, Ala, Gly, hSer or ValβOH.

Furthermore, the Lys at position 1 of SEQ ID NO:2 may be replaced by His, Arg, Gln, Orn, Cit or Hci .

Other derivatives have Pro at position 2, 5 or 6 replaced by Hyp (hydroxyproline).

It is noteworthy that any and all combinations of the foregoing substitutions are within the scope of this invention.

Also included in this invention are addition variants wherein two or more residues are added to the C-terminus after Glu (or after any of its above substituents) in SEQ ID NO:2. These residues may be Leu-(Gly)$_n$, Ile-(Gly)$_n$, Val-(Gly)$_n$, Nva-(Gly)$_n$, or Nle-(Gly)$_n$, wherein Nva is norvaline, Nle is norleucine, and n=1–10.

Also included in this invention are addition variants wherein one or more residues is/are added to the N-terminus before Lys (or any of its above substituents) in SEQ ID NO:2. These residues may be Gly, Lys-(Gly)$_n$, Tyr-(Gly)$_n$, or Gly-(Gly)$_n$ wherein n=1–10.

Another preferred derivative of this invention is a 9-mer addition variant wherein any one of the following amino acids is added to the C-terminus after Glu (or any of its above substituents) in SEQ ID NO:2: Leu, Ile, Val, Nva, Nle, Met, Ala, or Gly.

In general, preferred peptide addition variants may have up to about 30 additional amino acids, more preferably about 20, most preferably 11. The functional limitations placed on the peptide variant, and the ease by which these activities can be tested using conventional means, would permit one skilled in the art to ascertain whether an addition (or any other type of) variant would affect the peptide's activity. In view of the structural description provided herein, it would be to determine whether a peptide variant falls within the scope of this invention.

Uncapped peptides of any of the foregoing sequences having free N- and C-termini, for example, uncapped NH$_2$-KPSSPPEE-OH [SEQ ID NO:2].

Chemical Derivatives

"Chemical derivatives" of KPSSPPEE [SEQ ID NO:2] contain additional chemical moieties not normally a part of the peptide. Covalent modifications of the peptide are included within the scope of this invention. Such modifications may be introduced into the molecule by reacting targeted amino acid residues of the peptide with an organic derivatizing agent that is capable of reacting with selected side chains or terminal residues.

The capped peptides discussed above are examples of preferred chemical derivatives of the "natural" uncapped peptide. Any of the above combination of substitution or addition variants may be capped with any of the capping groups disclosed herein.

Other examples of chemical derivatives of the peptide follow.

Lysinyl and amino terminal residues are derivatized with succinic or other carboxylic acid anhydrides. Derivatization with a cyclic carboxylic anhydride has the effect of reversing the charge of the lysinyl residues. Other suitable reagents for derivatizing α-amino-containing residues include imidoesters such as methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Carboxyl side groups, aspartyl or glutamyl, may be selectively modified by reaction with carbodiimides (R—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore, aspartyl and glutamyl residues can be converted to asparaginyl and glutaminyl residues by reaction with ammonia.

Other modifications include hydroxylation of proline and lysine, phosphorylation of hydroxyl groups of seryl or threonyl residues, methylation of the amino group of lysine (Creighton, supra, pp. 79–86 ), acetylation of the N-terminal amine, and amidation of the C-terminal carboxyl groups.

For every single peptide sequence disclosed herein, this invention includes the corresponding retro-inverso sequence wherein the direction of the peptide chain has been inverted and wherein all the amino acids belong to the D-series. For example the retro-inverso analogue of the natural L-series peptide KPSSPPEE is EEPPSSPK which is composed of D-series amino acids and in which E is the N-terminus and K is the C-terminus. For example the retro-inverso analogue of the natural L-series capped peptide Ac-KPSSPPEE-Am is Ac-EEPPSSPK-Am which is composed of D-series amino acids and in which the N-terminal E is acetylated and the C-terminal K is amidated. The complete range of N-terminal capping groups and the complete range C-terminal capping groups specified for the L-series peptides are also intended for the D-series peptides.

Also included are peptides wherein one or more D-amino acids has/have been substituted for one or more L-amino acids. Additionally, modified amino acids or chemical derivatives of amino acids may be provided such that the peptide contains additional chemical moieties or modified amino acids not normally a part of a natural protein. Such derivatized moieties may improve the solubility, absorption, biological half life, and the like. Moieties capable of mediating such effects are disclosed, for example, in *Remington's Pharmaceutical Sciences*, 16th ed., Mack Publishing Co., Easton, Pa. (1980).

Multimeric Peptides

The present invention also includes longer peptides in which the basic peptidic sequence of about 7–9 amino acids is repeated from about two to about 100 times, with or without intervening spacers or linkers. A multimer of the peptide KPSSPPEE is shown by the following formula (KPSSPPEE-$X_m$)$_n$-KPSSPPEE wherein m=0 or 1, n=1–100. X is a spacer group, preferably $C_1$–$C_{20}$ alkyl, $C_1$–$C_{20}$ alkenyl, $C_1$–$C_{20}$ alkynyl, $C_1$–$C_{20}$ polyether containing up to 9 oxygen atoms or $Gly_z$. (z=1–10).

It is understood that such multimers may be built from any of the peptide variants described herein. Moreover, a peptide multimer may comprise different combinations of peptide monomers, both KPSSPPEE and the disclosed variants thereof. Such oligomeric or multimeric peptides can be made by chemical synthesis or by recombinant DNA techniques as discussed herein. When produced chemically, the oligomers preferably have from 2–8 repeats of the basic peptide sequence. When produced recombinantly, the multimers may have as many repeats as the expression system permits, for example from two to about 100 repeats.

Peptidomimetics

A preferred type of chemical derivative of the peptides described herein is a peptidomimetic compound which mimics the biological effect of KPSSPPEE, capped or uncapped. A peptidomimetic agent may be an unnatural peptide or a non-peptide agent which has the stereochemical properties of KPSSPPEE, capped or uncapped, such that it has the binding activity or biological activity of KPSSPPEE, capped or uncapped. Hence, this invention includes compounds wherein a peptidomimetic compound is coupled to a peptide, for example,

X—PPEE wherein X is a peptidomimetic which mimics KPSS; the peptide portion may include a normal or a retro-inverso sequence.

Peptidomimetic compounds, either agonists, substrates or inhibitors, have been described for a number of bioactive peptides such as opioid peptides, VIP, thrombin, HIV protease, etc. Methods for designing and preparing peptidomimetic compounds are known in the art (Kempf D. J., *Methods Enzymol* 241:334–354 (1994); Hruby, V. J., *Biopolymers* 33:1073–82 (1993); Wiley, R. A. et al., *Med. Res. Rev.* 13:327–384 (1993); Claeson, G., *Blood Coagul. Fibrinolysis* 5:411–436 (1994), which references are incorporated by reference in their entirety). These methods are used to prepare capped or uncapped KPSSPPEE peptidomimetics which possess at least the binding capacity and specificity of the peptide and preferably also possess the biological activity. Knowledge of peptide chemistry and general organic chemistry available to those skilled in the art are sufficient for the design and testing of such compounds.

For example, such peptidomimetics may be identified by inspection of the cystallographically-derived three-dimensional structure of a peptide of the invention, for example KPSSPPEE, capped or uncapped, either free or bound in complex with its receptor(s). Alternatively, the structure of a peptide of the invention bound to its receptor(s) can be gained by the techniques of nuclear magnetic resonance spectroscopy. The better knowledge of the stereochemistry of the interaction of, say, KPSSPPEE, capped or uncapped, with its receptor will permit the rational design of such peptidomimetic agents.

All the foregoing peptides, variants and chemical derivatives including peptidomimetics and multimeric peptides must have the biological activity and/or the binding activity of KPSSPPEE as follows: at least about 20% of the activity of Ac-KPSSPPE-Am in an in vitro assay of cell invasiveness or an in vitro assay of endothelial tube formation and/or angiogenesis. These activities are characterized in greater detail below. Alternatively, or in addition, the peptide, variant or chemical derivatives should compete with labeled Ac-KPSSPPEE-Am for binding to a ligand or binding partner for Ac-KPSSPPEE-Am, whether this be a cellular receptor (tested in a binding assay with whole cells or fractions thereof), an isolated receptor or any other Ac-KPSSPPEE-Am-binding molecule.

Moreover, the peptides, variants or derivatives of the present invention do not have biological activities previously associated with urokinase plasminogen activator (uPA). That is they do no block the binding of uPA to the uPA receptor. These peptides lack thrombolytic activity, a hallmark of uPA.

Additional Discussion of Peptides, Variants and Peptidomimetics

Minor modifications of the amino acid sequence might affect activity if those modifications are selected purely at random. However, one skilled in the art of peptide and peptidomimetic design would follow a well-established set of "rules" in creating useful variants and derivatives. For example, it is expected that the KPSSPPEE peptide modified by replacing Ser with either Thr, Ala, or Gly possesses the level of activity disclosed above. According to Bowie et al. (*Science* 247:1306–1310, 1990), if a particular property of a side chain, such as charge or size, is important at a given position, only side chains that have the required property will be allowed. Conversely, if the chemical identity of the side chain is unimportant, then many different substitutions will be permitted. Studies based on these notions revealed that proteins are surprisingly tolerant of amino acid substitutions (Bowie et al., supra at page 1306). Thus the art recognizes and accepts certain types of changes in proteins and in peptides. Such acceptable modifications delineate a genus of peptides wherein each species predictably has the requisite type and/or level of activity.

Further, Bordo and Argos, *J. Mol. Biol.* 217:721–729 (1991), reported a statistical analysis of protein sequences and provided guidelines for "safe" amino acid substitutions in protein design, and by analogy, peptide design. It is axiomatic that proteins with similar functions are topographically similar at least in those regions responsible for activity. Based on the fact that the peptide KPSSPPEE contains 3 prolines out of 8 amino acids, the present inventors predicted that this peptide would have a single major conformer in solution, perhaps differing only in proline isomerization. This was also predicted by molecular dynamics simulations. Hence, KPSSPPEE would not be expected to assume multiple conformers in solution. The PP region of this peptide forms a specialized conformational motif known as a "proline turn" (or "bend"). The stiffness of this peptide (and its preliminary 3D structure) has been confirmed by 2D NMR.

In addition to applying this topographical criterion to the design and production of peptides with sequence homology or acceptable sequence substitutions, this criterion can be used as a basis for generating chemical derivatives of KPSSPPEE, including the peptidomimetics described above. This is fundamental to structure-based drug design and modeling. Although the solution structure of a free peptide may not exactly mimic its bound conformation, the solution structure does provide a starting scaffold for optimizing derivatives which mimic the peptide's activity. In fact, such scaffolds could not be derived in the absence of the basic topographical information about this peptide, either free or bound. If a derivative is prepared with a structure/topography similar to that of KPSSPPEE and the requisite biological and binding activity as disclosed herein, then it is within the scope of the present invention.

If a peptide or peptidomimetic is designed in accordance with this invention based on either the sequence or the topography (structure) of KPSSPPEE, and it has the bioactivity stated above, then it must be similar in conformation to KPSSPPEE and therefore falls within the scope of the invention. The assessment of activity in bioassays or binding assays such as those described herein is routine in the art and is the logical way to determine whether a compound is active. A useful substitution variant, addition variant or other chemical derivative of KPSSPPEE is a compound that has been designed based on the sequence or topographical structure of KPSSPPEE.

Systematic approaches in the art that allow the optimization of a peptide and development of peptidomimetics (Hruby et al., Biochem J. 268:249–262 (1990); and Hruby, 1993, supra) flow from a single starting point: the identification of a peptide lead compound. For example, the most preferred peptide lead compound of this invention is KPSSPPEE. The peptide and peptidomimetic design approaches disclosed herein and/or known in the art for generating an optimized compound are not possible without first identifying an active lead peptide, so that these designed peptides or peptidomimetics constitute a genus of compounds "around" the original peptide. Schemes for preparing active derivatives of the parent peptide have been described (e.g., Moore et al., Adv. Pharmacol. 33:91–141 (1995); Giannis and Rubsam, Adv. Drug Research 29:1–78 (1997)). Although each approach may require some experimentation, it is neither random nor undue. By following accepted schemes practiced by those skilled in the art, one can generate families of similarly acting compounds.

DIAGNOSTIC AND PROGNOSTIC COMPOSITIONS

Further, the peptides can be labeled for detection and used, for example, to detect a binding site for the peptide on the surface or in the interior of a cell. Thus, the fate of the peptide can be followed in vitro or in vivo by using the appropriate method to detect the label. The labeled peptide may also be utilized in vivo for diagnosis and prognosis, for example to image occult metastatic foci or for other types of in situ evaluations.

Example of suitable detectable labels are radioactive, fluorogenic, chromogenic, or other chemical labels. Useful radiolabels, which are detected by a gamma counter or a scintillation counter or by autoradiography include $^3H$, $^{125}I$, $^{131}I$, $^{35}S$ and $^{14}C$. In addition, 311I is also useful as a therapeutic isotope (see below).

Common fluorescent labels include fluorescein isothiocyanate, rhodamine, phycoerythrin, phycocyanin, allophycocyanin, o-phthaldehyde and fluorescamine.

The fluorophore, such as the dansyl group, must be excited by light of a particular wavelength to fluoresce. See, for example, Haugland, Handbook of Fluorescent Probes and Research Chemicals, Sixth Edition, Molecular Probes, Eugene, Oreg., 1996). In general, a fluorescent reagent is selected based on its ability to react readily with an amino function. Examples of such fluorescent probes include the Bodipy (4,4-difluoro-4-bora-3a,4a-diaza-s-indacene) fluorophores which span the visible spectrum (U.S. Pat. No. 4,774,339; U.S. Pat. No. 5,187,288; U.S. Pat. No. 5,248,782; U.S. Pat. No. 5,274,113; U.S. Pat. No. 5,433,896; U.S. Pat. No. 5,451,663). A preferred member of this group is 4,4-difluoro-5,7-dimethyl-4-bora-3a,4a-diaza-s-indacene-3-propionic acid.

Fluorescein, fluorescein derivatives and fluorescein-like molecules such as Oregon Green™ and its derivatives, Rhodamine Green™ and Rhodol Green™, are coupled to amine groups using the isocyanate, succinimidyl ester or dichlorotriazinyl-reactive groups. The long wavelength rhodamines, which are basically Rhodamine Green™ derivatives with substituents on the nitrogens, are among the most photostable fluorescent labeling reagents known. Their spectra are not affected by changes in pH between 4 and 10, an important advantage over the fluoresceins for many biological applications. This group includes the tetramethylrhodamines, X-rhodamines and Texas Red derivatives. Other preferred fluorophores for derivatizing the peptide according to this invention are those which are excited by ultraviolet light. Examples include cascade blue, coumarin derivatives, naphthalenes (of which dansyl chloride is a member), pyrenes and pyridyloxazole derivatives.

In yet another approach, one or more amino groups is allowed to react with reagents that yield fluorescent products, for example, fluorescamine, dialdehydes such as o-phthaldialdehyde, naphthalene-2,3-dicarboxylate and anthracene-2,3-dicarboxylate. 7-nitrobenz-2-oxa-1,3-diazole (NBD) derivatives, both chloride and fluoride, are useful to modify amines to yield fluorescent products.

Those skilled in the art will recognize that known fluorescent reagents modify groups other than amines, such as thiols, alcohols, aldehydes, ketones, carboxylic acids and amides. Hence, fluorescent substrates can readily be designed and synthesized using these other reactive groups.

The peptide can also be labeled for detection using fluorescence-emitting metals such as $^{152}Eu$, or others of the lanthanide series. These metals can be attached to the peptide using such metal chelating groups as diethylenetriaminepentaacetic acid (DTPA) or ethylenediaminetetraacetic acid (EDTA). The peptide can be made detectable by coupling it to a chemiluminescent compound. The presence of the chemiluminescent-tagged peptide is then determined by detecting the presence of luminescence that arises during the course of a chemical reaction. Examples of particularly useful chemiluminescers are luminol, isoluminol, theromatic acridinium ester, imidazole, acridinium salt and oxalate ester. Likewise, a bioluminescent compound may be used to label the peptide. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

In yet another embodiment, colorimetric detection is used, based on chromogenic compounds (chromophores) with high extinction coefficients.

In situ detection of the labeled peptide may be accomplished by removing a histological specimen from a subject and examining it by microscopy under appropriate conditions to detect the label. Those of ordinary skill will readily perceive that any of a wide variety of histological methods (such as staining procedures) can be modified in order to achieve such in situ detection.

The term "diagnostically labeled" means that the peptide has attached to it a diagnostically detectable label. There are many different labels and methods of labeling known to those of ordinary skill in the art. Examples of the types of labels which can be used in the present invention include radioactive isotopes, paramagnetic isotopes, and compounds which can be imaged by positron emission tomography (PET). Those of ordinary skill in the art will know of other suitable labels for binding to the peptides used in the invention, or will be able to ascertain such, by routine experimentation. Furthermore, the binding of these labels to the peptide or derivative can be done using standard techniques known to those of ordinary skill in the art.

For diagnostic in vivo radioimaging, the type of detection instrument available is a major factor in selecting a given radionuclide. The radionuclide chosen must have a type of decay which is detectable by a given type of instrument. In general, any conventional method for visualizing diagnostic imaging can be utilized in accordance with this invention. Another factor in selecting a radionuclide for in vivo diagnosis is that the half-life of a radionuclide be long enough so that it is still detectable at the time of maximum uptake by the target issue, but short enough so that deleterious radiation of the host is minimized. In one preferred embodiment, a radionuclide used for in vivo imaging does not emit particles, but produces a large number of photons in a 140–200 keV range, which may be readily detected by conventional gamma cameras.

For in vivo diagnosis, radionuclides may be bound to peptide either directly or indirectly by using an intermediary functional group. Intermediary functional groups that are often used to bind radioisotopes, which exist as metallic ions, to peptides are the chelating agents, DTPA and EDTA. Examples of metallic ions which can be bound to peptides are $^{99}Tc$, $^{123}I$, $^{111}In$, $^{131}I$, $^{97}Ru$, $^{67}Cu$, $^{67}Ga$, $^{125}I$, $^{68}Ga$, $^{72}As$, $^{89}Zr$, and $^{201}Tl$. Generally, the dosage of peptide labeled for detection for diagnostic use will vary depending on considerations such as age, condition, sex, and extent of disease in the patient, counterindications, if any, and other variables, to be adjusted by the individual physician. Dosage can vary from 0.01 mg/kg to 100 mg/kg.

In another embodiment, the peptides or derivatives of the present invention are used as affinity ligands for binding the peptide's receptor in assays, preparative affinity chromatography or solid phase separation. Such compositions may also be used to enrich, purify or isolate cells to which the peptide or derivative binds, preferably through a specific receptor-ligand interaction. The peptide or derivative is immobilized using common methods known in the art, e.g. binding to CNBr-activated Sepharose® or Agarose®, NHS-Agarose® or Sepharose®, epoxy-activated Sepharose® or Agarose®, EAH-Sepharose® or Agarose®, streptavidin-Sepharose® or Agarose® in conjunction with biotinylated peptide or derivatives. In general the peptides or derivatives of the invention may be immobilized by any other method which is capable of immobilizing these compounds to a solid phase for the indicated purposes. See, for example Affinity Chromatography: Principles and Methods (*Pharmacia LKB Biotechnology*). Thus, one embodiment is a composition comprising any of the peptides, derivatives or peptidomimetics described herein, bound to a solid support or a resin. The compound may be bound directly or via a spacer, preferably an aliphatic chain having about 2–12 carbon atoms.

By "solid phase" or "solid support" or "carrier" is intended any support or carrier capable of binding the peptide or derivative. Well-known supports, or carriers, in addition to Sepharose® or Agarose® described above are glass, polystyrene, polypropylene, polyethylene, dextran, nylon, amylases, natural and modified celluloses such as nitrocellulose, polyacrylamides, polyvinylidene difluoride, other agaroses, and magnetite, including magnetic beads. The carrier can be totally insoluble or partially soluble. The support material may have any possible structural configuration so long as the coupled molecule is capable of binding to receptor material. Thus, the support configuration may be spherical, as in a bead, or cylindrical, as in the inside surface of a test tube or microplate well, or the external surface of a rod. Alternatively, the surface may be flat such as a sheet, test strip, bottom surface of a microplate well, etc.

Antibodies and Their Uses

The present invention also provides antibodies specific for an epitope defined by the peptide sequence KPSSPPEE or specific for a chemical derivative thereof or a peptidomimetic thereof. Such antibodies may be polyclonal, monoclonal, bispecific, chimeric or antiidiotypic, and include antigen-binding fragments thereof. Any immunoassay known in the art may be used to detect the binding of such an antibody to a peptide, chemical derivative thereof or peptide oligomer according to this invention. Preferred assays are enzyme immunoassays or radioimmunoassay. The following references (incorporated by reference in their entirety) describe the production, purification, testing and use of antibodies: Hartlow, E. et al., *Antibodies: A Laboratory Manual*, Cold Spring Harbor Laboratory Press, Cold Spring Harbor, N.Y., 1988; Campbell, A., In: *Laboratory Techniques in Biochemistry and Molecular Biology*, Volume 13 (Burdon, R., et al., eds.), Elsevier, Amsterdam (1984)); Work, T. S. et al., *Laboratory Techniques and Biochemistry in Molecular Biology*, North Holland Publishing Company, NY, 1978; Weintraub, B., Principles of Radioimmunoassays, Seventh Training Course on Radioligand Assay Techniques, The Endocrine Society, March, 1986; Butler, J. E. (ed.), *Immunochemistry of Solid-Phase Immunoassay*, CRC Press, Boca Raton, 1991; Butler, J. E., In: *STRUCTURE OF ANTIGENS*, Vol. 1, Van Regenmortel, M., ed., CRC Press, Boca Raton 1992, pp. 209–259; Butler, J. E., In: van Oss, C. J. et al., (eds), *IMMUNOCHEMISTRY*, Marcel Dekker, Inc., New York, 1994, pp. 759–803; Voller, A. et al. (eds)., *Immunoassays for the 1980's*, University Park Press, Baltimore, 1981.

Antibodies of this invention are used to detect the presence of or measure the amount of the peptide epitope in a biological material or other sample by direct or competitive immunoassay. The antibodies can be coupled to a solid support and used in affinity chromatography to isolate and purify material containing the peptide epitope. Conversely, as described above, the peptide, variant or chemical derivative of this invention, bound to a solid support, is used to enrich or purify specific antibodies. Antiidiotypic antibodies can be used to gain a knowledge of the structure of a peptide, variant or chemical derivative of this invention when bound to a receptor for it.

Biological Assay of Anti-Invasive Activity

The compositions of the invention are tested for their anti-invasive capacity in a Matrigel® invasion assay system as described in detail by Kleinman et al., 1986 and Parish et al., 1992, which references are hereby incorporated by reference in their entirety. The assay is performed with a cell line, more preferably a tumor cell line, most preferably the rat breast cancer (Mat BIII) line or the human prostate cancer (PC-3) line (Xing and Rabbani, 1996; Hoosein et al., 1991).

Matrigel® is a reconstituted basement membrane containing type IV collagen, laminin, heparan sulfate proteoglycans such as perlecan, which bind to and localize bFGF, vitronectin as well as transforming growth factor-$\beta$ (TGF$\beta$), urokinase-type plasminogen activator (uPA), tissue plasminogen activator (tPA), and the serpin known as plasminogen activator inhibitor type 1 (PAI-1) (Chambers et al., 1995).

It is accepted in the art that results obtained in this assay for compounds which target extracellular receptors or enzymes are predictive of the efficacy of these compounds in vivo (Rabbani et aL, 1995).

Biological Assay of Anti-Angiogenic Activity

The compounds of this invention are tested for their anti-angiogenic activity in one of two different assay systems in vitro.

Endothelial cells, for example, human umbilical vein endothelial cells (HUVEC) or human microvascular endothelial cells (HMVEC) which can be prepared or obtained commercially, are mixed at a concentration of $2 \times 10^5$ cells/mL with fibrinogen (5 mg/mL in phosphate buffered saline (PBS) in a 1:1 (v/v) ratio. Thrombin is added (5 units/ mL final concentration) and the mixture is immediately transferred to a 24-well plate (0.5 mL per well). The fibrin gel is allowed to form and then VEGF and bFGF are added to the wells (each at 5 ng/mL final concentration) along with the test compound. The cells are incubated at 37° C. in 5% $CO_2$ for 4 days at which time the cells in each well are counted and classified as either rounded, elongated with no branches, elongated with one branch, or elongated with 2 or more branches. Results are expressed as the average of 5 different wells for each concentration of compound. Typically, in the presence of angiogenic inhibitors, cells remain either rounded or form undifferentiated tubes (e.g. 0 or 1 branch).

This assay is recognized in the art to be predictive of angiogenic (or anti-angiogenic) efficacy in vivo (Min et aL., 1996).

In an alternate assay, endothelial cell tube formation is observed when endothelial cells are cultured on Matrigel® (Schnaper et al., 1995). Endothelial cells ($1 \times 10^4$ cells/well) are transferred onto Matrigel®-coated 24-well plates, and tube formation is quantitated after 48 hrs. Inhibitors are tested by adding them either at the same time as the endothelial cells or at various time points thereafter.

This assay models angiogenesis by presenting to the endothelial cells a particular type of basement membrane, namely the layer of matrix which migrating and differentiating endothelial cells might be expected to first encounter. In addition to bound growth factors, the matrix components found in Matrigel® (and in basement membranes in situ) or proteolytic products thereof may also be stimulatory for endothelial cell tube formation which makes this model complementary to the fibrin gel angiogenesis model previously described (Blood and Zetter, 1990; Odedra and Weiss, 1991). The compounds of this invention inhibit endothelial cell tube formation in both assays, which suggests that the compounds will also have anti-angiogenic activity.

In Vivo Testing of Compositions in Animal Models of Human Tumors

The peptides, peptidomimetics and conjugates are tested for therapeutic efficacy in several well established rodent models which are considered to be highly representative of a broad spectrum of human tumors. The approaches are described in detail in Geran, R. I. et al., "Protocols for Screening Chemical Agents and Natural Products Against Animal Tumors and Other Biological Systems (Third Edition)", Canc. Chemother. Reports, Part 3, 3:1–112, which is hereby incorporated by reference in its entirety. All general test evaluation procedures, measurements and calculations are performed in accordance with this reference, including mean survival time, median survival time, calculation of approximate tumor weight from measurement of tumor diameters with vernier calipers; calculation of tumor diameters; calculation of mean tumor weight from individual excised tumors; and ratios between treated and control groups ratio for any measure (T/C ratios).

A. Rat Model of Tumor Progression

The effects of the compounds are tested on tumor progression in a rat syngeneic model of breast cancer (Xing and Rabbani, 1996). Mat BIII rat breast tumor cells ($1 \times 10^6$ cells in PBS, 0.1 mL per rat) are inoculated into the mammary fat pads of female Fisher rats. The test compound is dissolved in PBS (200 mM stock), sterile filtered and dispensed in vivo at a dose of up to about 100 mg/kg/day) using a 14-day Alza osmotic mini-pump implanted intraperitoneally at the time of inoculation. Control animals receive vehicle (PBS) alone. Animals are euthanized at day 14 and examined for metastasis in the spleen, lungs, liver, kidney and lymph nodes. In addition, the primary tumors are excised, quantitated, and prepared for immunohistochemistry.

B. 3LL Lewis Lung Carcinoma: Primary Tumor Growth

This tumor line arose spontaneously in 1951 as carcinoma of the lung in a C57BL/6 mouse (Cancer Res 15:39, 1955. See, also Malave, I. et al., J. Nat'l. Canc. Inst. 62:83–88 (1979)). It is propogated by passage in C57BL/6 mice by subcutaneous (sc) inoculation and is tested in semiallogeneic C57BL/6×DBA/2 $F_1$ mice or in allogeneic C3H mice. Typically six animals per group for subcutaneously (sc) implant, or ten for intramuscular (im) implant are used. Tumor may be implanted sc as a 2–4 mm fragment, or im or sc as an inoculum of suspended cells of about $0.5 - 2 \times 10^6$- cells. Treatment begins 24 hours after implant or is delayed until a tumor of specified size (usually approximately 400 mg) can be palpated. The test compound is administered ip daily for 11 days Animals are followed by weighing, palpation, and measurement of tumor size. Typical tumor weight in untreated control recipients on day 12 after im inoculation is 500–2500 mg. Typical median survival time is 18–28 days. A positive control compound, for example cyclophosphamide at 20 mg/kg/injection per day on days 1–11 is used. Results computed include mean animal weight, tumor size, tumor weight, survival time For confirmed therapeutic activity, the test composition should be tested in two multidose assays.

C. 3LL Lewis Lung Carcinoma: Primary Growth and Metastasis Model

This model has been utilized by a number of investigators. See, for example, Gorelik, E. et al., J. Nat'l. Canc. Inst. 65:1257–1264 (1980); Gorelik, E. et al., Rec. Results Canc. Res. 75:20–28 (1980); Isakov, N. et al., Invasion Metas.

2:12–32 (1982); Talmadge J. E. et al., *J. Nat'l. Canc. Inst.* 69:975–980 (1982); Hilgard, P. et al., *Br. J. Cancer* 35:78–86(1977)). Test mice are male C57BL/6 mice, 2–3 months old. Following sc, im, or intra-footpad implantation, this tumor produces metastases, preferentially in the lungs. With some lines of the tumor, the primary tumor exerts anti-metastatic effects and must first be excised before study of the metastatic phase (see also U.S. Pat. No. 5,639,725).

Single-cell suspensions are prepared from solid tumors by treating minced tumor tissue with a solution of 0.3% trypsin. Cells are washed 3 times with PBS (pH 7.4) and suspended in PBS. Viability of the 3LL cells prepared in this way is generally about 95–99% (by trypan blue dye exclusion). Viable tumor cells ($3\times10^4$–$5\times10^6$) suspended in 0.05 ml PBS are injected subcutaneously, either in the dorsal region or into one hind foot pad of C57BL/6 mice. Visible tumors appear after 3–4 days after dorsal sc injection of $10^6$ cells. The day of tumor appearance and the diameters of established tumors are measured by caliper every two days.

The treatment is given as one or two doses of peptide or derivative, per week. In another embodiment, the peptide is delivered by osmotic minipump.

In experiments involving tumor excision of dorsal tumors, when tumors reach about 1500 mm$^3$ in size, mice are randomized into two groups: (1) primary tumor is completely excised; or (2) sham surgery is performed and the tumor is left intact. Although tumors from 500–3000 MM$^3$ inhibit growth of metastases, 1500 mm$^3$ is the largest size primary tumor that can be safely resected with high survival and without local regrowth. After 21 days, all mice are sacrificed and autopsied.

Lungs are removed and weighed. Lungs are fixed in Bouin's solution and the number of visible metastases is recorded. The diameters of the metastases are also measured using a binocular stereoscope equipped with a micrometer-containing ocular under 8× magnification. On the basis of the recorded diameters, it is possible to calculate the volume of each metastasis. To determine the total volume of metastases per lung, the mean number of visible metastases is multiplied by the mean volume of metastases. To further determine metastatic growth, it is possible to measure incorporation of $^{125}$IdUrd into lung cells (Thakur, M. L. et al., *J. Lab. Clin. Med.* 89:217–228 (1977). Ten days following tumor amputation, 25 μg of fluorodeoxyuridine is inoculated into the peritoneums of tumor-bearing (and, if used, tumor-resected mice). After 30 min, mice are given 1 μCi of $^{125}$IdUrd (iododeoxyuridine). One day later, lungs and spleens are removed and weighed, and a degree of $^{125}$IdUrd incorporation is measured using a gamma counter.

In mice with footpad tumors, when tumors reach about 8–10 mm in diameter, mice are randomized into two groups: (1) legs with tumors are amputated after ligation above the knee joints; or (2) mice are left intact as nonamputated tumor-bearing controls. (Amputation of a tumor-free leg in a tumor-bearing mouse has no known effect on subsequent metastasis, ruling out possible effects of anesthesia, stress or surgery). Mice are killed 10–14 days after amputation. Metastases are evaluated as described above.

Statistics: Values representing the incidence of metastases and their growth in the lungs of tumor-bearing mice are not normally distributed. Therefore, non-parametric statistics such as the Mann-Whitney U-Test may be used for analysis.

Study of this model by Gorelik et al. (1980, supra) showed that the size of the tumor cell inoculum determined the extent of metastatic growth. The rate of metastasis in the lungs of operated mice was different from primary tumor-bearing mice. Thus in the lungs of mice in which the primary tumor had been induced by inoculation of larger doses of 3LL cells (1–$5\times10^6$) followed by surgical removal, the number of metastases was lower than that in nonoperated tumor-bearing mice, though the volume of metastases was higher than in the nonoperated controls. Using $^{125}$IdUrd incorporation as a measure of lung metastasis, no significant differences were found between the lungs of tumor-excised mice and tumor-bearing mice originally inoculated with $1\times10^6$ 3LL cells. Amputation of tumors produced following inoculation of $1\times10^5$ tumor cells dramatically accelerated metastatic growth. These results were in accord with the survival of mice after excision of local tumors. The phenomenon of acceleration of metastatic growth following excision of local tumors had been repeatedly observed (for example, see U.S. Pat. No. 5,639,725). These observations have implications for the prognosis of patients who undergo cancer surgery.

D. Experimental Metastasis Models

The compounds of this invention are also tested for inhibition of late metastasis using an experimental metastasis model (Crowley et al., 1993). Late metastasis involves the steps of attachment and extravasation of tumor cells, local invasion, seeding, proliferation and angiogenesis.

Human prostatic carcinoma cells (PC-3) transfected with a reporter gene, preferably the green fluorescent protein (GFP) gene, but as an alternative with a gene encoding the enzymes chloramphenicol acetyl-transferase (CAT), luciferase or LacZ. This permits utilization of either of these markers (fluorescence detection of GFP or histochemical calorimetric detection of enzymatic activity) for following the fate of these cells. Cells are injected, preferably iv, and metastases identified after about 14 days, particularly in the lungs but also in regional lymph nodes, femurs and brain. This mimics the organ tropism of naturally occurring metastases of prostate cancer. For example, GFP-expressing PC-3 cells ($1\times10^6$ cells per mouse) are injected iv into the tail veins of nude (nu/nu) mice. Animals are also implanted with mini-pumps (sub-dermally on the back) dispensing either the test compound (at least about 100 mg/kg/day) or vehicle. The animals are euthanized after 14 days and their organs prepared for histological examination. Single metastatic cells and foci are visualized and quantitated by fluorescence microscopy or light microscopic histochemistry or by grinding the tissue and quantitative calorimetric assay of the detectable label.

For a compound to be useful in accordance with this invention, it should demonstrate anti-tumor activity in the above models, for example, blocking tumor progression, angiogenesis and/or metastasis.

Angiogenesis

Angiogenesis is measured by determining microvessel density using immunostaining for CD31 (also known as platelet-endothelial cell adhesion molecule or PECAM). Results are reported as the average microvessel density of 5 fields each from 5 different sections (Penfold et al., 1996). Typically, the whole tumor is excised, sectioned and the sections examined histologically for microvessel density using appropriate stains or labels for other markers.

Pharmaceutical and Therapeutic Compositions and Their Administration

The compounds that may be employed in the pharmaceutical compositions of the invention include all of those compounds described above, as well as the pharmaceutically acceptable salts of these compounds. Pharmaceutically acceptable acid addition salts of the compounds of the invention containing a basic group are formed where appropriate with strong or moderately strong, non-toxic, organic or inorganic acids in the presence of a basic amine by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Pharmaceutically acceptable base addition salts of compounds of the invention containing an acidic group are prepared by known methods from organic and inorganic bases and include, for example, nontoxic alkali metal and alkaline earth bases, such as calcium, sodium, potassium and ammonium hydroxide; and nontoxic organic bases such as triethylamine, butylamine, piperazine, and tri(hydroxymethyl)methylamine.

As stated above, the compounds of the invention possess the ability to inhibit invasiveness or angiogenesis, properties that are exploited in the treatment of cancer, in particular metastatic cancer. A composition of this invention may be active per se, or may act as a "pro-drug" that is converted in vivo to the active form.

The compounds of the invention, as well as the pharmaceutically acceptable salts thereof, may be incorporated into convenient dosage forms, such as capsules, impregnated wafers, tablets or injectable preparations. Solid or liquid pharmaceutically acceptable carriers may be employed.

Preferably, the compounds of the invention are administered systemically, e.g., by injection. When used, injection may be by any known route, preferably intravenous, subcutaneous, intramuscular, intracranial or intraperitoneal. Injectables can be prepared in conventional forms, either as solutions or suspensions, solid forms suitable for solution or suspension in liquid prior to injection, or as emulsions.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in *Remington's Pharmaceutical Sciences*, Mack Publishing Company, Easton Pa. (Gennaro 18th ed. 1990).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral, parenteral, topical, transdermal, intravaginal, intranasal, intrabronchial, intracranial, intraocular, intraaural and rectal administration. The pharmaceutical compositions may also contain minor amounts of nontoxic auxiliary substances such as wetting or emulsifying agents, pH buffering agents and so forth.

Though the preferred routes of administration are systemic the pharmaceutical composition may be administered topically or transdermally, e.g., as an ointment, cream or gel; orally; rectally; e.g., as a suppository, parenterally, by injection or continuously by infusion; intravaginally; intranasally; intrabronchially; intracranially intra-aurally; or intraocularly.

For topical application, the compound may be incorporated into topically applied vehicles such as a salve or ointment. The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000); conventional creams such as HEB cream; gels; as well as petroleum jelly and the like.

Also suitable for topic application are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the compounds of the invention.

For the preferred topical applications, especially for humans, it is preferred to administer an effective amount of the compound to an infected area, e.g., skin surface, mucous membrane, eyes, etc. This amount will generally range from about 0.001 mg to about 1 g per application, depending upon the area to be treated, the severity of the symptoms, and the nature of the topical vehicle employed.

The compositions of the invention may further comprise one or more additional compounds that are anti-tumor agents, such as mitotic inhibitors, e.g., vinblastine; alkylating agents, e.g., cyclophosphamide; folate inhibitors, e.g., methotrexate, piritrexim or trimetrexate; antimetabolites, e.g., 5-fluorouracil and cytosine arabinoside; intercalating antibiotics, e.g., adriamycin and bleomycin; enzymes or enzyme inhibitors, e.g., asparaginase; topoisomerase inhibitors, e.g., etoposide; or biological response modifiers, e.g., interferon. In fact, pharmaceutical compositions comprising any known cancer therapeutic in combination with the peptides disclosed herein are within the scope of this invention.

The composition of the invention may also comprise one or more other medicaments, preferably anti-infectives such as antibacterial, anti-fungal, anti-parasitic, anti-viral, and anti-coccidial agents. Exemplary antibacterial agents include, for example, sulfonamides such as sulfamethoxazole, sulfadiazine or sulfadoxine; DHFR inhibitors such as trimethoprim, bromodiaprim or trimetrexate; penicillins; cephalosporins; aminoglycosides; bacteriostatic inhibitors of protein synthesis; the quinolonecarboxylic acids and their fused isothiazole analogs; and the like.

Other Therapeutic Compositions

In another embodiment, the compounds of this invention are "therapeutically conjugated" and used to deliver a therapeutic agent to the site of where the compounds home and bind, such as sites of tumor metastasis or foci of infection/inflammation. The term "therapeutically conjugated" means that the compound, preferably a peptide, peptide derivative, or peptidomimetic, is conjugated to a therapeutic agent. The therapeutic agents used in this manner act are directed either to the underlying cause or the components of the processes of tumor invasion, angiogenesis or inflammation. Examples of agents used to treat inflammation are the steroidal and non-steroidal anti-inflammatory drugs, many of which inhibit prostaglandin synthesis.

Other therapeutic agents which can be coupled to the compounds according to the method of the invention are drugs, radioisotopes, lectins and other toxins. The therapeutic dosage administered is an amount which is therapeutically effective, and will be known to one of skill in the art. The dose is also dependent upon the age, health, and weight of the recipient, kind of concurrent treatment, if any, frequency of treatment, and the nature of the effect desired, such as, for example, anti-inflammatory effects or anti-bacterial effect.

Lectins are proteins, commonly derived from plants, that bind to carbohydrates. Among other activities, some lectins are toxic. Some of the most cytotoxic substances known are protein toxins of bacterial and plant origin (Frankel, A. E. et al., *Ann. Rev. Med.* 37:125–142 (1986)). These molecules binding the cell surface and inhibition cellular protein synthesis. The most commonly used plant toxins are ricin and abrin; the most commonly used bacterial toxins are diphtheria toxin and Pseudomonas exotoxin A. In ricin and abrin, the binding and toxic functions are contained in two separate protein subunits, the A and B chains. The ricin B chain binds to the cell surface carbohydrates and promotes the uptake of the A chain into the cell. Once inside the cell, the ricin A chain inhibits protein synthesis by inactivating the 60S subunit of the eukaryotic ribosome Endo, Y. et al., *J. Biol. Chem.* 262: 5908–5912 (1987)). Other plant derived toxins, which are single chain ribosomal inhibitory proteins, include pokeweed antiviral protein, wheat germ protein, gelonin, dianthins, momorcharins, trichosanthin, and many others (Strip, F. et al., *FEBS Lett.* 195:1–8 (1986)). Diphtheria toxin and Pseudomonas exotoxin A are also single chain proteins, and their binding and toxicity functions reside in separate domains of the same protein chain with full toxin activity requiring proteolytic cleavage between the two domains. Pseudomonas exotoxin A has the same catalytic activity as diphtheria toxin. Ricin has been used therapeutically by binding its toxic α-chain, to targeting molecules such as antibodies to enable site-specific delivery of the toxic effect. Bacterial toxins have also been used as anti-tumor conjugates. As intended herein, a toxic peptide chain or domain is bound to a compound of this invention and delivered in a site-specific manner to a target site where the toxic activity is desired, such as a metastatic focus. Conjugation of toxins to protein such as antibodies or other ligands are known in the art (Olsnes, S. et al., *Immunol. Today* 10:291–295 (1989); Vitetta, E. S. et al., *Ann. Rev. Immunol.* 3:197–212 (1985)).

Examples of therapeutic radioisotopes which can be bound to the compound for use in accordance with according the methods of the invention, are $^{125}$I, $^{131}$I, $^{90}$Y, $^{67}$Cu, $^{217}$Bi, $^{211}$At $^{212}$Pb, $^{47}$Sc, and $^{109}$Pd.

Cytotoxic drugs that interfere with critical cellular processes including DNA, RNA, and protein synthesis, have been conjugated to antibodies and subsequently used for in vivo therapy. Such drugs, including but are not limited to daunorubicin, doxorubicin, methotrexate, and Mitomycin C are also coupled to the compounds of this invention and use therapeutically in this form.

Therapeutic Methods

This invention includes methods for inhibiting cellular invasion, chiefly by tumor cells, or angiogenesis, primarily induced by tumor cells in a subject. By inhibiting invasion by cells or angiogenesis, the method results in inhibition of tumor metastasis. In this method, a vertebrate subject, preferably a mammal, more preferably a human, is administered an amount of the compound effective to inhibit invasion or angiogenesis. The compound or pharmaceutically acceptable salt thereof is preferably administered in the form of a pharmaceutical composition as described above.

Doses of the compounds preferably include pharmaceutical dosage units comprising an effective amount of the peptide. By an effective amount is meant an amount sufficient to achieve a steady state concentration in vivo which results in a measurable reduction in any relevant parameter of disease and may include growth of primary or metastatic tumor, any accepted index of inflammatory reactivity, or a measurable prolongation of disease-free interval or of survival. For example, a reduction in tumor growth in 20 % of patients is considered efficacious (Frei III, E., *The Cancer-Journal* 3:127–136 (1997)). However, an effect of this magnitude is not considered to be a minimal requirement for the dose to be effective in accordance with this invention.

In one embodiment, an effective dose is at least equal to, preferably 10-fold and more preferably 100-fold higher than the 50% inhibitory concentration ($IC_{50}$) of the compound in an in vivo assay as described herein.

The amount of active compound to be administered depends on the precise peptide or derivative selected, the disease or condition, the route of administration, the health and weight of the recipient, the existence of other concurrent treatment, if any, the frequency of treatment, the nature of the effect desired, for example, inhibition of tumor metastasis, and the judgment of the skilled practitioner.

A preferred dose for treating a subject, preferably mammalian, more preferably human, with a tumor is an amount of up to about 100 milligrams of active compound per kilogram of body weight.

Typical single dosages of the peptide are between about 1 μg and about 100 mg/kg body weight. For topical administration, dosages in the range of about 0.01–20% concentration of the compound, preferably 1–5%, are suggested. A total daily dosage in the range of about 10 milligrams to about 7 grams is preferred for oral administration. The foregoing ranges are, however, suggestive, as the number of variables in regard to an individual treatment regime is large, and considerable excursions from these recommended values are expected.

An effective amount or dose of the peptide for inhibiting invasion in vitro is in the range of about 1 picogram to about 0.5 nanograms per cell. Effective doses and optimal dose ranges may be determined in vitro using the methods described herein.

The compounds of the invention may be further characterized as producing an inhibitory effect on cell migration and invasion, on angiogenesis, on tumor metastasis or on inflammatory reactions. The compounds are especially useful in producing an anti-tumor effect in a mammalian host, preferably human, harboring a tumor.

The foregoing compositions and treatment methods are useful for inhibiting cell migration and invasion or migration-induced cell proliferation in a subject having a disease or condition associated with undesired cell invasion, migration-induced proliferation, angiogenesis or metastasis. Such diseases or conditions may include primary growth or solid tumors or leukemias and lymphomas, metastasis, invasion and/or growth of tumor metastases, atherosclerosis, myocardial angiogenesis, post-balloon angioplasty vascular restenosis, neointima formation following vascular trauma, vascular graft restenosis, coronary collateral formation, deep venous thrombosis, ischemic limb angiogenesis, telangiectasia, pyogenic granuloma, corneal diseases, rubeosis, neovascular glaucoma, diabetic and other retinopathy, retrolental fibroplasia, diabetic neovascularization, macular degeneration, endometriosis, arthritis, fibrosis associated with chronic inflammatory conditions including psoriasis scleroderma, lung fibrosis, chemotherapy-induced fibrosis, wound healing with scarring and fibrosis; peptic ulcers, fractures, keloids, and disorders of vasculogenesis, hematopoiesis, ovulation, menstruation, pregnancy and placentation, or any other disease or condition in which invasion or angiogenesis is pathogenic.

Having now generally described the invention, the same will be more readily understood through reference to the following examples which are provided by way of illustration, and are not intended to be limiting of the present invention, unless specified.

EXAMPLE I

Synthesis of Acetyl-Lys-Pro-Ser-Ser-Pro-Pro-Glu-Glu-NH$_2$

The starting material was p-methyl-benzhydrylamine resin substituted at a level of 0.70 mEq per gram of resin. Each of the L-amino acids, starting with glutamic acid, was added in sequence in a synthesis cycle consisting of the three steps of TFA deprotection, coupling and capping. The completed peptide was subjected to HF cleavage and then purified.

1. TFA De-protection

The starting resin was conditioned before adding the first glutamic acid, or, in the case of subsequent cycles, the BOC protecting group was removed from the α-amino nitrogen of the starting material by treating the resin with 50% trifluoroacetic acid (TFA) in dichloromethane (DCM) (two to three volumes per resin volume). The mixture was stirred at room temperature for 30 minutes and then drained. The resin was then washed once with an equal volume of isopropanol for one minute and washed twice with an equal volume of methanol, each wash taking one minute.

2. Coupling

The de-protected resin was washed twice with an equal volume of 10% triethylamine in DCM, each wash taking one minute, and washed twice with an equal volume of methanol, each wash taking one minute, and washed twice with an equal volume of DCM, each wash taking one minute. A BOC-protected amino acid (three equivalents, dissolved in DCM or in a mixture of DCM and N,N'-dimethylformamide (DMF)) and 1-hydroxybenzotriazole (1M solution in DMF, three equivalents) was added to the resin, and the mixture was stirred for a few seconds. Dicyclohexylcarbodiimide (DCC) (1M solution in DCM, three equivalents) was then added, and the whole mixture was stirred for 60–120 minutes. The resin was washed twice with an equal volume of methanol and then washed twice with an equal volume of DCM. A small sample was taken for a ninhydrin test to assess the completeness of coupling. Generally, if incomplete, the coupling step 2 is repeated. If complete, the synthesis is continued with the capping step 3.

All amino acids were used as α-BOC derivatives. Side chain protecting groups were as follows:

| Amino acid | Protecting group |
| --- | --- |
| Histidine | Benzyloxymethyl |
| Asparagine | Xanthyl |
| Glutamine | Xanthyl |
| Serine | O-benzyl |
| Threonine | O-benzyl |

-continued

| Amino acid | Protecting group |
| --- | --- |
| Tyrosine | 2-Bromo-Z |
| Lysine | 2-Chloro-Z |
| Glutamic acid | Cyclohexyl |
| Aspartic acid | Cyclohexyl |

3. Capping

The resin was stirred with an equal volume of acetic anhydride (20% solution in DCM) for 5 minutes at room temperature. The resin was washed twice with an equal volume of methanol and then washed twice with an equal volume of DCM.

4. HF Cleavage

The resin bearing the desired amino acid sequence (1.0 gram) was placed in a Teflon reaction vessel, and anhydrous anisole (1 mL) was added. The vessel was cooled with liquid N$_2$, and anhydrous HF (10 mL) was distilled into it. The temperature was raised with ice water to 0° C. The mixture was stirred at this temperature for one hour, and then the HF was distilled off at 0° C. The residue was washed with anhydrous ether, and the peptide was extracted with a 1:1 mixture of CH$_3$CN:H$_2$O.

5. Purification

The lyophilized powder was dissolved in 0.1% TFA buffer and loaded onto a Waters C18 preparative column (2 inches diameter, 15–20 μm particle size, 300 Å pore size). The loaded column was eluted with a two-component eluent applied as a linear gradient, starting with 0% of solution A in solution B and finishing with 40% of solution A in solution B. Solution A was 0.1% TFA in H$_2$O, and solution B was 0.1% TFA in CH$_3$CN. Fractions exhibiting purity equal to or better than that desired were pooled and lyophilized to render the purified final product as the trifluoroacetate salt.

EXAMPLE II

Anti-Invasive and Anti-Proliferative Activity of Capped KPSSPPEE (Å6) and Related Peptides Several peptides were tested for anti-invasive capacity in a Matrigel® invasion assay system as indicated above (Kleinman et al., supra; Parish et al., supra). Several invasive human tumor lines (PC-3, MDA-MB-231) and non-human tumors (3LL, Mat B-III) were examined. The rat breast cancer line Mat B III and the human prostate cancer line PC-3 were initially used.

Tumor cells ($5\times10^5$/mL, in a volume of 200 μL) in serum-free RPMI 1640 medium were added to a disposable transwell invasion chamber coated with Matrigel® (Becton Dickinson, Lincoln Park, N.J.). The invasion chambers were placed in 24-well tissue culture plates filled with serum-free RPMI-1640 and the plates were placed in an atmosphere of 5% CO$_2$ in humidified air at 37° C. for 48–72 hours. The chambers were then removed, inverted, and the cells which had invaded (and now appeared on the bottom face of the invasion chamber) were fixed and stained using Diff-Quick® (Scientific Products). Cells were counted in 10 different fields on each filter and an average obtained. Typically, 3–5 replicates were performed at each concentration of compound tested.

Figure 7:
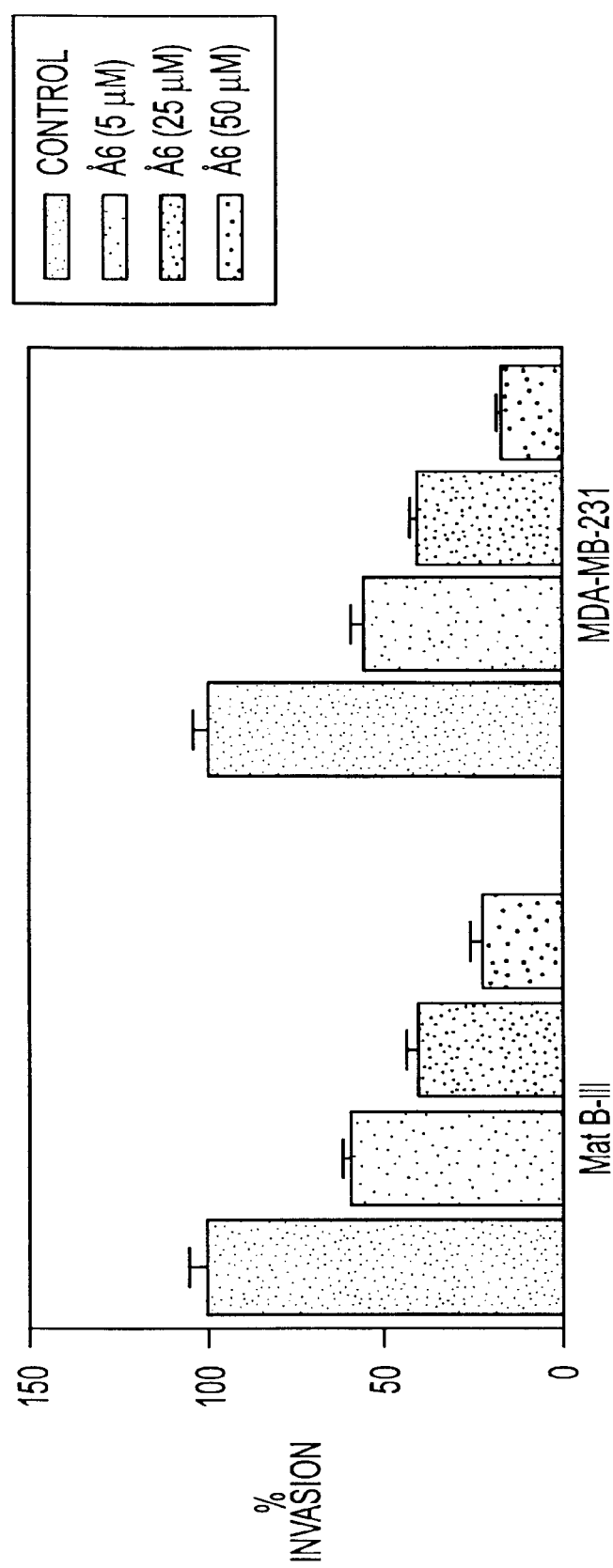
FIG. 7 shows that Å6 inhibits the invasion of Mat B-III rate breast cancer cells and MDA-MB-231 human breast cancer cells through Matrigel®.

The invasion of all the cell lines tested thus far has been inhibited by Å6. FIG. 1 shows that Ac-KPSSPPEE-Am inhibited the invasion of both rat and human prostate cancer line PC-3 and rat breast cancer line Mat B III. Typical results with both MDA-MB-231 and Mat B-III cells are presented in FIG. 7.

This peptide was not cytotoxic to the cells nor did it inhibit cell proliferation. Thus the observed effect was not a side effect of cytotoxicity and could be ascribed to a mechanism of action distinct from that of cytotoxic or cytostatic agents.

Tests were also conducted on shorter related, capped peptides having the sequence Ac-PSSPPEE-Am (a deletion variant of SEQ ID NO:2 which lacks the N-terminal Lys) and Ac-KPSSPPE-Am (a deletion variant of SEQ ID NO:2 lacking one of the C-terminal Glu residues). Also tested was a similar longer peptide, KPSSPPEELK [SEQ ID NO: 1] (Blasi et al., U.S. Pat. No. 5,416,006) and its capped counterpart, Ac-KPSSPPEELK-Am).

Figure 8:
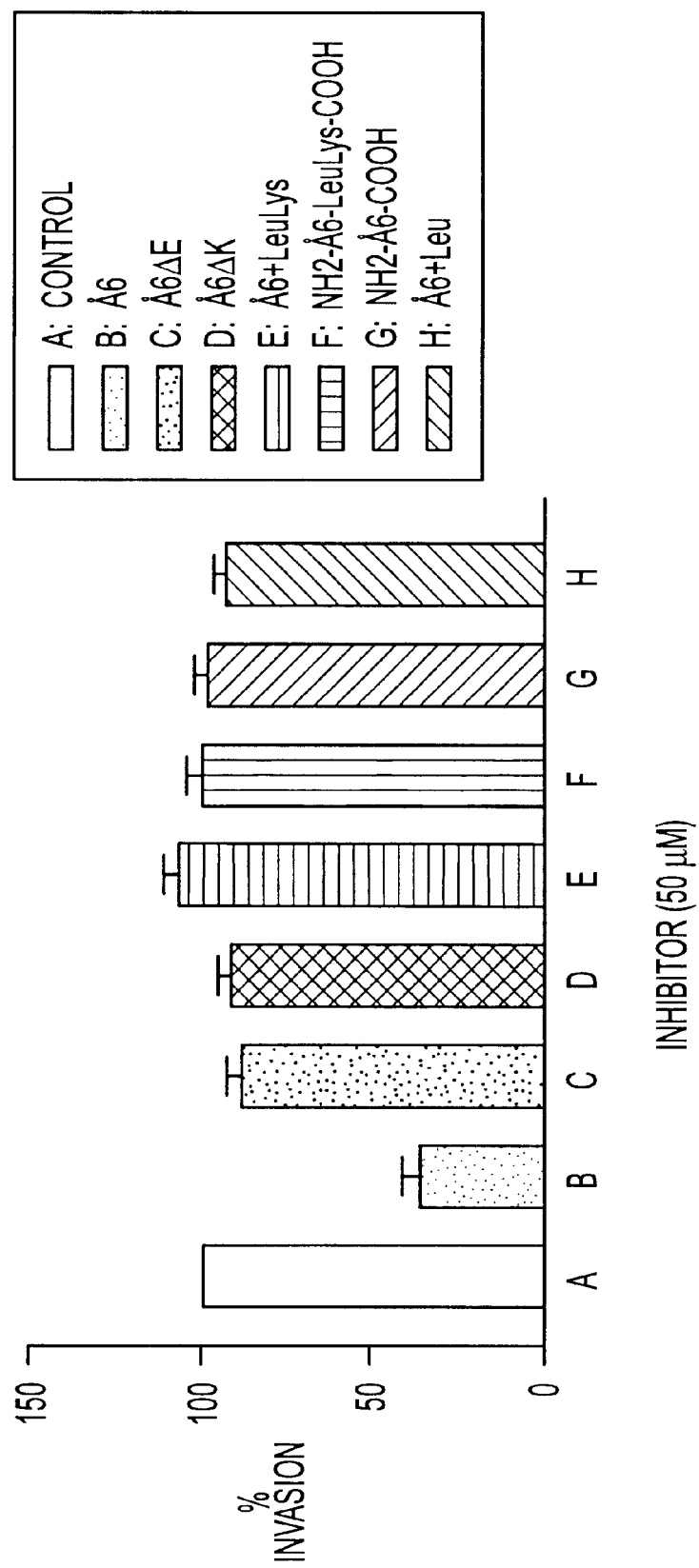
FIG. 8 shows the inhibition of Mat B-III invasion by Å6 and its variants. A: Control (no compound); B: Å6; C: Å6 lacking the C-terminal Glu; D: Å6 lacking the N-terminal Lys; E: Å6 extended by LeuLys at the C-terminus (corresponds to amino acids 144 and 145 in uPA); F: same as E except C-terminal is not capped; G: Å6, N and C termini uncapped; H: Å6 extended by Leu at C-terminus (capped).

To identify the minimal sequence required for activity as well as to assess the role of the capping group for activity, Å6 and variants of Å6 were tested for their ability to inhibit Mat B-III invasion through Matrigel® (FIG. 8). Å6 was found to be optimal.

Figure 2:
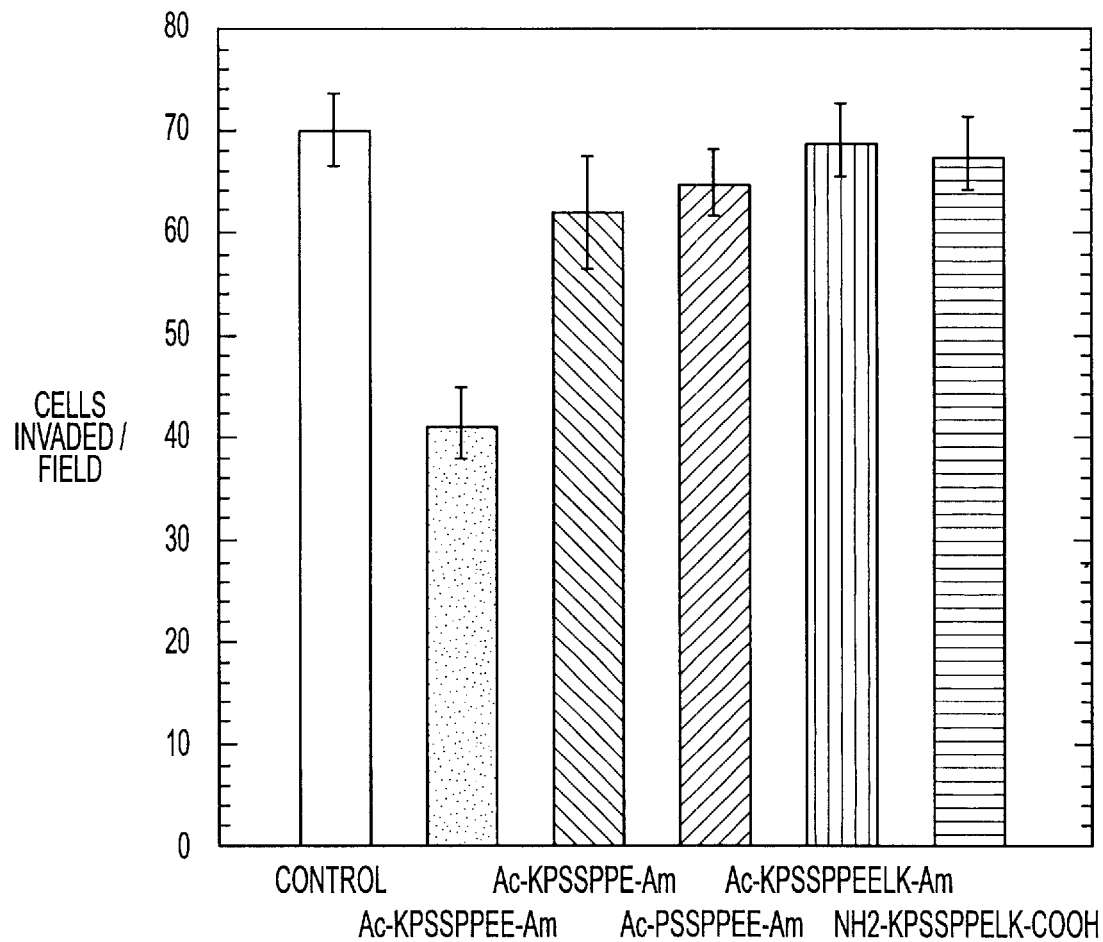
FIG. 2 is a graph showing the effect of various peptides on the in vitro invasion of PC-3 cells in a Matrigel® system as described in the Examples. All compounds were tested at a 5 μM. The following peptides were examined: Ac-Lys-Pro-Ser-Ser-Pro-Pro-Glu-Glu-Am (Ac-KPSSPPEE-Am) [SEQ ID NO:2] and the following variants of SEQ ID NO:2: Ac-Lys-Pro-Ser-Ser-Pro-Pro-Glu-Am (Ac-KPSSPPE-Am), Ac-Pro-Ser-Ser-Pro-Pro-Glu-Glu-Am (Ac-PSSPPEE-Am) as well as SEQ ID NO:1 (Lys-Pro-Ser-Ser-Pro-Pro-Glu-Glu-Leu-Lys) either capped (Ac-KPSSPPEELK-Am) or uncapped (KPSSPPEELK).

It is noteworthy that all the peptides other than Ac-KPSSPPEE-Am showed little or no activity in this assay, indicating that SEQ ID NO: 2 was the minimal required size for activity (FIG. 2). The results also indicated that addition of Leu and Lys at the C terminus of KPSSPPEE abrogated its biological activity, regardless of whether the termini were capped or uncapped.

The anti-invasive and anti-migratory properties prompted the inventors to test whether Å6 inhibited the matrix metalloproteinases MMP2 and MMP9. HT1080 cells were grown in the presence of dexamethasone for 24 hrs and the supernatant collected and treated with phenylmercuric acetate to activate proMMPs. MMP activity was measured using the EnzCheck gelatinase assay (Molecular Probes). Å6 did not inhibit gelatinase activity at concentrations up to 100 μM.

Å6 was also tested for its ability to inhibit the proliferation of cells other than endothelial cells in vitro. No antiproliferative effects were observed when Å6 was tested against U87, MDA-MB-231, Mat B-III, HeLa, CHO, HepG2 or SMC (aortic smooth muscle cells). Further, Å6 did not potentiate the anti-proliferative activity of CDDP against U87 cells.

EXAMPLE III

Inhibition of Plasminozen Activation

Single chain uPA (scuPA) complexed with a soluble form (suPAR) of the uPA receptor (uPAR) is able to activate plasminogen as efficiently as uPA, in the absence of activation by plasmin (Higazi A. A. R. et al., (1995) *J Biol Chem* 270: 17375–17380). scuPA remains as a single chain molecule, yet complex formation with suPAR induces a conformational change in scuPA, such that an active site capable of activating plasminogen was formed. This scuPA-suPAR complex mimics the scuPA-uPAR complex formed on the cell surface and activation of plasminogen by scuPA bound to cell-surface uPAR has indeed been demonstrated (Manchanda N. et al., (1991) *J Biol Chem*. 266:12752–12758). In addition, the scuPA-suPAR complex has been demonstrated to mediate clot lysis (fibrin turnover) in vitro and was more efficient in this assay than uPA alone. The scuPA-uPAR (or scuPA-suPAR) complex is very resistant to inhibition by endogenous uPA inhibitors (PAIs) (Higazi, A R, Mazar A et al. (1996) *Blood* 87:3545–3549), in contrast to uPA, which is rapidly quenched in the presence of PAIs.

Figure 3:
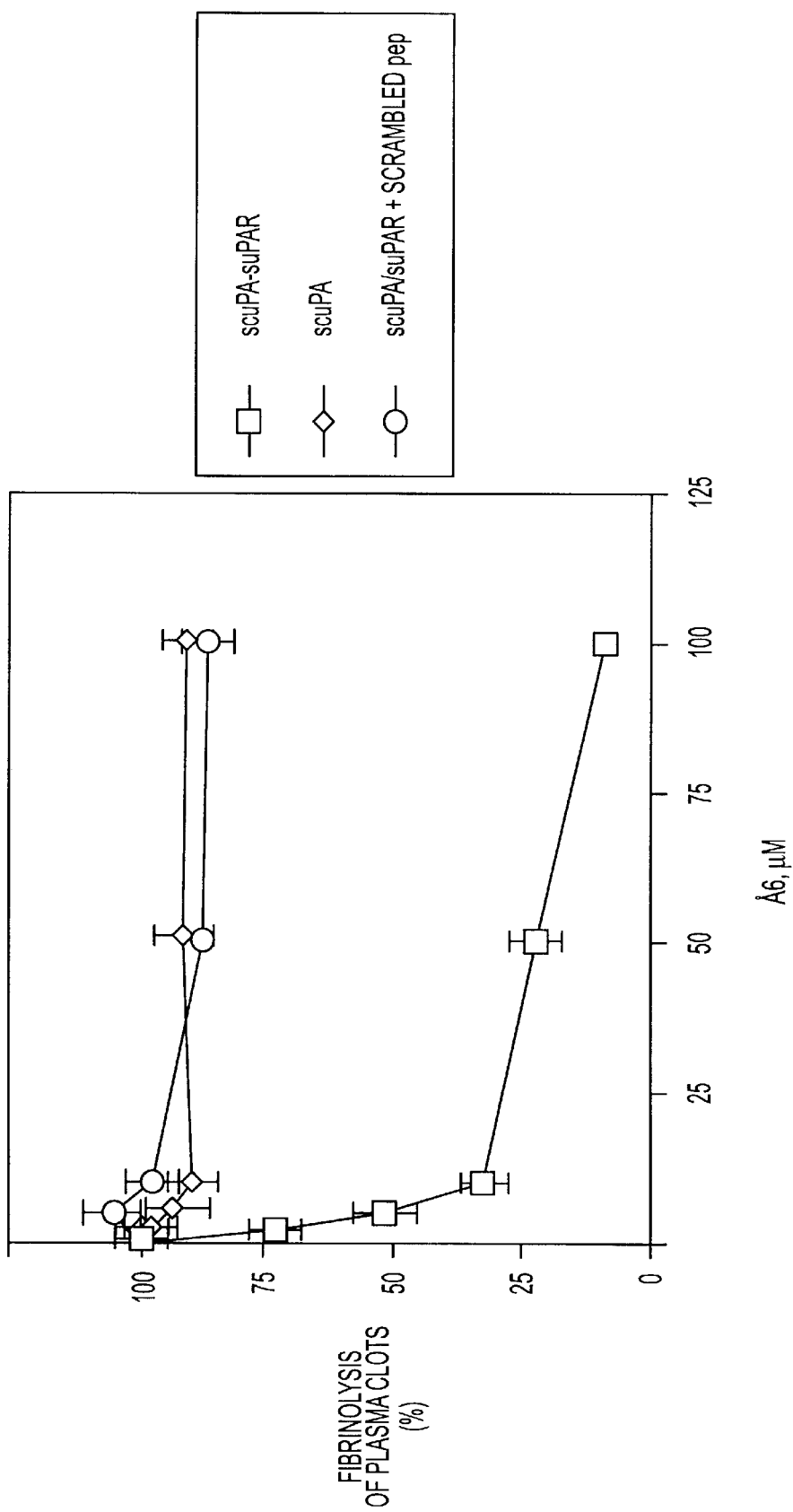
FIG. 3 shows that Å6 inhibits the activation of plasminogen in a clot lysis assay. Fibrin clots were formed by supplementing plasma with [$^{125}$I] fibrinogen. Clotting was initiated by adding thrombin and calcium to the plasma mixture. Clots were washed to remove any free radioactivity, plasminogen and the activator to be tested were added to the clot and the release of [$^{125}$I] fibrin degradation products was monitored. The data presented in this figure is at 30 minutes after initiation of clot lysis. scuPA-suPAR: dose response with Å6 on clot lysis by scuPA-suPAR complex; scuPA: dose response on clot lysis by scuPA alone; scuPA/suPAR+scrambled pep: dose response with a scrambled version of Å6 (Ac-PSESPEKP-Am).

Since Å6 was originally derived from uPA, its ability to inhibit various activities of uPA were tested, including binding to uPAR and the activation of plasminogen. Å6 had no effect in any of these assays except that it inhibited scuPA-suPAR mediated clot lysis (FIG. 3).

Å6 did not affect the activation of plasminogen by scuPA-suPAR when small, chromogenic substrates were used, and it did not affect the activity of either uPA or plasmin directly. The requirement of protein co-factors for the activation of plasminogen has been demonstrated by (Higazi et al., (1998) *Blood* 92, 2075–2083). Å6 may affect formation of a tertiary or ternary complex required for the activation of plasminogen in the clot lysis assay.

EXAMPLE IV

Actions of Å6 on Endothelial Cells

Figure 4:
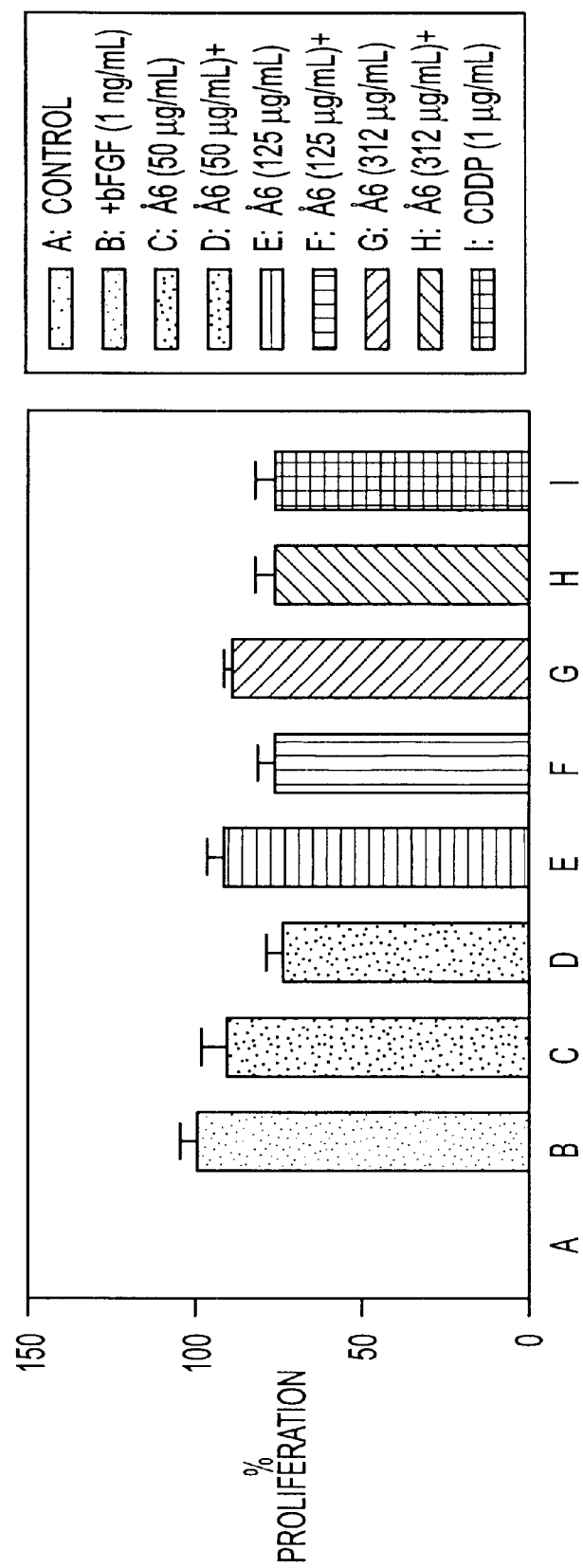
FIGS. 4 and 5 show the results of HUVEC proliferation assays. HUVEC were plated on gelatin and allowed to adhere for 4 hrs in the presence of 2% FBS. bFGF (1 ng/mL) and the test compounds were added after 4 hours and the % proliferation (where bFGF induced proliferation was 100% and proliferation in the absence of bFGF was 0) was determined using MTS.
Figure 5:
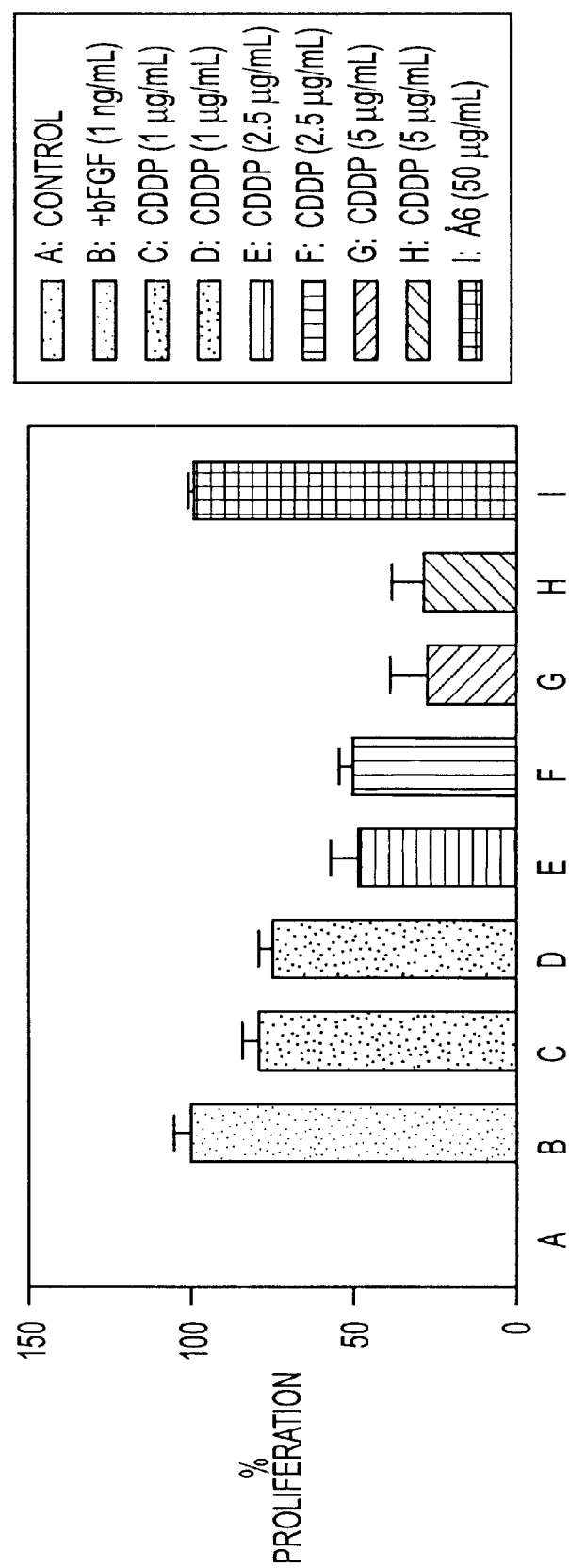

Å6 was tested for its ability to inhibit HUVEC proliferation. No inhibition was observed at concentrations as high as 312 μg/mL (340 μM) when HUVEC were grown on gelatin in 2% FBS (FIG. 4). Å6 did not potentiate the antiproliferative activity of cisplatin (CDDP) against endothelial cells (FIG. 5).

Figure 6:
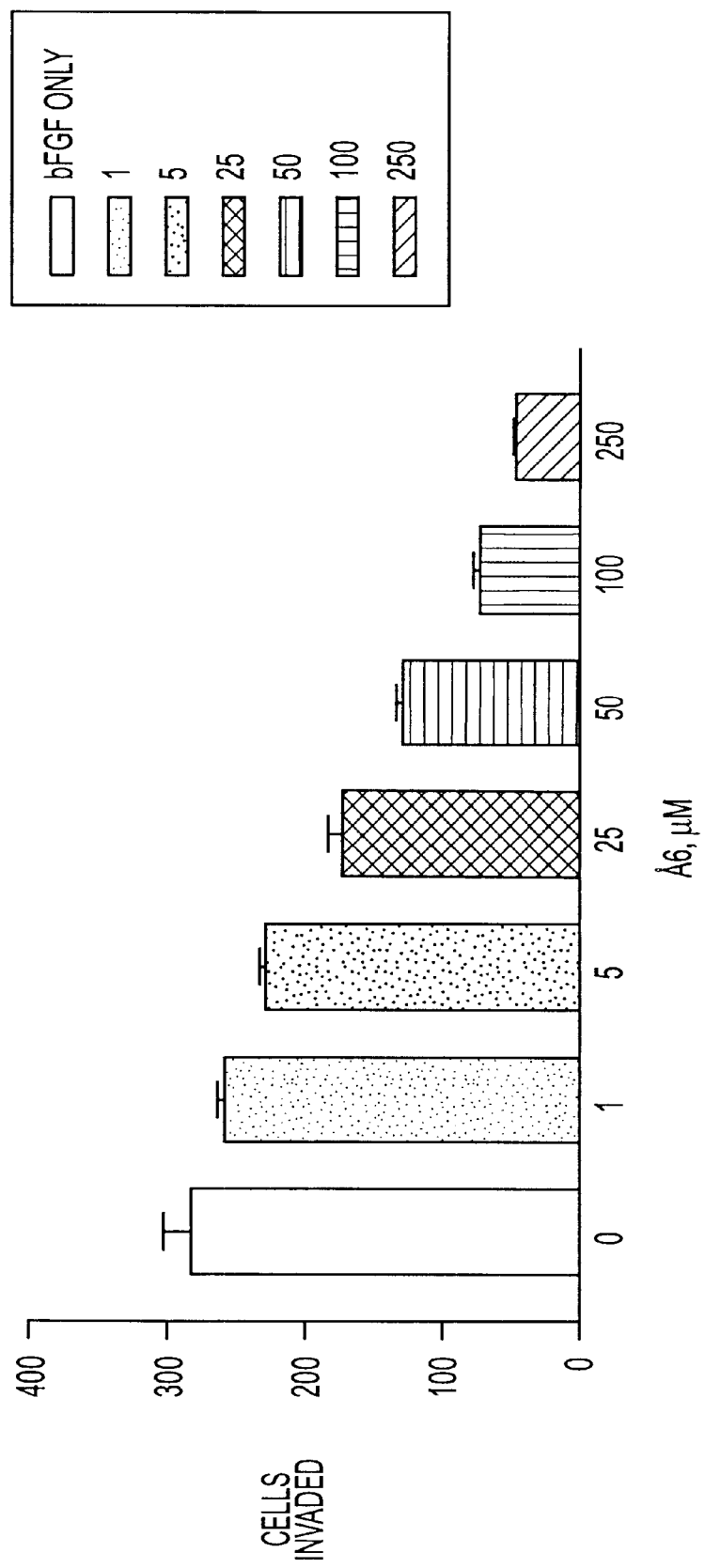
FIG. 6 shows the migration of HMVEC on Type I collagen. Membranes contained in transwell chambers (8.0 μm) were coated with Type I Collagen. Microvessel endothelial cells (HMVECs, 2×10$^5$/well) were added to the top chamber of each well and bFGF (10 ng/mL) was added to each bottom chamber as a chemoattractant. Inhibitor was added to both chambers and the migration allowed to proceed for 6 hrs at 37° C. The top of each filter was scraped to remove cells that had not migrated and the cells adhering to the bottom of the filter were fixed and stained using DiffQuick and the cells were quantitated by counting. The results are expressed as a percentage of the cells migrated in response to bFGF alone.

The ability of Å6 to inhibit endothelial cell migration was evaluated using HUVEC and lung and dermal microvessel endothelial cells (HMVEC) with essentially identical results. Typical results are presented in FIG. 6.

EXAMPLE V

Receptor Studies

Figure 9:
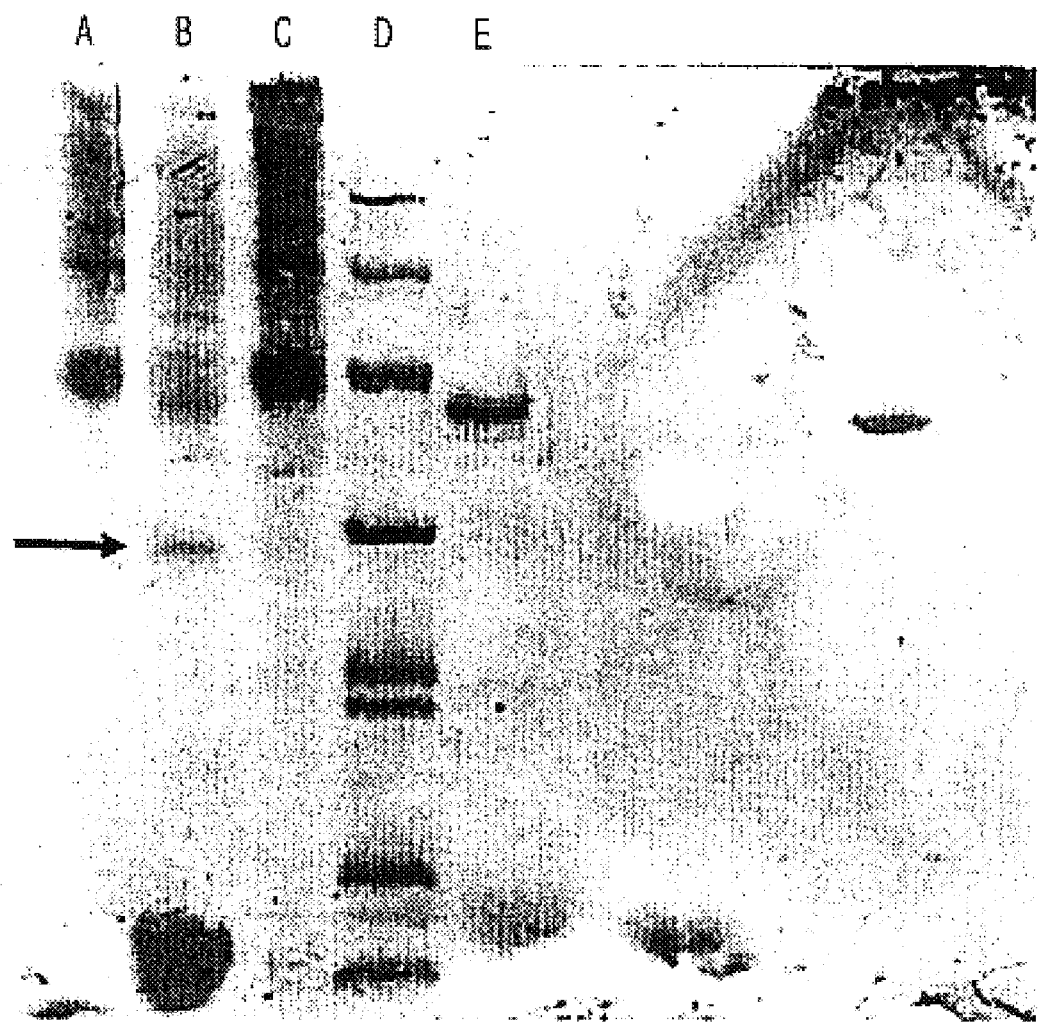
FIG. 9 is a PAGE gel pattern of biotin-Å6 crosslinked to MDA-MB-231 cells. Cells were incubated in the presence of biotin-Å6 (200 μM) for 2 hrs. DSS (1 mM) was added and cross-linking was allowed to proceed for 15 minutes. The cells were washed and extracted using PBS/1% Triton X-114. Cell particulate was removed by centrifugation and the supernatants were heated to 37° C. for 5 minutes to induce phase separation. Aqueous and detergent (membrane) phases were separated by centrifugation and each phase was resolved by SDS-PAGE and analyzed by western blot using strepatavidin-HRPO. A: Aqueous phase, 2$^{nd}$ wash; B: Detergent Phase; C: Aqueous phase, 1$^{st}$ wash; D: MW markers; E: Biotin-uPA.

The present inventors prepared Å6-biotin (conjugated to the N-terminus) and used this as a probe for receptor binding and identification. This conjugate was cross-linked to whole cells and cell extracts in an attempt to identify candidate receptors for Å6. After cross-linking, the extracts were resolved by SDS-PAGE and transferred to PVDF membranes. Cross-linked products were detected using streptavidin-HRPO. After analyzing the cross-linked products from several cell line extracts, the only candidate product thus far identified corresponds to a molecular weight of about 30 kDa (FIG. 9). Further, this product seems to be present only in the detergent phase of the extract, suggesting that it is membrane bound. The more intensely staining high-molecular weight products likely bind biotin directly, as they could not be competed with unbiotinylated Å6.

EXAMPLE VI

Additional In Vivo Actions of Å6 and Related Peptides

A. Angiogenesis in Chick Chorioallantoic Membrane (CAM)

Figure 10:
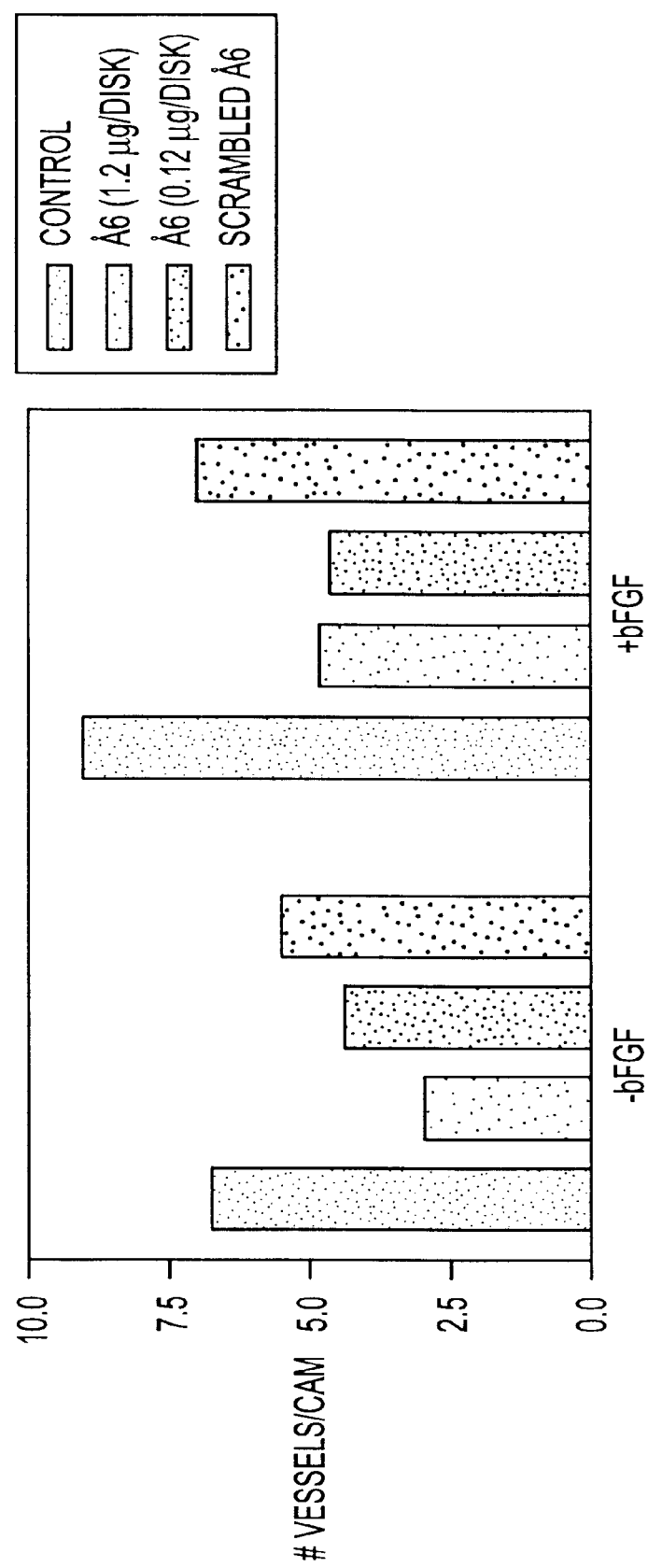
FIG. 10 shows that Å6 inhibits angiogenesis in a CAM assay. Filter disks saturated with either compound or compound+bFGF (0.3 ng) were placed on the CAM (7 day old) and vessel formation was observed for 4 days. Major vessels were quantitated at this time.
Figure 11A:
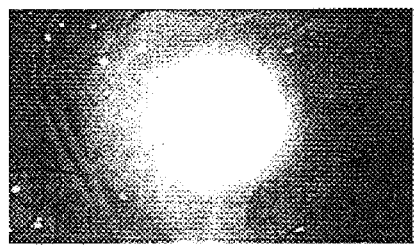
FIG. 11 shows the results of CAM assays. A: Control CAM; B: CAM treated with 1.2 μg/disk of Å6.
Figure 11B:
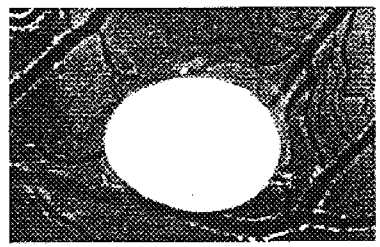
Figure 11C:
Figure 11D:
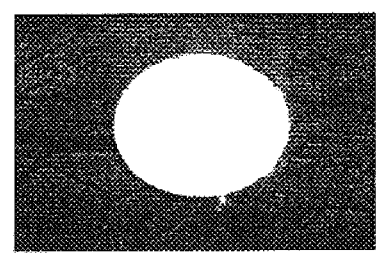

Å6 was tested for its effect on bFGF-induced angiogenesis in a 7 day old chick CAM assay. FIG. 10 shows results that are the average of 10 eggs for each condition tested. Å6 inhibited angiogenesis in this system. In addition to inhibiting major vessel formation, Å6 also inhibited branching morphogenesis; this effect is qualitatively evident in the stereomicroscopic images of the CAMs (FIG. 11).

The CAM assay serves as a useful system for measuring the effects of Å6 and related peptides or derivatives on events associated with the angiogenic "switch" as these events are observable in near-real time.

B. Tests for Inhibition of Tumor Angiogenesis

Angiogenesis induced by tumor growth and metastasis in vivo is examined in the models systems described above. Mice injected with 3LL cells are treated either with peptide or with vehicle and are sacrificed at various time points. Angiogenesis is assessed by determining microvessel density (MVD) using an antibody specific for microvascular endothelium or other markers of growing blood vessels, such as PECAM (CD31). Such an antibody is employed in conventional immunohistological methods to immunostain tissue sections as described by Penfold et al., supra. A large number of such antibodies is commercially available, for example the JC70 mAb. The MVD are correlated with other measures of tumor behavior including lymph node status and primary tumor size and rate of growth. In humans as reported by Penfold et al., supra, tumor MVD correlates with lymph node metastasis and is independent of tumor size, growth rate or type of histological differentiation. Only MVD showed a significant association with lymph node metastasis.

The compounds are given i.v., i.p., or by osmotic minipump. Typical dosages are 100–250 mg/kg/day. At various time points, two animals are sacrificed, and the tumor tissue and surrounding tissue is prepared for histological examination. Results are reported as the average microvessel density of 5 fields each from 5 different sections. The following seven compounds are tested: Ac-KPSSPPEE-Am (SEQ ID NO:2), Ac-KPTTPPEE-Am (disubstitution variant at positions 3 and 4), Ac-KPSSPPDD-Am (disubstitution variant at positions 7 and 8), Ac-RPSSPPEE-Am (substitution variant at position 1), Ac-PSSPPEE-Am (deletion variant, position 1 of SEQ ID NO:2 deleted), Ac-KPSSPPE-Am (deletion variant, position 8 of SEQ ID NO:2 deleted), and Ac-KPPSSPPEELK-Am (SEQ ID NO:1).

The following results are obtained. In the rats treated with Ac-KPSSPPEE-Am, Ac-KPTTPPEE-Am, Ac-KPSSPPDD-Am and Ac-RPSSPPEE-Am, there is a significant reduction in the number of microvessels in the region of the primary tumor at the subcutaneous inoculation site as compared to controls. Peptides Ac-PSSPPEE-Am, Ac-KPSSPPE-Am and Ac-KPPSSPPEELK-Am had no significant effect on angiogenesis. Therefore, the four indicated compounds have anti-angiogenic activity which is responsible at least in part for their effectiveness as antitumor agents.

C. Growth and Metastasis of Rat Mat B-III Breast Cancer

The rat syngeneic breast cancer system (Xing and Rabbani, 1996) employs Mat BIII rat breast cancer cells. When Mat B-III cells (1×10$^6$ cells) are inoculated into the mammary fat pad of female Fisher rats, they form large tumors which metastasize to regional lymph nodes (LNs) and other distal sites within 14–20 days.

Figure 12:
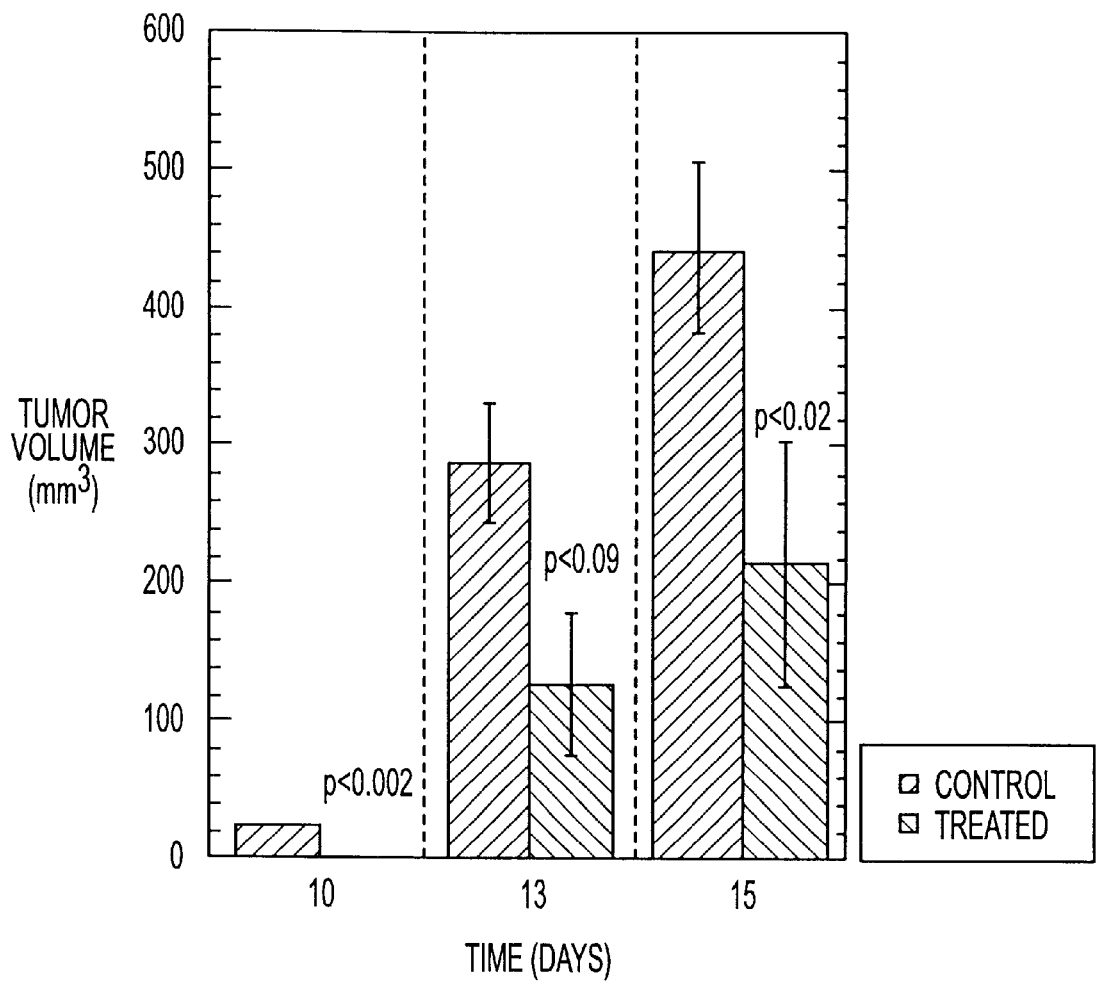
FIGS. 12 and 13 show that Å6 inhibits Mat B-III tumor growth and metastasis.
Figure 13:
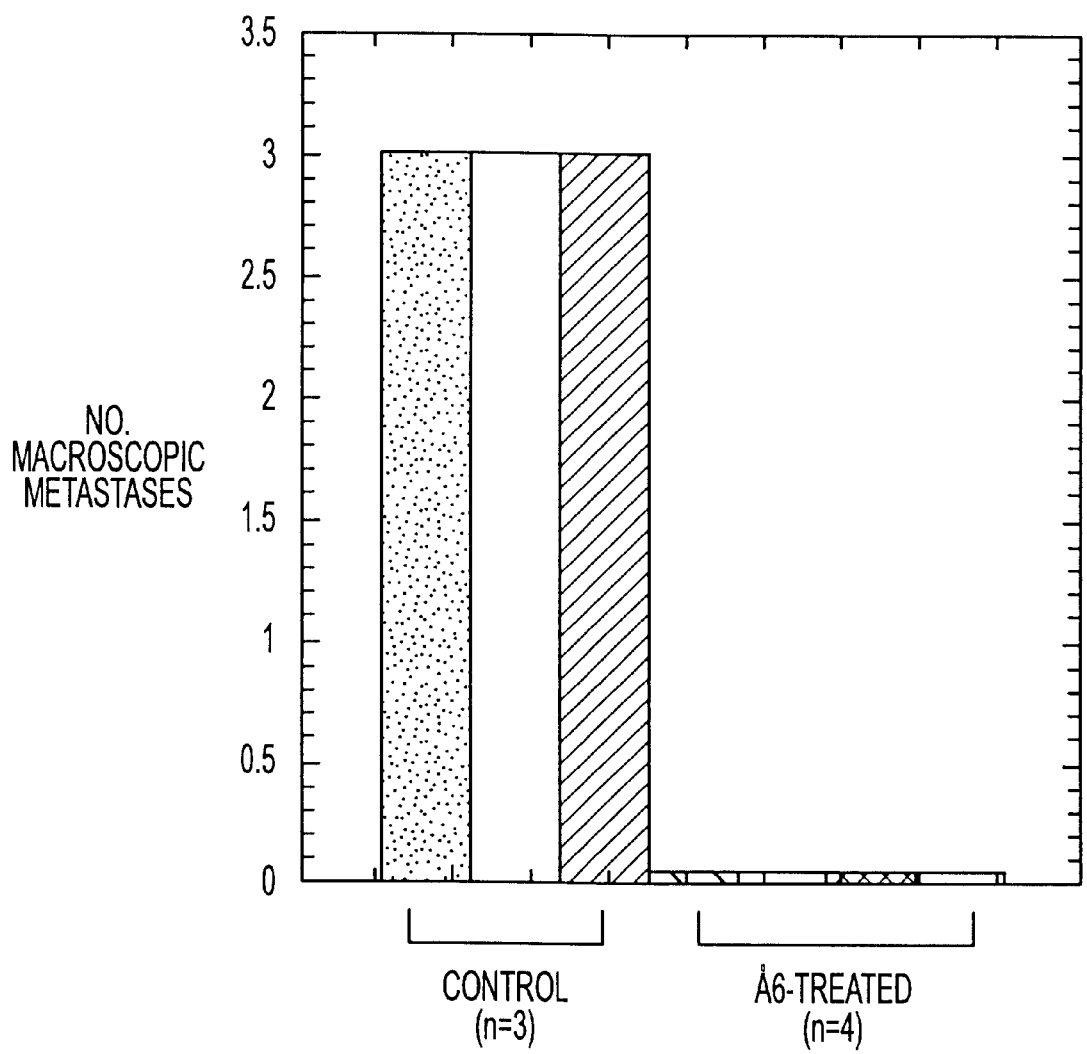

Å6 was initially delivered prophylactically (infusion starting on the day of tumor inoculation) using an Alzet minipump that delivered 75 mg/kg/day. This treatment had substantial anti-tumor activity including inhibition of tumor growth and LN metastasis. Intraperitoneal delivery of Å6 (75 mg/kg/day given IP b.i.d.) produced similar results on tumor growth (FIG. 12) and metastasis (FIG. 13). Metastasis was quantitated by counting the number of macroscopic foci without regard for their size.

Å6 was clearly more effective when the tumors were smaller. However, despite the increase in growth rate of the primary challenge tumors, the formation of macroscopic metastatic foci continued to be suppressed during the course of this treatment schedule. Representative LNs were excised from both control and Å6-treated animals, fixed in formalin and embedded in paraffin for histological examination. Tumor cells were found in LNs from Å6-treated rats, despite the lack of macroscopic metastases.

Histological analysis of the primary tumor also revealed extensive necrosis at the tumor periphery. Typically, in the primary tumors, the central core is spontaneously necrotic. However, in Å6-treated rats, the periphery was 50–75% necrosed in all tumors evaluated. The only remaining viable tumor cells formed perivascular cuffs around what appeared to be pre-existing blood vessels. Each of these cuffs was approximately 5 cells in width, consistent with Folkinan's observations that a tumor could expand no farther than 5 cells away from its blood supply without initiating the formation of neovessels (Folkman J (1992) *Semin Cancer Biol* 3:65–7112).

Many of the cells in the Å6-treated groups stained positive in the TUNEL assay for apoptosis, indicating that apoptosis of tumor cells was occurring. Because TUNEL detects fragmented DNA, other mechanisms of cell death (including necrosis) might also have contributed.

Factor VIII staining of tumor sections in Å6-treated animals also revealed a 40–60% decrease in Factor VIII-positive foci (data not shown).

In a comparative analysis of related peptides, the following results will be obtained. In the rats treated with Ac-KPSSPPEE-Am (Å6), Ac-KPTTPPEE-Am, Ac-KPSSPPDD-Am and Ac-RPSSPPEE-Am, there is a significant reduction in the size of the primary tumor and in the number of metastases in the spleen, lungs, liver, kidney and lymph nodes (enumerated as discrete foci). Upon histological and immunohistochemical analysis, it is seen that in treated animals, there is increased necrosis and signs of apoptosis. Large necrotic areas are seen in tumor regions lacking in neovascularization. In contrast, treatment with peptides Ac-PSSPPEE-Am, Ac-KPSSPPE-Am and Ac-KPPSSPPEELK-Am will fail to cause a significant change in tumor size or metastasis.

D. Treatment of Mat B-III Tumors with Å6 +Tamoxifen ("TAM")

The present inventors evaluated the ability of Å6 to potentiate the activity of TAM, an anti-estrogen used in the treatment of human estrogen receptor-positive breast cancer. One promise of anti-angiogenic therapy is the potential for preventing or inhibiting tumorigenesis, a prophylactic outcome, in patient populations at risk for a particular type of cancer. TAM may be beneficial as a prophylactic treatment for some patients at risk of developing breast cancer (although this is controversial because it TAM could accelerate the formation of certain subtypes of breast cancer. TAM is part of the accepted treatment regimen in early stage breast cancer. Thus, the combination of an anti-angiogenic agent such as the compounds of this invention, will have prophylactic and therapeutic effects in on early stage breast cancer.

Figure 14A:
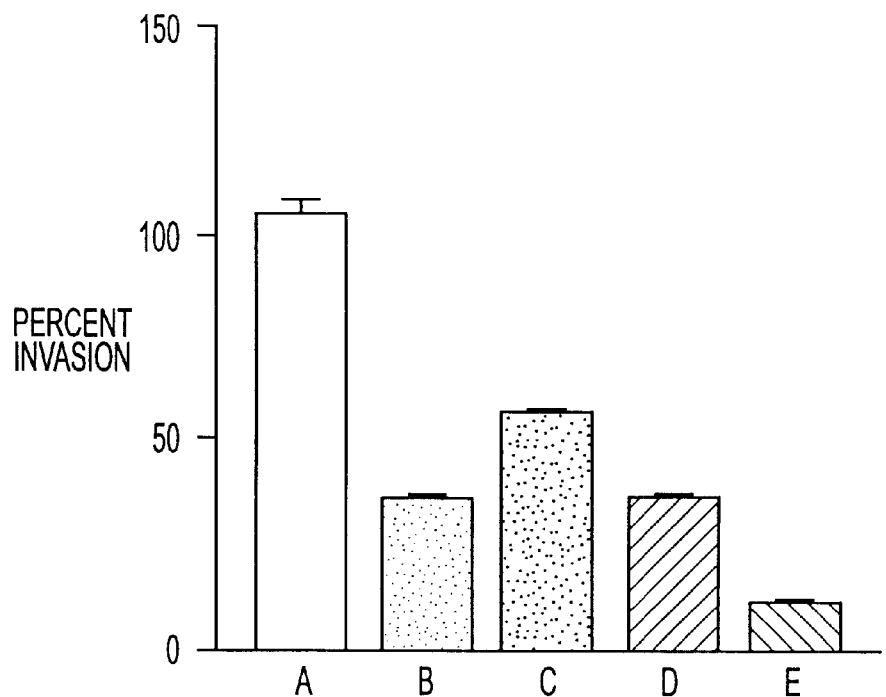
FIG. 14 shows results of in vitro and in vivo studies using Å6 and TAM. Top Panel: Invasion of Mat B-III cells through Matrigel®. A: Control; B: TAM (1 μM) C: Å6 (5 μM); D: Å6 (50 μM); E: Å6 (50 μM)+TAM (1 μM). Bottom Panel: Mat B-III tumor bearing animals were treated with TAM (3 mg/Kg/day), Å6 (75 mg/kg/day) or a combination of TAM+Å6. Tumor volumes were determined using caliper measurements. Control received vehicle (PBS) only.
Figure 14B:
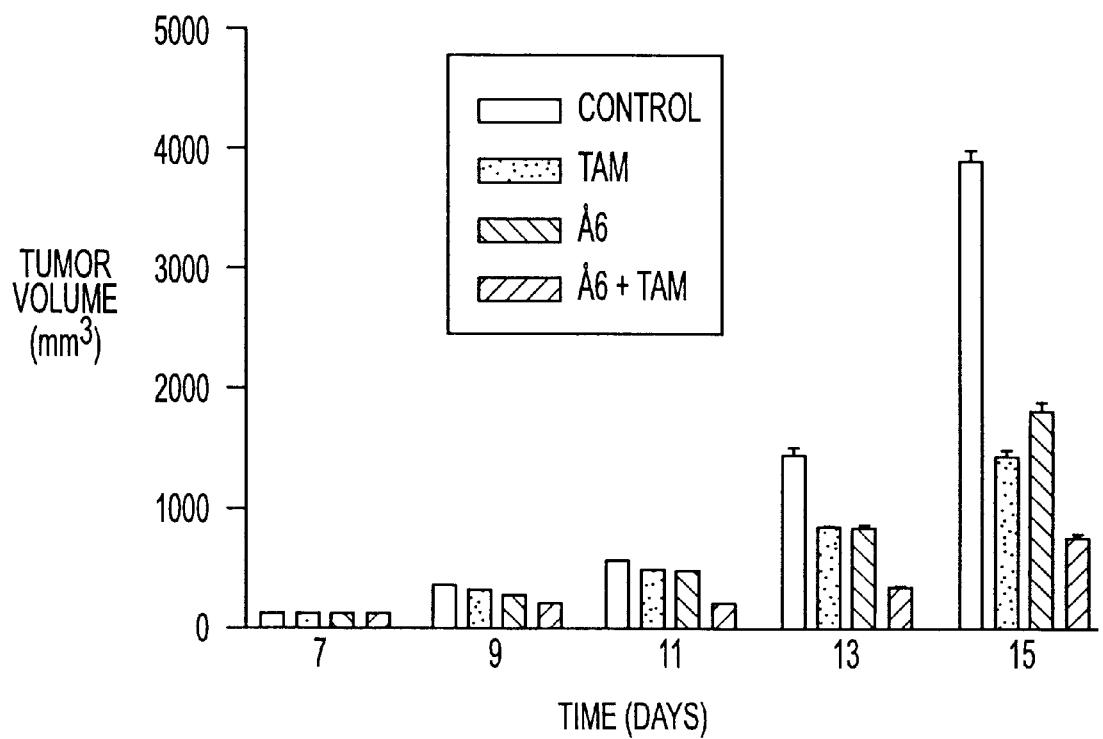

Estrogen receptor-positive Mat B-III tumors were used to test combination treatment with Å6 (75 mg/kg/day) and TAM (3 mg/kg/day). In contrast to previous studies, the Mat B-Ill tumors (inoculated in the mammary fat pad) were staged to 40–50 mm$^3$ prior to the initiation of treatment. Treatment was continued for 8 days during which time primary tumor growth was measured using calipers (FIG. 14). The combination was a more potent antitumor therapeutic than TAM or Å6 alone.

E. Treatment of Xenografted Human MDA-MB-231 Tumors with Å6

The results obtained with the Mat B-III model were extended to a human tumor xenograft model of MDA-MB-231 human breast cancer cells. These cells were first transfected with green fluorescent protein (GFP) to simplify the detection and visualization of metastases. The growth curves of the GFP-transfected MDA-MB-231 cells (MDA-MB-231 GFP) were indistinguishable from the parental cells. The in vitro invasive activity of both cell lines was also identical indicating that GFP transfection did not alter cellular behavior.

Figure 15:
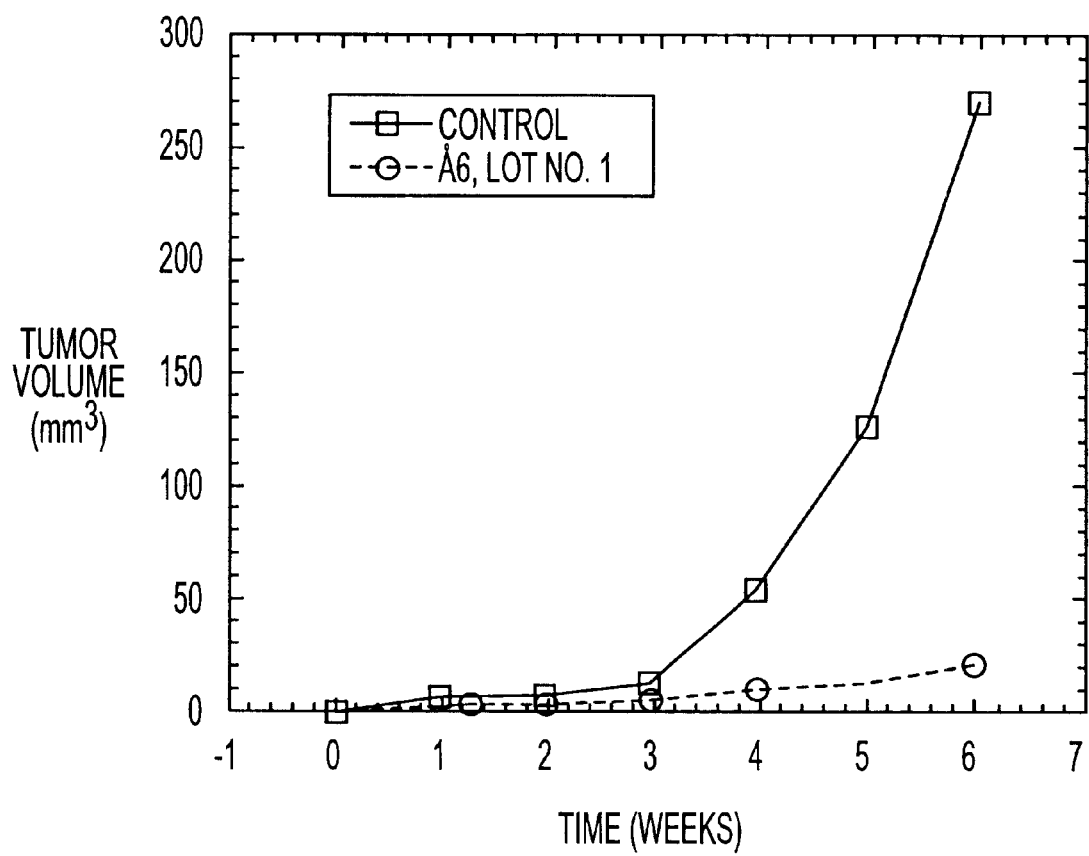
FIG. 15 shows that Å6 inhibits the growth of primary challenge tumors in an MDA-MB-231 xenograft model. Nude mice (n=5 per group) were challenged with 2×10$^5$ tumor cells co-injected into the mammary fat pad of the mice with Matrigel®. Treatment of the mice with Å6 (IP, 1 mg bid) was initiated when tile tumor nodules had become palpable (beginning of week 1 on graph). Control animals received vehicle (PBS) only.

The tumor cells ($5 \times 10^5$) were suspended in 0.1 mL of Matrigel and injected into the mammary fat pad of female BALB/c nu/nu mice. Treatment (75 mg/kg/day) was initiated when the tumors were palpable (10 mm$^3$, approximately 4 weeks after inoculation of tumor cells) and continued for 5 weeks. Tumor volumes were determined twice per week using caliper measurements. The animals were euthanized at the end of the 5$^{th}$ week of treatment, necropsied and examined for macroscopic metastases. Sections prepared from LNs, lung, liver, spleen and kidney were analyzed for microscopic dissemination of tumor cells using fluorescence microscopy to detect GFP-positive foci. As shown in FIG. 15, Å6 treatment inhibited tumor growth by >80%.

Å6 was ineffective in this model if the tumors were staged to 50–100 mm$^3$ prior to initiating treatment. The bi-phasic nature of the growth curve appears to represent the growth rate of the tumor before (slow growth or dormancy) and after (fast growth) the angiogenic switch (which occurs at the inflection point of the curve). Thus, if Å6 is found to inhibit events associated with the angiogenic switch, to be effective it should be administered before the switch. Folkman's group (Bergers et al., Science 284: 808–812) recently demonstrated the stage-specific nature of angiogenesis inhibitors. Most angiogenesis inhibitors do not cause regression of established tumors when used alone—anti-angiogenic therapy appears to be most efficacious in animal models when it is targeted to a specific stage of tumor progression. The activity of Å6 is consistent with this notion.

TUNEL and Factor VIII staining of tumor sections revealed results similar to those observed in the rat studies reported above. Tumors from Å6-treated animals demonstrated a significant increase in TUNEL-positive foci as well as a decrease in Factor VIII-positive hot spots.

Macroscopic metastases were enumerated and their size measured with calipers (Table I, below). Microscopic dissemination of tumor cells was quantitated by counting GFP-positive foci in representative sections from lung, liver, kidney and spleen. Disseminated tumor cells were not evident in kidney sections. Because disseminated cells may exist in a dormant state for many years or, in some cases, never progress, one cannot posit an absolute correlation between the presence of disseminated cells and metastasis. Nevertheless, the foci in liver and lungs did appear to be true metastases as the cells were not single foci but seem to have formed larger colonies in the control animals. Sections from Å6-treated animals appeared to have a greater number of single foci (vs. larger colonies), indicating lack of metastatic progression.

Macrometastases were determined by excising involved LNs and determining the tumor volume by caliper measurement. Microscopic tumor foci were quantitated by sectioning and fixing target organs, then visualizing GFP-labeled cells using fluorescence microscopy (at 200× enlargement). The number of disseminated tumor foci represents the average of 5 fields per section from 3 different sections per organ.

TABLE I

| (a) Macroscopic Metastases | | | | |
|---|---|---|---|---|
| | Lymph Nodes | | Lungs | |
| Group | Number | Size (mm$^3$) | Number | Size |
| Control | 4.5 ± 1.2 | 27 ± 3 | 4.2 ± 1.8 | N.D. |
| A6-treated | 1.2 ± 0.2 | 7 ± 3 | 1 ± 0 | N.D. |

| (b) Disseminated GFP-positive Tumor Foci | | | |
|---|---|---|---|
| | Lung | Liver | Spleen |
| Control | 4.23 ± 0.18 | 18.83 ± 0.36 | 35.67 ± .82 |
| A6-treated | 2.09 ± 0.30 | 3.11 ± 0.14 | 28.30 ± 2.80 |

Figure 16:
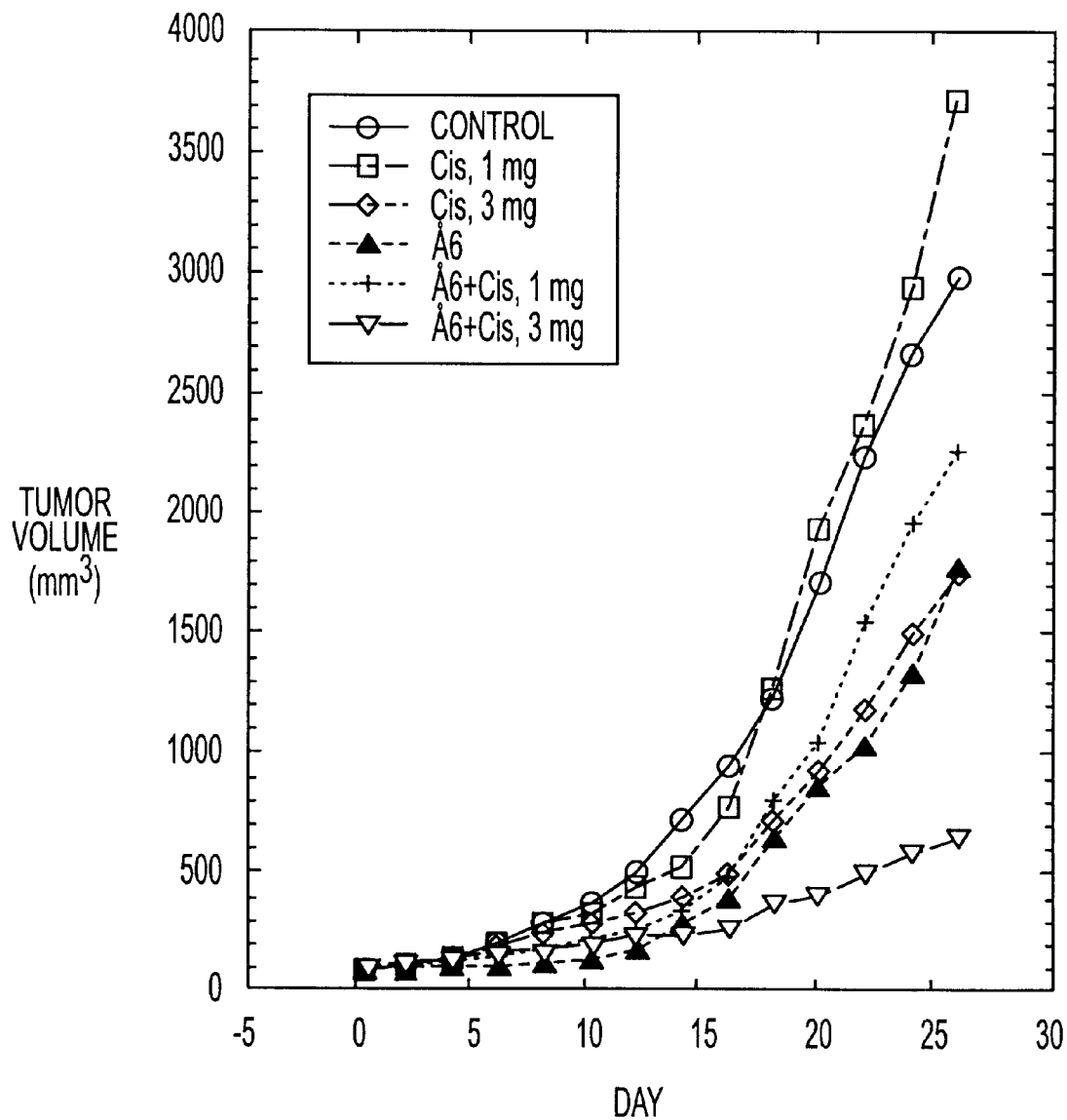
FIG. 16 shows results of combination therapy of U87 tumors inoculated s.c. in nude mice. U87 cells (1×10$^5$) were inoculated Sc on the back of a nude mouse (n=5). Tumors were staged to 50–100 mm$^3$ (day 0) at which time treatment was started with either Å6 alone (75 mg/kg/day given IP bid), cisplatin (CDDP) alone (3 mg/kg/day given every other day from day 4×6 administrations), or a combination of Å6+CDDP. Tumor volumes were determined using caliper measurements. Treatment was discontinued at day 20 and the mice were euthanized one week later.
Figure 17:
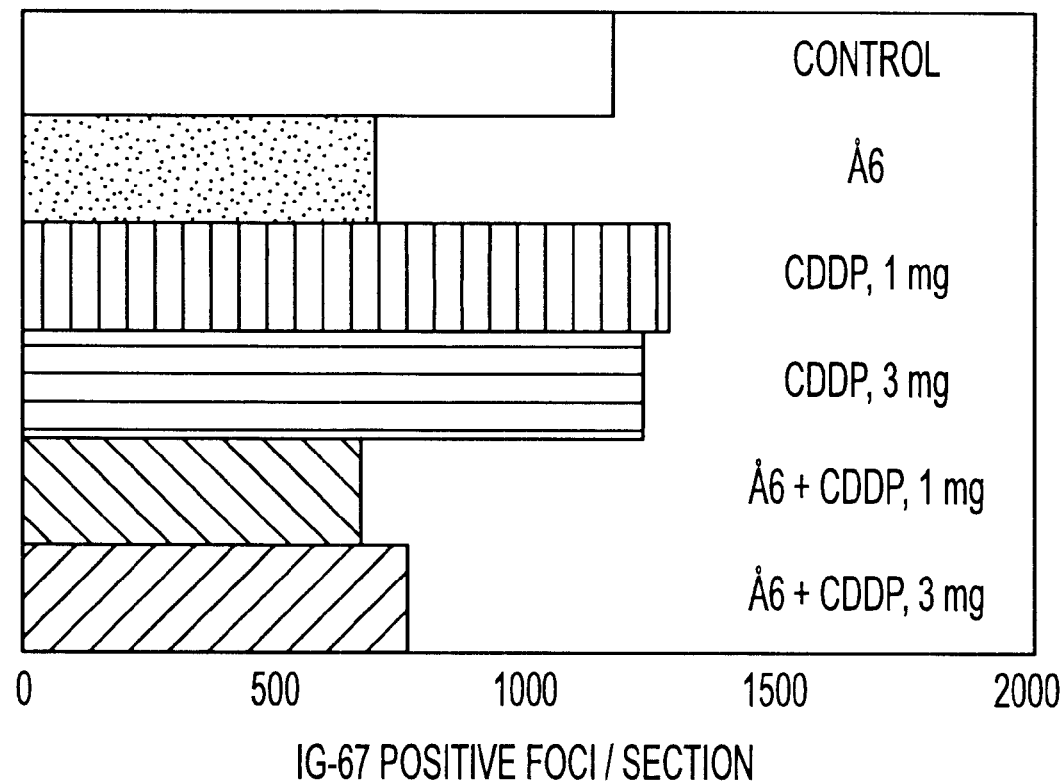
FIG. 17 shows the number of tumor foci using Ki-67 staining of U87 tumors. Formalin-fixed sections were stained with mouse anti-Ki-67 followed by peroxidase detection. Positive foci were quantitated by capturing digital images of the slides and determining the number of pixels associated with the staining on each slide.

F. Treatment of U87 Human Glioblastoma U87 Xenografts
  1. Growth of Primary Tumors after Subcutaneous Implantation Tumors were established by subcutaneous injection of human U87 glioblastoma ("GBM") cells sc into nude mice. U87 tumors were staged to 50–100 mm$^3$ prior to initiating treatment. Å6, cisplatin (CDDP) and the combination of Å6+CDDP were tested (FIG. 16). CDDP was tested at a dose of 3 mg/kg/day given every other day from day 4×6 administrations, which converts to approximately 6 mg/m$^2$ per administration. This is a substantially lower dose than that typically given to human patients (20–40 mg/m$^2$ for most tumors although doses as high as 200 mg/M$^2$ have been reported in neuroblastomas; the dose depends on the regimen used) since dose limiting toxicity (as exemplified by weight loss) occurs in mice at doses greater than 6 mg/m$^2$. Thus, the full benefit of CDDP+Å6 as a combination therapy may exceed that which was observed here.

As the combination treatment of Å6 +CDDP was highly effective in inhibiting tumor growth in this model, the present inventors assessed the proliferative (mitotic) index in these tumors. Typically, human GBM is not characterized by rapid proliferation and only 15% of the tumor cells are typically proliferating (CLINICAL ONCOLOGY (1995) Abeloff, M. D. et al., eds. Churchill-Livingstone, N.Y.). For this reason, anti-metabolites are not efficacious in treating this type of tumor. Though alkylating agents (such as CDDP and BCNU) have been the most successful in treating GBM in the clinic (as they induce apoptosis by damaging tumor cell DNA), they are not selective for rapidly dividing cell populations and are quite toxic.

Figure 18:
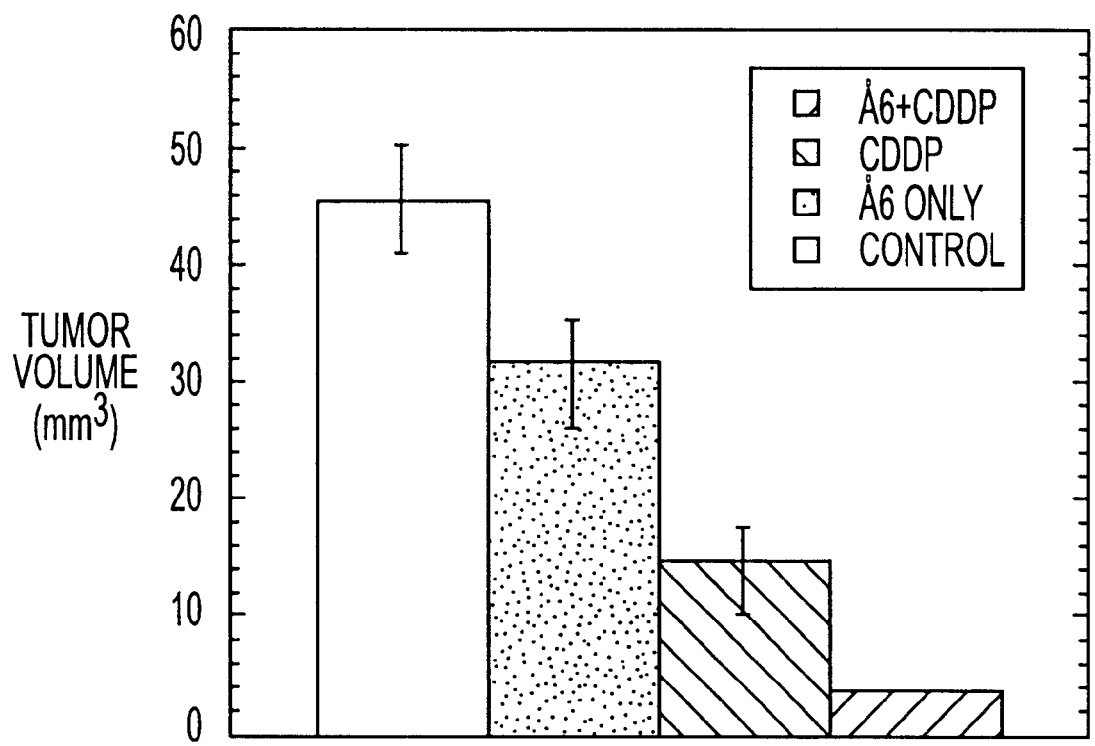
FIG. 18 shows the effects of Å6 on orthotopically inoculated human U87 GBM cells. U87 cells were inoculated into the ventricles of nude mice and treatment was initiated 72 hrs after inoculation. Tumor volume was determined using caliper measurements after euthanasia and necropsy.

Anti-angiogenic therapy is expected to produce both anti-proliferative and pro-apoptotic effects that would "prime" the tumor chemotherapy with these alkylating agents. The proliferative index in the U87 tumors was evaluated using Ki-67 staining followed by digitization of the staining intensity and quantitation. Three sections from each animal were evaluated for Ki-67 positive staining (FIG. 18). Å6 treatment inhibited proliferation by 50%, which was not enhanced by combination treatment with CDDP, as predicted by the inventors. Å6 did not inhibit U87 cell proliferation directly nor did it potentiate the pro-apoptotic activity of CDDP in vitro. Similar results were obtained against other human GBM cell lines, including those designated 308 and U251.

Dose Response Studies

Figure 19:
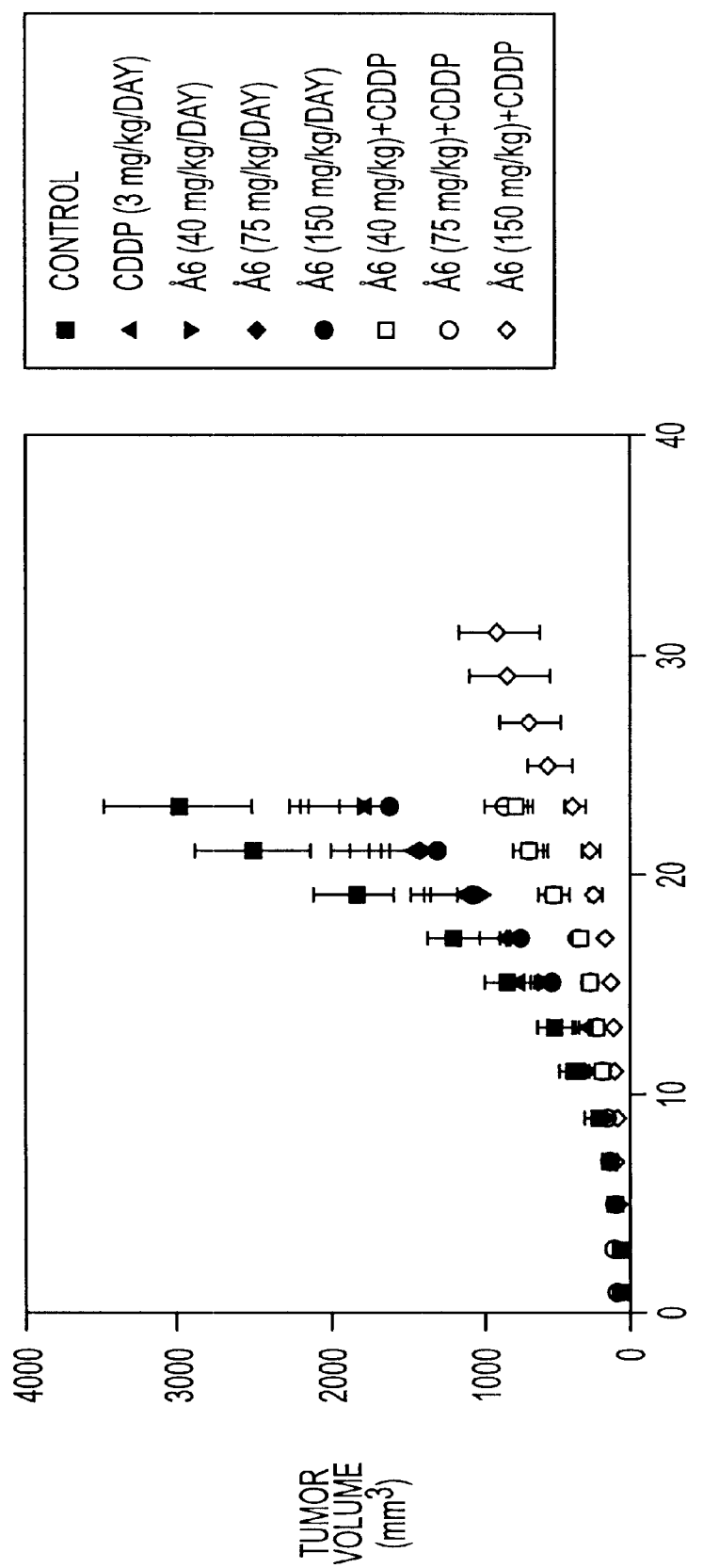
FIG. 19 shows the dose dependent response of U87 tumor growth to Å6. Mice (n=4 per group) were treated as previously described and treatment was discontinued after 21 days.

The effect of different doses of Å6 on U87 tumor growth sc was evaluated (FIG. 19). Tumor growth was almost completely suppressed in animals treated with the combination of the Å6 (150 mg/kg/day) and CDDP as long as treatment was continued. Tumors grew when treatment was discontinued. Tumor regression (defined as a tumor that was no longer palpable) was observed in 1 or 4 mice in this group, a response that was durable throughout the course of the experiment. This individual mouse is being analyzed for the presence of microscopic tumor. Once information with an even higher dose of Å6 (300 mg/kg/day) been obtained, the results will be extrapolated to the orthotopic model where the effects of higher doses of Å6 on angiogenesis and survival will be evaluated.

2. U87 Implanted Orthotopically

U87 tumors were surgically inoculated into the cerebral ventricles of mice. The animals were allowed to recover for 72 hours at which time treatment with Å6 (75 mg/kg/day IP bid), CDDP (3 mg/kg/day given every other day from day 4×6 administrations), or a combination of Å6 +CDDP was initiated.

Animals were treated for 21 days at which time they were euthanized and their brains evaluated for the presence of tumor. Transverse sections were stained with hematoxylin and eosin (H&E). The combination of Å6 and CDDP was significantly more effective in inhibiting U87 tumor growth than either agent alone.

Tumor sections were also evaluated for microvessel density using antibodies specific for mouse-CD31 in immmunostaining. Very few CD31$^+$ foci were evident in animals treated with the combination of Å6+CDDP. In fact, CDDP and Å6 alone both inhibited angiogenesis to some extent. Qualitatively, Å6 appeared not only to inhibit the number of vessels but also the differentiation of the vessels as fewer branching vessels were observed in the Å6-treated tumors.

3. Survival of Mice Implanted Orthotopically with U87

Figure 20:
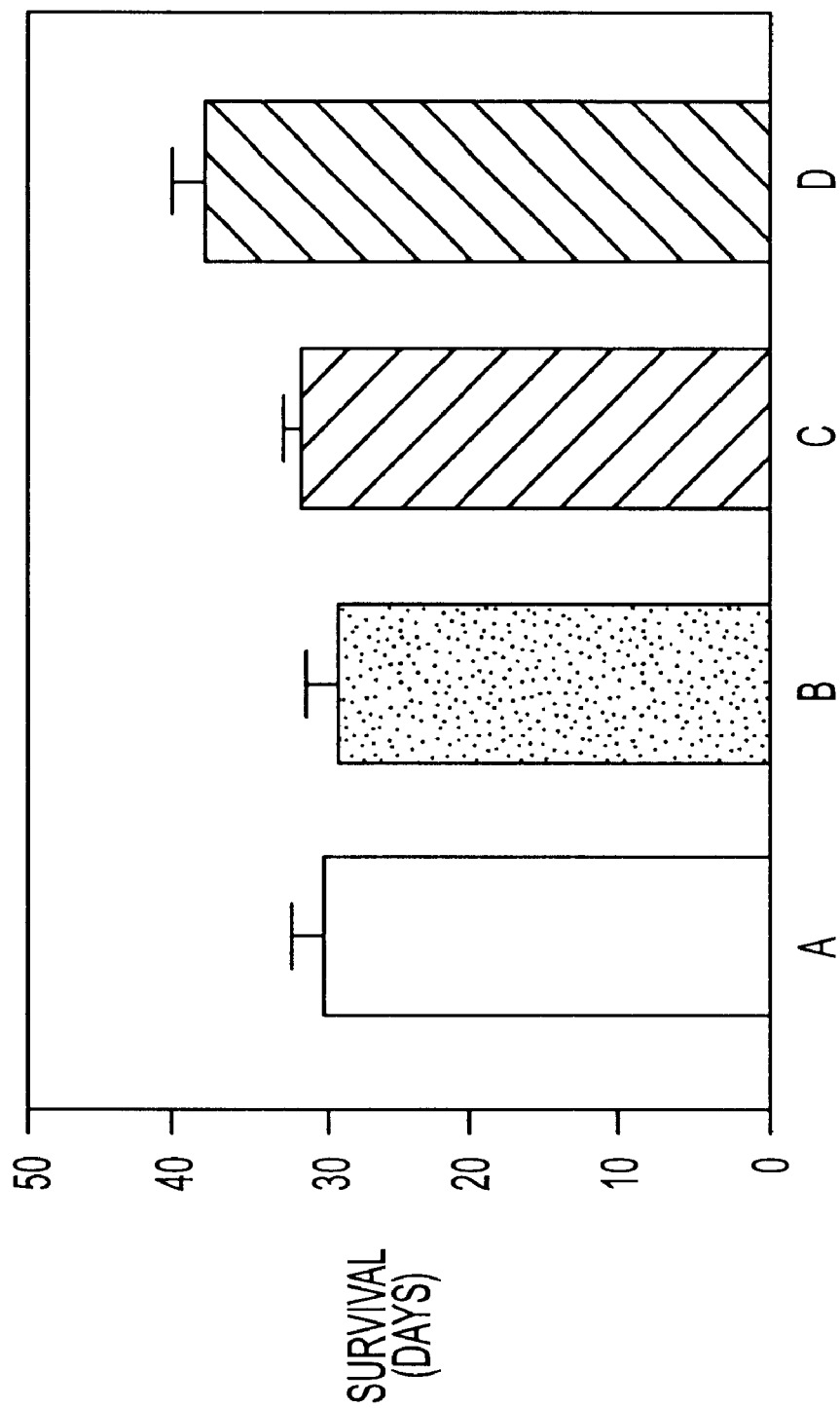
FIG. 20 shows the effect of Å6 and CDDP on survival of mice with orthotopically inoculated U87 GBM tumors. A: Control; B: Å6 only; C: CDDP only; D: Å6+CDDP.

Tumors were established as in the previous section, and the same therapeutic regimens were employed. Treatment was discontinued at day 21, and survival was measured. Control animals appeared moribund around day 25 and all of the animals in this group were dead by day 30. In contrast, the combination treatment group showed a significant increase in survival when compared to the control group or to the groups receiving either Å6 or CDDP alone (FIG. 20).

Figure 21:
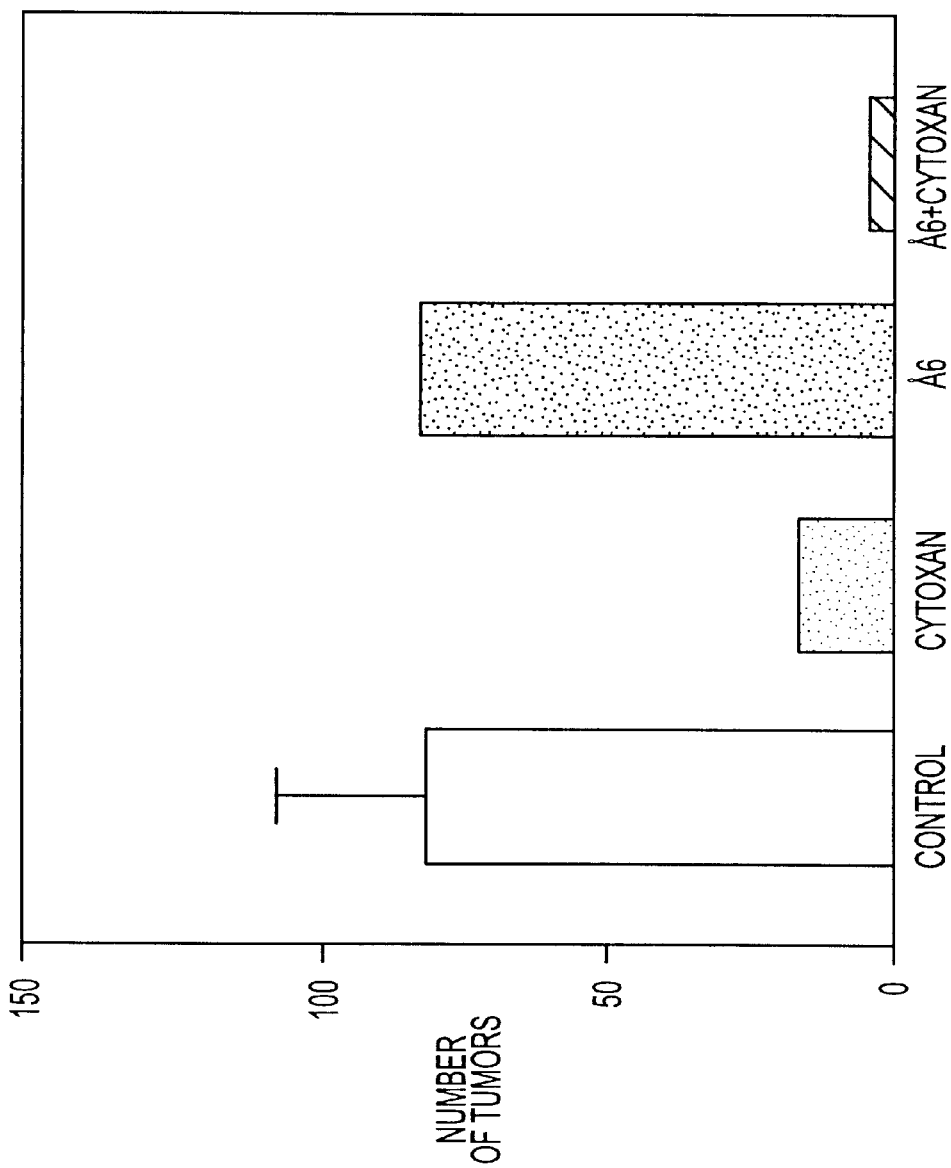
FIG. 21 shows the results of combination treatment of 3LL tumors with Å6+cyclophosphamide. 3LL cells (1.5×10$^5$ cells) were injected into the tail vein of C57/Bl mice. Treatment with Å6 (75 mg/kg/day IP b.i.d) and cyclophosphamide (4 mg/kg IP on day 4) was continued for 19 days. Animals were euthanized on day 20 and the lungs removed and analyzed macroscopically and histologically for the presence of tumor. The average number of tumors in each group (n=7) is shown.

G. Treatment of Murine Lewis Lung Carcinoma (3LL) Experimental Metastasis/Lung Colonization Lewis Lung Carcinoma cells (3LL, 1.5×10$^5$ cells per mouse) were injected i.v. into C57BL/6 mice. Mice were treated with cyclophosphamide (CY: 300 mg/kg once on day 4) alone, Å6 alone (treated from day 0-day 19 at 75 mg/kg/day) or a combination of CY+Å6. The animals were euthanized on day 19 and the lungs harvested for analysis. Macroscopic metastases were counted and the lungs analyzed histologically. Combination treatment reduced the total number of lung colonies when compared to control or CY only groups (FIG. 21).

Histological evaluation of tumors from the combination treatment group revealed that the lungs were mostly free of tumor. In lungs having small amounts of residual tumor, hemorrhagic necrosis was observed in some of the foci.

Additional Studies of Metastasis

In addition to Å6, other related peptide compounds described above are tested for efficacy in vivo in the 3LL model (as provided above) as well as the PC-3 model. PC-3 cells transfected with the gene encoding the enzyme chloramphenicol acetyl-transferase (CAT) are inoculated into mice i.v. at doses of 1×10$^6$ cells per mouse. These mice are implanted with a minipump, as above, which dispenses 100 mg/kg/day of the peptide or vehicle over a period of 14 or 21 days. At termination of treatment, the animals are euthanized and the tumor marker probe is assayed in regional lymph nodes, femurs, lungs, and brain.

The following results are obtained in both systems. In mice treated with Ac-KPSSPPEE-Am (Å6), Ac-KPTTPPEE-Am, Ac-KPSSPPDD-Am and Ac-RPSSPPEE-Am, metastasis is markedly inhibited. These results indicate that these compounds interfere with the metastatic process. In contrast, mice treated with peptides Ac-PSSPPEE-Am, Ac-KPSSPPE-Am and Ac-KPPSSPPEELK-Am have no reduction in metastases.

Other uPAR-binding peptides with utility as tumor-targeted imaging agents that have been discovered by the present inventors are the subject of an issued patent (U.S. Pat. No. 5,942,492) and co-pending, commonly assigned patent applications U.S. Ser. No. 09/285,783 filed Apr. 5, 1999; U.S. Ser. No. 09/1891,816 filed Oct. 29, 1999; and provisional application No. 60/157,012, filed Oct. 1, 1999 (all of which documents are incorporated by reference in their entirety). Some of these agents are useful as radiodiagnostics for evaluating tumor size and dissemination. These can be used in monitoring patients during therapy. Some of these reagents have been designed to carry a Tc$^{99m}$ γ-emitting nuclide to the surface of solid tumors and tumor vessels. These same constructs are also useful in localizing a Tc$^{94}$ isotope for PET imaging.

EXAMPLE VII

Pharmacological and Pharmacodynamic Evaluation of Å6

1. Pharmacodynamic Markers

Evaluation has begun of several markers that are expected to be associated with a therapeutic response of tumors to Å6. Molecules associated with angiogenesis will be evaluated for their utility as pharmacodynamic markers of Å6 activity. Certain markers (bFGF, MMPs) will be detected in urine 2. Pharmacology Liquid Chromatography/Mass Spectroscopy (LC/MS) Assay Development An LC/MS assay developed for the detection of Å6 in plasma has been validated for mouse and monkey plasma. The sensitivity is 10 ng in 0.1 mL of plasma. This test can be similarly validated for human plasma under GLP conditions to be used for human pharmacology. Protein binding studies are presently underway. Because the peptide can be recovered from plasma after simple precipitation of total protein (Å6 is in the supernatant), the undesired effect caused by extensive binding of the peptide to other proteins is not expected. Å6 is extremely soluble and can be formulated in physiological buffers and excipients to high concentration (>100 mg/mL).

Plasma Stability of Å6

Å6 was stable in plasma at room temperature for 24 hrs (tested at 10 μg/mL). Å6 is stable as a lyophilized powder for at least 2 months (degradation is <1% by HPLC) and in PBS or water at 4° C. for at least 2 weeks.

Pharmacokinetics in Mice

Figure 22:
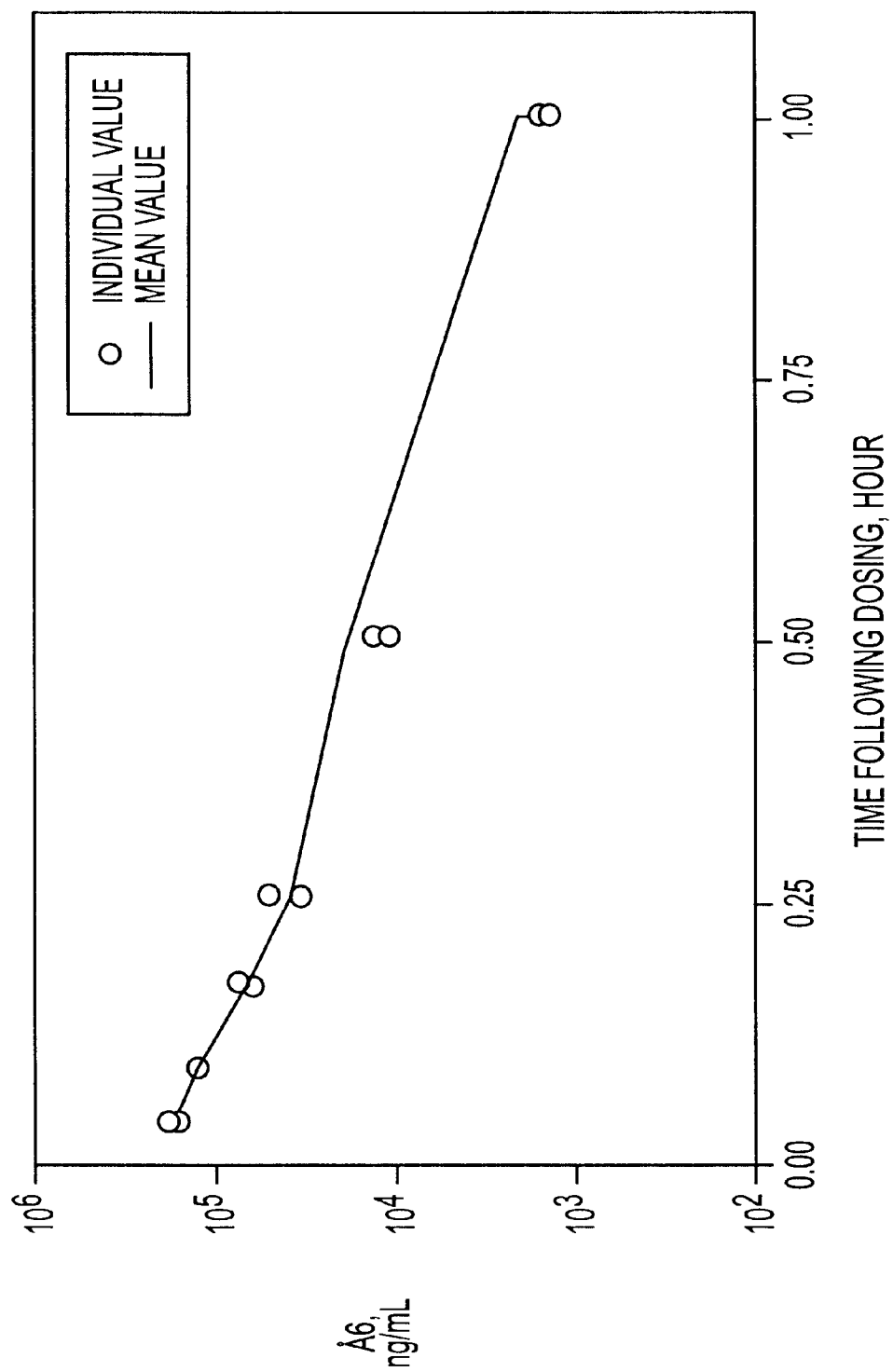
FIG. 22 shows the plasma concentration of A6 in mice following a single intravenous injection of 37.5 mg/kg.

Pharmacokinetic analysis was carried out by Gilbert Lam, MicroConstants. The plasma concentration profile of Å6 is depicted in FIG. 22. The pharmacokinetics of Å6 is characterized by a mono-exponential decline following a single bolus dose. The terminal half-life is 0.2 hour. The systemic clearance "CL" is 2.0 L/h/kg, which is moderate when compared to the liver blood flow of the mouse. Å6 has a small volume of distribution at steady-state, ($V_{ss}$=0.4064 L/kg). Low $V_{ss}$ results in high plasma concentrations of the peptide.

Pharmacokinetics in Monkeys

Figure 23:
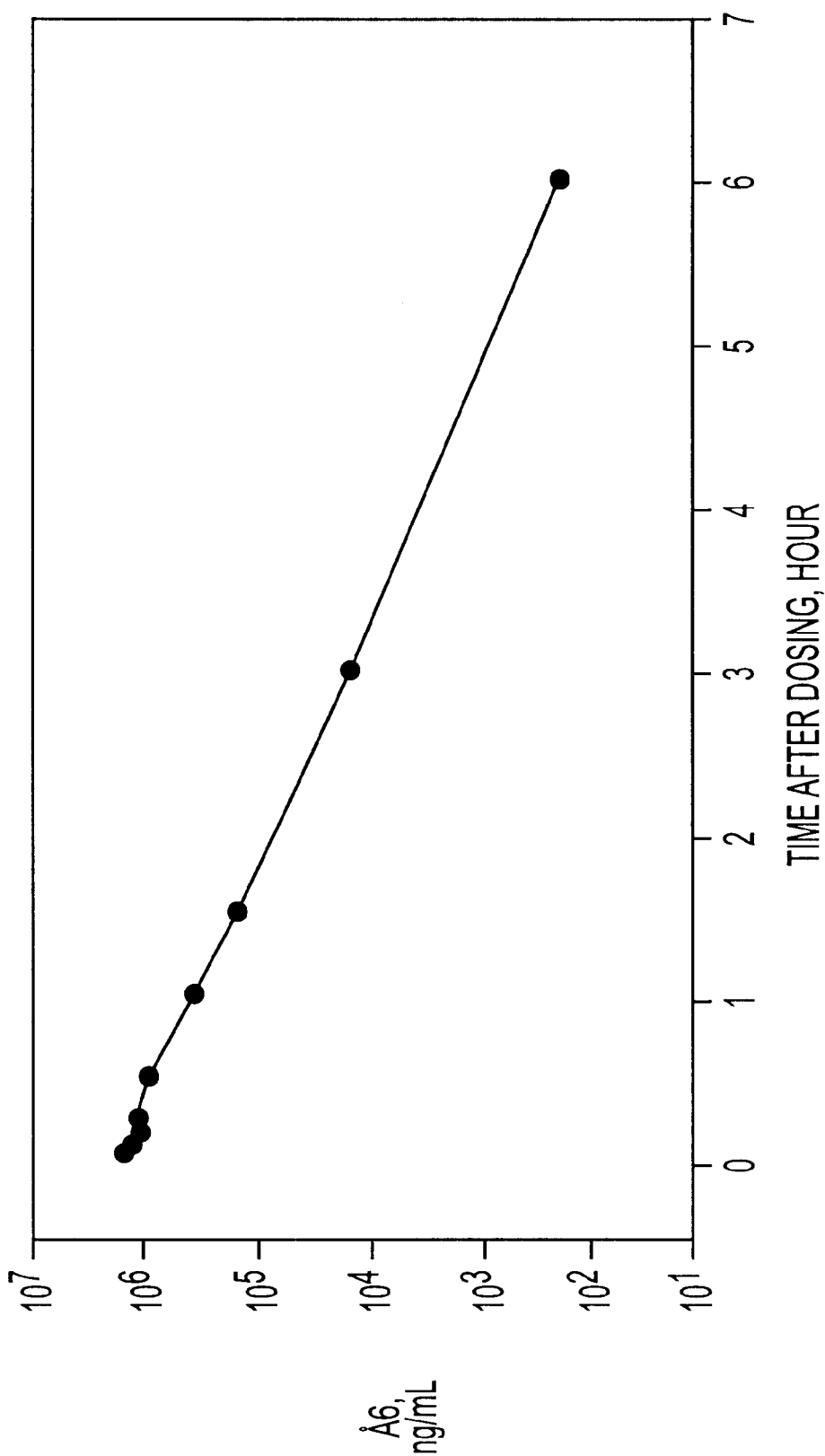
FIG. 23 shows the plasma concentration of A6 in Cynomolgus monkeys following a single intravenous injection of 37.5 mg/kg.

The plasma concentration profile of Å6 is depicted in FIG. 23. Å6 pharmacokinetics is characterized by a mono-exponential decline following a single bolus dose. The terminal half-life is 0.4 hour. The systemic clearance, CL, is 0.042 L/h/kg which is low when compared to either the kidney blood flow or the liver blood flow of the monkey. Å6 has a small volume of distribution at steady-state, $V_{ss}$= 0.0252 L/kg. Low $V_{ss}$ results in high plasma concentrations of the peptide.

Mouse Plasma Therapeutic Levels

The therapeutic plasma levels in mice receiving Å6 are being evaluated. Plasma concentration of Å6 will be measured in blood samples obtained from the dose-response studies in the glioblastoma model (above). This information is combined with allometric scaling data (see below) to predict therapeutic doses in man. This information will then be combined with toxicology data to establish starting doses for a Phase I trial.

Allometric Scaling

Figure 24:
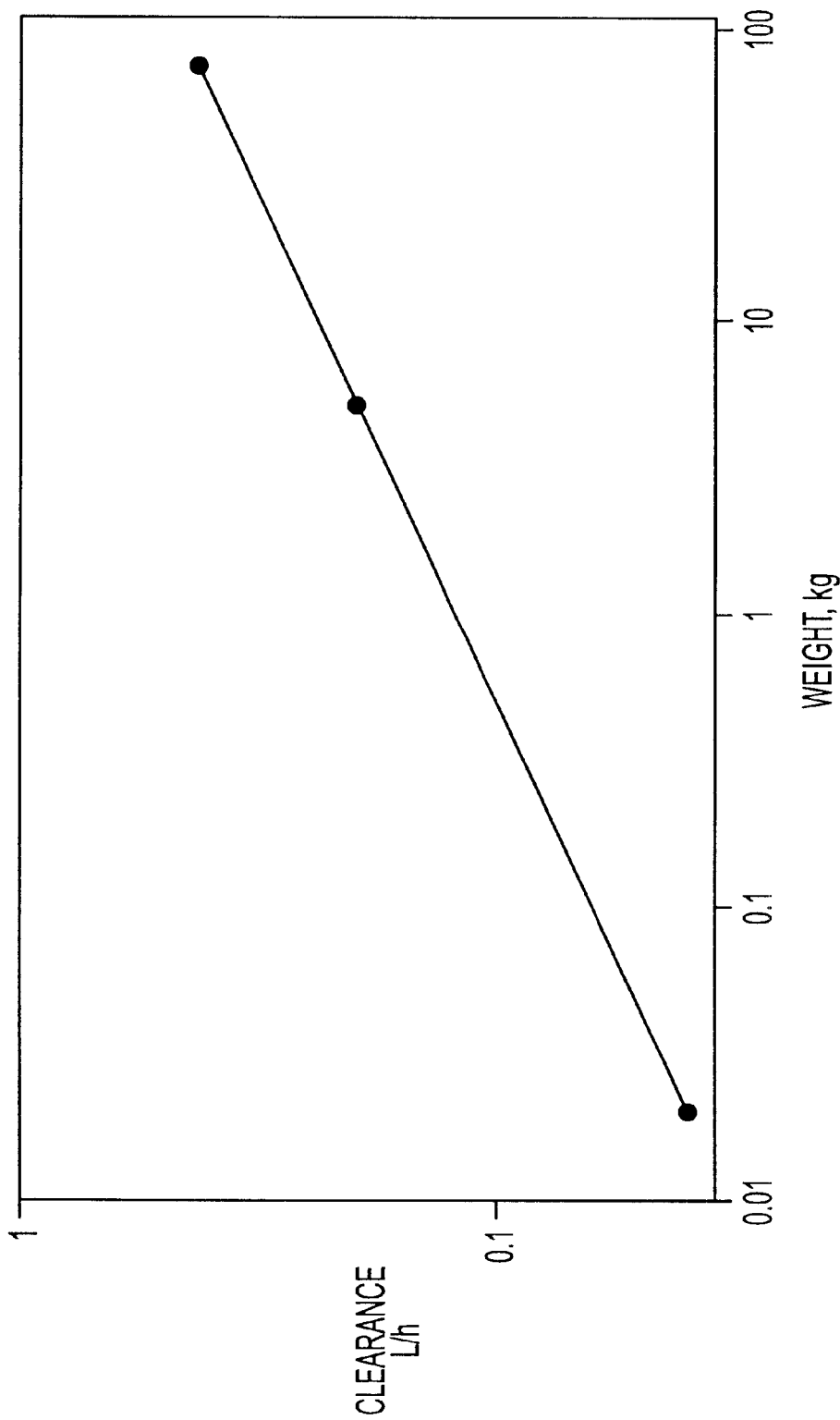
FIG. 24 shows allometric scaling of plasma clearance in animals.

Å6 is a particularly good candidate for allometric scaling analysis. The distribution of this compound is simple (i.e. after iv administration, the compound is not absorbed by, or distributed in, tissue but rather is restricted to the plasma) and is proportional to the plasma volume and therefore body weight. This makes the prediction of clearance in man fairly straightforward. Based on allometric scaling, it is expected that the CL in man is about 0.0061 L/h/kg (0.43 L/h for a 70 kg person) (FIG. 24). Extrapolations can also be made for other parameters such as $t_{1/2}$.

3. Toxicology

Acute toxicity was evaluated at three different doses of Å6 (1500 mg/kg, 500 mg/kg and 250 mg/kg). Mice (n=6) were infused (i.v.) with a bolus of Å6 over 5–10 minutes and observed for 3 days. No evidence for overt toxicity was observed, and all the animals survived and apparently tolerated the Å6 well.

Documents Cited

A number of documents are cited only in the text above (in full). Others, cited in abbreviated form in the text, are cited in full below.

Aznavoorian, S., Murphy, A. N., Stetler-Stevenson, W. G. and Liotta, L. A. (1993) "Molecular aspects of malignancy" Cancer 71(4): 1368–1383.

Blood, C. H. and Zetter, B. R. (1990) "Tumor interactions with the vasculature: Angiogenesis and tumor metastasis" Biochim. Biophys. Acta 1032: 89–118.

Bundgaard H, Ed: Design of Prodrugs, Elsevier, Amsterdam, 1985

Chambers, S. K., Wang, Y., Gertz, R. E. and Kacinski, B. M. (1995) "Macroph*age colony-stimulating factor mediates invasion of ovarian cancer cells through urokinase" Can. Res. 55: 1578–1585.

Cornelius, L. A., Nehring, L. C., Roby, J. D., Parks, W. C. and Welgus, H. G. 1995) "Human dermal microvascular endothelial cells produce matrix metalloproteinases in response to angiogenic factors and migration" J. Invest. Dermatol. 105: 170–176.

Crowley, C. W., Cohen, R. L., Lucas, B. K., Liu, G., Shuman, M. A. and Levinson, A. D. (1993) "Prevention of metastasis by inhibition of the urokinase receptor" Proc. Natl. Acad. Sci. USA 90 5021–5025.

Fernandez-Shaw, S., Marshall, J. M. and Hicks, B. (1995) "Plasminogen activators in ectopic and uterine endometrium" Fertil. and Steril. 63 (1): 45–51.

Fox, S. B., Gatter, K. C. and Harris, A. L. (1996) "Tumour angiogenesis" J. Pathol. 179: 232–237.

Gross et al., The Peptides: Analysis, Structure, Biology, Vol. 1: Major Methods of Peptide Bond Formation; Vol. 3: Protection of Functional Groups in Peptide Synthesis, Academic Press, New York, 1979, 1981.

Hoosein, N. M., Boyd, D. D., Hollas, W. J., Mazar, A., Henkin, J. and Chung, L. W. K. (1991) "Involvement of urokinase and its receptor in the invasiveness of human prostatic carcinoma cell lines" Cancer Comm. 3 (8): 255–264.

Horiki et al., Chem. Lett. 165:168 (1978)

Kaiser et al., Anal. Biochem. 34:595 (1970)

Kleinman, H. K., McGarvey, M. L., Hassell, J. R., Star, V. L., Cannon, F. B., Laurie, G. W. and Martin, G. R. (1986) "Basement membrane complexes with biological activity" Biochemistry 25: 312–318.

Leek, R. D., Harris, A. L. and Lewis, C. E. (1994) "Cytokine networks in solid human tumors: regulation of angiogenesis" J. Leukocyte Biol. 56: 423–435.

Lennarz, W. J. and Strittmater, W .J. (1991) "Cellular functions of metallo-endoproteinases" Biochim. Biophys. Acta 1071: 149–158.

Liotta, L. A., Steeg, P. S. and Stetler-Stevenson, W. G. (1991) "Cancer metastasis and angiogenesis: An imbalance of positive and negative regulation" Cell 64: 327–336.

Lübke et al., Chemie und Biochemie der Aminosaüren, Peptide und Proteine I, Chapter II-1, 102–117 (Georg Thieme Verlag, Stuttgart, 1975), Mareel, M. M., Van Roy, F. M. and De Baetselier, P. (1990) "The invasive phenotypes" Cancer and Metastasis Rev. 9: 45–62.

Min, H. Y., Doyle, L. V., Vitt, C. R., Zandonella, C. L., Stratton-Thomas, J. R., Shuman, M. A. and Rosenberg, S. (1996) "Urokinase receptor antagonists inhibit angiogenesis and primary tumor growth in syngeneic mice" Cancer Res. 56: 2428–2433.

Moore et al., Peptides, Proc. Fifth Amer. Pept. Symp., Goodman et al., eds., 1977, pp 518–521

Odedra, R. and Weiss, J. B. (1991) "Low-molecular weight angiogenesis factors" Pharmac. Ther. 49: 111–124.

Osbom, L. (1990) "Leukocyte adhesion to endothelium in inflammation" Cell 62: 3–6.

Parish, C. R., Jakobsen, K. B. and Coombe, D. R. (1992) "A basement-membrane permeability assay which correlates with the metastatic potential of tumor cells" Int. J. Cancer 52: 378–383.

Penfold, C. N., Partridge, M., Rojas, R. and Langdon J. D. (1996) "The role of angiogenesis in the spread of oral squamous cell carcinoma" Br. J. Oral and Maxill. Surg. 34: 37–41.

Rabbani, S. A., Harakidas, P., Davidson, D., Henkin, J., and Mazar, A. P. (1995) "Prevention of prostate cancer metastasis in vivo by a novel synthetic inhibitor of urokinase-type plasminogen activator (uPA)" Int. J. Cancer 63: 840–845.

Schnaper, H. W., Bamathan, E. S., Mazar, A. P., Maheshwari, S., Ellis, S.,and Kleinman, H. K.(1995) "Plasminogen activators augment endothelial cell organization in vitro by two distinct pathways." J. Cell. Phys. 165:: 107–118.

Sweeney, T. M., Kibbey, M. C., Zain, M., Fridman, R. and Kleinman, H. K. (1991) "Basement membrane and the SIKVAV laminin-derived peptide promote tumor growth and metastases" Cancer and Metastasis Rev. 10: 245–254.

Taipale, J. and Keski-Oj a, J. (1997) "Growth factors in the extracellular matrix" FASEB J. 11: 51–59.

Vlodavsky, I., Komer, G., Ishai-Michaeli, R., Bashkin, P., Bar-Shavit, R. and Fuks, Z. (1990) "Extracellular matrixresident growth factors and enzymes: possible involvement in tumor metastasis and angiogenesis" Cancer and Metastasis Rev. 9: 203–226.

Weaver, V. M., Petersen, O. and Bissell, M. (1997) J. Cell Biol. 137: 231–246.

Weinstat-Saslow, D. and Steeg, P. S. (1994) "Angiogenesis and colonization in the tumor metastatic process: basic and applied advances" FASEB J. 8: 401–407.

Welch, D. R. (1997) "Technical considerations for studying cancer metastasis in vivo" Clin. Exp. Metastasis 15: 272–306.

Xing, R. H. and Rabbani, S. A. (1996) "Overexpression of urokinase receptor in breast cancer cells results in increased tumor invasion, growth and metastasis" Int. J. Cancer 67: 423–429.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A synthetic chemical peptide multimer comprising the sequence Lys-Pro-Ser-Ser-Pro-Pro-Glu-Glu (SEQ ID NO:2), or comprising
   (i) a substitution variant of SEQ ID NO:2, or
   (ii) an addition variant of SEQ ID NO:2 having up to 11 additional amino acids, the multimer having a formula:

$(P^1—X_m)_n—P^2$ wherein:
   (a) $P^1$ and $P^2$ are peptides either or both of which are SEQ ID NO:2, or said substitution or addition variant, and wherein $P^1$ and $P^2$ may be the same or different;
   (b) X is selected from the group consisting of $C_1$–$C_{20}$ alkyl, $C_1$–$C_{20}$ alkenyl, $C_1$–$C_{20}$ alkynyl, and $C_1$–$C_{20}$ polyether containing up to 9 oxygen atoms wherein m=0 or 1 and n=1–7
   (c) said multimer is optionally capped at its N- and C-termini, and wherein said multimer has one or more of the following activities:
      (1) at least about 20% of the biological activity of Ac-Lys-Pro-Ser-Ser-Pro-Pro-Glu-Glu-Am in an in vitro bioassay of cell invasion or endothelial tube formation; or
      (2) competes with labeled Ac-Lys-Pro-Ser-Ser-Pro-Pro-Glu-Glu-Am for binding to a cell or molecule which has a binding site for Ac-Lys-Pro-Ser-Ser-Pro-Pro-Glu-Glu-Am.

2. The peptide multimer of claim 1 wherein $P^1$ and/or $P^2$ is a substitution or addition variant selected from the group consisting of:
   (a) SEQ ID NO:2 wherein the Glu at position 7 or 8 or both is replaced by one or any two of the substituent amino acids Gln, Asp or Asn;
   (b) SEQ ID NO:2 wherein Ser at position 3 or 4 or both is replaced by one or any two of the substituent amino acids Thr, Ala, Gly, hSer or ValβOH;
   (c) SEQ ID NO:2 wherein the Lys at position 1 is replaced by His, Arg, Gln, Orn, Cit or Hci;
   (d) SEQ ID NO:2 wherein the Pro at position 2, 5 or 6 is replaced by Hyp;
   (e) an addition variant of SEQ ID NO:2, wherein Leu, Ile, Val, Nva, Nle, Met, Ala, or Gly is added to the C-terminal Glu or to any of said substituents for Glu at position 8;
   (f) an addition variant of SEQ ID NO:2, wherein any of the following peptides are added to the C-terminal Glu or to any of said substituents for Glu at position 8: Leu-$(Gly)_n$; Ile-$(Gly)_n$; Val-$(Gly)_n$; Nva-$(Gly)_n$; or Nle-$(Gly)_n$, wherein n=1–10;
   (g) an addition variant of SEQ ID NO:2 wherein one or more of the following residues or peptides is added to the N-terminal Lys or to any of said N-terminal substituents of Lys at position 1: Gly, Lys-$(Gly)_n$; Tyr-$(Gly)_n$; or Gly-$(Gly)_n$, wherein n=1–10; and
   (h) a combination of one or more of (a)–(g).

3. A pharmaceutical composition useful for inhibiting cell invasion or angiogenesis, comprising:
   (a) the peptide multimer of claim 1; and
   (b) a pharmaceutically acceptable carrier or excipient.

4. A pharmaceutical composition useful for inhibiting cell invasion or angiogenesis, comprising:
   (a) the peptide multimer of claim 2; and
   (b) a pharmaceutically acceptable carrier or excipient.

5. A recombinantly produced peptide multimer comprising the sequence Lys-Pro-Ser-Ser-Pro-Pro-Glu-Glu (SEQ ID NO:2), or comprising (i) a substitution variant of SEQ ID NO:2, or (ii) an addition variant of SEQ ID NO:2 having up to 11 additional amino acids, the multimer having a formula:

$(P^1—Gly_z)_n—P^2$ wherein:
   (a) $P^1$ and $P^2$ are peptides either or both of which are SEQ ID NO:2, or said substitution or addition variants, and wherein $P^1$ and $P^2$ may be the same or different; wherein n=1–100 and z=0–10;
   (b) said multimer is optionally capped at its N- and C-termini, and wherein said multimer has one or more of the following activities:
      (1) at least about 20% of the biological activity of Ac-Lys-Pro-Ser-Ser-Pro-Pro-Glu-Glu-Am in an in vitro bioassay of cell invasion or endothelial tube formation; or
      (2) competes with labeled Ac-Lys-Pro-Ser-Ser-Pro-Pro-Glu-Glu-Am for binding to a cell or molecule which has a binding site for Ac-Lys-Pro-Ser-Ser-Pro-Pro-Glu-Glu-Am.

6. The peptide multimer of claim 5 wherein $P^1$ and/or $P^2$ is a substitution or addition variant selected from the group consisting of:
   (a) SEQ ID NO:2 wherein the Glu at position 7 or 8 or both is replaced by one or any two of the substituent amino acids Gln, Asp or Asn;
   (b) SEQ ID NO:2 wherein Ser at position 3 or 4 or both is replaced by one or any two of the substituent amino acids Thr, Ala, Gly, hSer or ValβOH;
   (c) SEQ ID NO:2 wherein the Lys at position 1 is replaced by His, Arg, Gln, Orn, Cit or Hci;
   (d) SEQ ID NO:2 wherein the Pro at position 2, 5 or 6 is replaced by Hyp;
   (e) an addition variant of SEQ ID NO:2, wherein Leu, Ile, Val, Nva, Nle, Met, Ala, or Gly is added to the C-terminal Glu or to any of said substituents for Glu at position 8;
   (f) an addition variant of SEQ ID NO:2, wherein any of the following peptides are added to the C-terminal Glu or to any of said substituents for Glu at position 8: Leu-$(Gly)_n$; Ile-$(Gly)_n$; Val-$(Gly)_n$; Nva-$(Gly)_n$; or Nle-$(Gly)_n$, wherein n=1–10;
   (g) an addition variant of SEQ ID NO:2 wherein one or more of the following residues or peptides is added to the N-terminal Lys or to any of said N-terminal substituents of Lys at position 1: Gly, Lys-$(Gly)_n$; Tyr-$(Gly)_n$; or Gly-$(Gly)_n$, wherein n=1–10; and
   (h) a combination of one or more of (a)–(g).

7. A pharmaceutical composition useful for inhibiting cell invasion or angiogenesis, comprising:
   (a) the peptide multimer of claim 5; and
   (b) a pharmaceutically acceptable carrier or excipient.

8. A pharmaceutical composition useful for inhibiting cell invasion or angiogenesis, comprising:
   (a) the peptide multimer of claim 6; and
   (b) a pharmaceutically acceptable carrier or excipient.

* * * * *

UNITED STATES PATENT AND TRADEMARK OFFICE
CERTIFICATE OF CORRECTION

PATENT NO.    : 6,696,416 B1
DATED         : February 24, 2004
INVENTOR(S)   : Mazar et al.

It is certified that error appears in the above-identified patent and that said Letters Patent is hereby corrected as shown below:

Column 47,
Line 42, please delete "Om" and replace therefor with -- Orn. --

Column 48,
Line 38, please delete "Om" and replace therefor with -- Orn. --

Signed and Sealed this

Tenth Day of August, 2004

JON W. DUDAS
*Acting Director of the United States Patent and Trademark Office*

SEQUENCE LISTING

```
(1) GENERAL INFORMATION:

(iii) NUMBER OF SEQUENCES: 9

(2) INFORMATION FOR SEQ ID NO: 1:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (A) NAME/KEY: Modified Amino Acid
        (B) LOCATION: 1
        (D) OTHER INFORMATION: May be capped with an acetyl ("Ac").

(A) NAME/KEY: Modified Amino Acid
        (B) LOCATION: 10
        (D) OTHER INFORMATION: May be capped with an amido group
            ("Am").

(xi) SEQUENCE DESCRIPTION: SEQ ID NO: 1:

Lys Pro Ser Ser Pro Pro Glu Glu Leu Lys
 1               5                  10

(2) INFORMATION FOR SEQ ID NO: 2:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
        (A) NAME/KEY: Modified Amino Acid
        (B) LOCATION: 1
        (D) OTHER INFORMATION: May be capped with an acetyl ("Ac").

(A) NAME/KEY: Modified Amino Acid
        (B) LOCATION: 8
        (D) OTHER INFORMATION: May be capped with an amido group
            ("Am").

(xi) SEQUENCE DESCRIPTION: SEQ ID NO: 2:

Lys Pro Ser Ser Pro Pro Glu Glu
 1               5
```

(2) INFORMATION FOR SEQ ID NO: 3:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (ix) FEATURE:
        (A) NAME/KEY: Amino Acid to which is bound an amino terminal
            group
        (B) LOCATION: 1
        (D) OTHER INFORMATION: X attached to Pro is a peptidomimetic
            compound (xi) SEQUENCE DESCRIPTION: SEQ ID NO: 3:

Pro Pro Glu Glu
1

(2) INFORMATION FOR SEQ ID NO: 4:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: Modified Amino Acid
        (B) LOCATION: 1
        (D) OTHER INFORMATION: May be capped with an acetyl ("Ac").

(A) NAME/KEY: Modified Amino Acid
        (B) LOCATION: 7
        (D) OTHER INFORMATION: May be capped with an amido group
            ("Am").

(xi) SEQUENCE DESCRIPTION: SEQ ID NO: 4:

Pro Ser Ser Pro Pro Glu Glu
1               5

(2) INFORMATION FOR SEQ ID NO: 5:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (ix) FEATURE:
        (A) NAME/KEY: Modified Amino Acid
        (B) LOCATION: 1
        (D) OTHER INFORMATION: May be capped with an acetyl ("Ac").

(A) NAME/KEY: Modified Amino Acid
        (B) LOCATION: 7
        (D) OTHER INFORMATION: May be capped with an amido group
            ("Am").

(xi) SEQUENCE DESCRIPTION: SEQ ID NO: 5:

Lys Pro Ser Ser Pro Pro Glu
1               5

(2) INFORMATION FOR SEQ ID NO: 6:

(i) SEQUENCE CHARACTERISTICS:
        (A) LENGTH: 8 amino acids
        (B) TYPE: amino acid
        (D) TOPOLOGY: linear

```
    (ii) MOLECULE TYPE: peptide (ix) FEATURE:
         (A) NAME/KEY: Modified Amino Acid
         (B) LOCATION: 1
         (D) OTHER INFORMATION: May be capped with an acetyl ("Ac").

(A) NAME/KEY: Modified Amino Acid
         (B) LOCATION: 8
         (D) OTHER INFORMATION: May be capped with an amido group
             ("Am").

(xi) SEQUENCE DESCRIPTION: SEQ ID NO: 6:

Lys Pro Thr Thr Pro Pro Glu Glu
 1               5

(2) INFORMATION FOR SEQ ID NO: 7:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (ix) FEATURE:
         (A) NAME/KEY: Modified Amino Acid
         (B) LOCATION: 1
         (D) OTHER INFORMATION: May be capped with an acetyl ("Ac").

(A) NAME/KEY: Modified Amino Acid
         (B) LOCATION: 8
         (D) OTHER INFORMATION: May be capped with an amido group
             ("Am").

(xi) SEQUENCE DESCRIPTION: SEQ ID NO: 7:

Lys Pro Ser Ser Pro Pro Asp Asp
 1               5

(2) INFORMATION FOR SEQ ID NO: 8:

(i) SEQUENCE CHARACTERISTICS:
        (A) LENGTH: 8 amino acids
        (B) TYPE: amino acid
        (D) TOPOLOGY: linear (ii) MOLECULE TYPE: peptide (xi) SEQUENCE DESCRIPTION: SEQ ID NO: 8:

Arg Pro Ser Ser Pro Pro Glu Glu
 1               5

(2) INFORMATION FOR SEQ ID NO: 9:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO: 9:

Lys Pro Ser Ser
 1
```